US011613756B2

(12) United States Patent
Lee et al.

(10) Patent No.: US 11,613,756 B2
(45) Date of Patent: Mar. 28, 2023

(54) COMPOSITIONS AND METHODS FOR DIFFERENTIAL INDUCTION OF CELL DEATH AND INTERFERON EXPRESSION

(71) Applicant: Duke University, Durham, NC (US)

(72) Inventors: Jaewoo Lee, Durham, NC (US); Bruce A. Sullenger, Durham, NC (US); Youngju Lee, Durham, NC (US)

(73) Assignee: Duke University, Durham, NC (US)

( * ) Notice: Subject to any disclaimer, the term of this patent is extended or adjusted under 35 U.S.C. 154(b) by 202 days.

(21) Appl. No.: 16/499,991

(22) PCT Filed: Apr. 3, 2018

(86) PCT No.: PCT/US2018/025884
§ 371 (c)(1),
(2) Date: Oct. 1, 2019

(87) PCT Pub. No.: WO2018/187328
PCT Pub. Date: Oct. 11, 2018

(65) Prior Publication Data
US 2020/0109404 A1 Apr. 9, 2020

Related U.S. Application Data

(60) Provisional application No. 62/480,780, filed on Apr. 3, 2017.

(51) Int. Cl.
*C12N 15/117* (2010.01)

(52) U.S. Cl.
CPC ........ *C12N 15/117* (2013.01); *C12N 2310/17* (2013.01); *C12N 2310/531* (2013.01)

(58) Field of Classification Search
CPC .............. C12N 15/117; C12N 2310/17; C12N 2310/531
See application file for complete search history.

(56) References Cited

U.S. PATENT DOCUMENTS

| 9,861,574 B2 | 1/2018 | Lee |
| 2010/0260788 A1 | 10/2010 | Debelak |
| 2011/0244025 A1 | 10/2011 | Uhlmann |
| 2012/0107272 A1 | 5/2012 | Manoharan |
| 2012/0220761 A1 | 8/2012 | Zlatev |
| 2016/0017334 A1 | 1/2016 | Hiscott |
| 2016/0030332 A1* | 2/2016 | Lee ........................ A61K 9/127 424/450 |

FOREIGN PATENT DOCUMENTS

| WO | 2010/028079 | 3/2010 |
| WO | 2012/027467 | 3/2012 |
| WO | 2014/049079 | 4/2014 |
| WO | 2014/066915 | 5/2014 |
| WO | 2014/169049 | 10/2014 |
| WO | 2016/011324 | 1/2016 |
| WO | 2017/001702 | 1/2017 |

OTHER PUBLICATIONS

Lee et al. (Molecular Therapy (2017) 25(6):1295-1305 (Epub Mar. 31, 2017)). (Year: 2017).*
Abbas, Y.M., et al. (2013) Structural basis for viral 5'-PPP-RNA recognition by human IFIT proteins, Nature, 2013, pp. 60-64, vol. 494.
Alonso, DF, et al. (2011). Metastasis: recent discoveries and novel perioperative treatment strategies with particular interest in the hemostatic compound desmopressin. Curr Pharm Biotechnol 12: 1974-1980.
Besch, R., et al., Proapoptotic signaling induced by RIG-I and MDA-5 results in type I interferon-independent apoptosis in human melanoma cells, The Journal of clinical investigation, 2009, pp. 2399-2411, vol. 119.8.
Blander, JM (2014). A long-awaited merger of the pathways mediating host defence and programmed cell death. Nat Rev Immunol 14: 601-618.
Casares, N, et al. (2005). Caspase-dependent immunogenicity of doxorubicin-induced tumor cell death. J Exp Med 202: 1691-1701.
Chattopadhyay, S, et al. (2010). Viral apoptosis is induced by IRF-3-mediated activation of Bax. EMBO J 29: 1762-1773.
Chawla-Sarkar, M, et al. (2001). Preferential induction of apoptosis by interferon (IFN)-beta compared with IFN-alpha2: correlation with TRAIL/Apo2L induction in melanoma cell lines. Clin Cancer Res 7:1821-1831.
Cheng, Y.S. et al., Anticancer function of polyinosinic-polycytidylic acid. Cancer biology & therapy, 2011, 1219-1223, vol. 10:12.
Colli, M.L., et al., Exposure to the viral by-product dsRNA or Coxsackievirus B5 triggers pancreatic beta cell apoptosis via a Bim / Mcl-1 imbalance, PLoS pathogens, 2011, e1002267, vol. 7:9.
Dassie, J.P., et al., Systemic administration of optimized aptamer-siRNA chimeras promotes regression of PSMA-expressing tumors, Nature biotechnology, 2009, pp. 839-849, vol. 27.
Diebold, S.S., et al., Innate antiviral responses by means of TLR7-mediated recognition of single-stranded RNA, Science, 2004, pp. 1529-1531, vol. 303.

(Continued)

*Primary Examiner* — J. E. Angell

(74) *Attorney, Agent, or Firm* — Quarles & Brady LLP

(57) ABSTRACT

Disclosed herein are compositions and methods for inhibiting the growth of cells or inducing cell death. The composition capable of inhibiting the growth of cells or inducing cell death comprises a 5'-triphosphate non-linear RNA. The RNA comprises a first stem-loop formed from the complete or partial hybridization of at least 8 nucleotide pairings and may optionally comprise a second stem-loop formed from the complete or partial hybridization of at least 8 nucleotide pairings and a spacer between the first stem-loop and the second stem loop. Methods for inhibiting the growth of cells or inducing cell death comprise contacting cells with the composition or administering the composition to a subject in an amount effective to inhibit the growth of the cells or induce death of the cells.

20 Claims, 28 Drawing Sheets

Specification includes a Sequence Listing.

(56) References Cited

OTHER PUBLICATIONS

Duewell, P, et al. (2014). RIG-l-like helicases induce immunogenic cell death of pancreatic cancer cells and sensitize tumors toward killing by CD8(+) T cells. Cell Death Differ 21: 1825-1837.

Duewell, P, et al. (2015). Targeted activation of melanoma differentiation-associated protein 5 (MDA5) for immunotherapy of pancreatic carcinoma. Oncoimmunology 4: e1029698.

Emens, L.A., Chemoimmunotherapy, Cancer J, 2010, pp. 295-303, vol. 16:4.

Estornes, Y., et al., dsRNA induces apoptosis through an atypical death complex associating TLR3 to caspase-8, Cell death and differentiation, 2012, 1482-1494, vol. 19.

Gando, S, et al. (2015). Local hemostasis, immunothrombosis, and systemic disseminated intravascular coagulation in trauma and traumatic shock. Crit Care 19: 72.

Glas, M, et al. (2013). Targeting the cytosolic innate immune receptors RIG-I and MDA5 effectively counteracts cancer cell heterogeneity in glioblastoma. Stem Cells 31: 1064-1074.

Green, DR, et al. (2009). Immunogenic and tolerogenic cell death. Nat Rev Immunol 9: 353-363.

He, Wa, et al. (2014). Microvesicles containing miRNAs promote muscle cell death in cancer cachexia via TLR7. Proc Natl Acad Sci U S A 111: 4525-1529.

Heil, F., et al., Species-specific recognition of single-stranded RNA via toll-like receptor 7 and 8, Science, 2004, pp. 1526-1529, vol. 303.

Hornung, V., et al., 5'-Triphosphate RNA is the ligand for RIG-I, Science, 2006, pp. 994-997, vol. 314.

Hwang, S.Y., et al., 5'-Triphosphate-RNA-independent activation of RIG-I via RNA aptamer with enhanced antiviral activity, Nucleic acids research, 2012, pp. 2724-2733, vol. 40:6.

International Searching Authority, International Search Report and Written Opinion for application PCT/US2018/25884. dated Sep. 11, 2018.

Ishibashi, O., et al., Short RNA duplexes elicit RIG-l-mediated apoptosis in a cell type- and length-dependent manner, Science signaling, 2011, ra74, vol. 4.

Jensen, S, et al. (2012). Sensing of RNA viruses: a review of innate immune receptors involved in recognizing RNA virus invasion. J Virol 86: 2900-2910.

Jiang, F., et al., Structural basis of RNA recognition and activation by innate immune receptor RIG-I, Nature, 2011, pp. 423-427, vol. 479.

Jiang, M., et al., Innate immune responses in human monocyte-derived dendritic cells are highly dependent on the size and the 5' phosphorylation of RNA molecules, J Immunol, 2011, pp. 1713-1721, vol. 187.

Jockel, S., et al., The 2'-O-methylation status of a single guanosine controls transfer RNA-mediated Toll-like receptor 7 activation or inhibition, The Journal of experimental medicine, 2012, pp. 235-241, vol. 209.

Judge, A.D., et al., Design of noninflammatory synthetic siRNA mediating potent gene silencing in vivo, Molecular therapy : the journal of the American Society of Gene Therapy, 2006, pp. 494-505, vol. 13.

Kaczanowska, S, et al. (2013). TLR agonists: our best frenemy in cancer immunotherapy. J Leukoc Biol 93: 347-863.

Kato, H, et al. (2008). Length-dependent recognition of double-stranded ribonucleic acids by retinoic acid-inducible gene-I and melanoma differentiation-associated gene 5. J Exp Med 205: 1601-1610.

Kazama, H, et al. (2008). Induction of immunological tolerance by apoptotic cells requires caspase-dependent oxidation of high-mobility group box-1 protein. Immunity 29: 21-32.

Kleinman, Me, et al. (2008). Sequence- and target-independent angiogenesis suppression by siRNA via TLR3. Nature 452: 591-597.

Kohlway, A., et al. "Defining the functional determinants for RNA surveillance by RIG-I." EMBO reports 14.9 (2013) 772-779.

Kroemer, G, et al. (2013). Immunogenic cell death in cancer therapy. Annual review of immunology 31: 51-72.

Kubler, K., et al., Immunogenic cell death of human ovarian cancer cells induced by cytosolic poly(I:C) leads to myeloid cell maturation and activates NK cells, European journal of immunology, 2011, pp. 3028-3039, vol. 41.

Kubler, K., et al., Targeted activation of RNA helicase retinoic acid-inducible gene-I induces proimmunogenic apoptosis of human ovarian cancer cells, Cancer research, 2010, pp. 5293-5304, vol. 70.

Lampkin, BC, et al. (1985). Phase II trial of a complex polyriboinosinic-polyribocytidylic acid with poly-L-lysine and carboxymethyl cellulose in the treatment of children with acute leukemia and neuroblastoma: a report from the Children's Cancer Study Group. Cancer Res 45: 5904-5909.

Lee, J. et al. "Differential Induction of Immunogenic Cell Death and Interferon Expression in Cancer Cells by Structured ssRNAs" Molecular Therapy (2017) 25(6):1295-1305.

Lee, J. et al. "Supplemental Information: Differential Induction of Immunogenic Cell Death and Interferon Expression in Cancer Cells by Structured ssRNAs" Molecular Therapy (2017).

Lee, Y, et al. (2016). 2'Fluoro Modification Differentially Modulates the Ability of RNAs to Activate Pattern Recognition Receptors. Nucleic Acid Ther 26: 173-182.

Lehmann, S.M., et al., Extracellularly delivered single-stranded viral RNA causes neurodegeneration dependent on TLR7, J Immunol, 2012, pp. 1448-1458, vol. 189.

Lion, E., et al., Poly(I:C) enhances the susceptibility of leukemic cells to NK cell cytotoxicity and phagocytosis by DC, PloS one, 2011, e20952, vol. 6.

Longley, D.B., et al., 5-fluorouracil: mechanisms of action and clinical strategies, Nature review: Cancer, 2003, pp. 330-338, vol. 3:5.

Manoharan, M., et al., Unique gene-silencing and structural properties of 2'-fluoro-modified siRNAs, Angewandte Chemie, 2011, pp. 2284-2288, vol. 50.

Matsushima-Miyagi, T., et al., TRAIL and Noxa are selectively upregulated in prostate cancer cells downstream of the RIG-I/MAVS signaling pathway by nonreplicating Sendai virus particles, Clinical cancer research : an official journal of the American Association for Cancer Research, 2012, pp. 6271-6283, vol. 18.

Mumm, JB, et al. (2008). Cytokine-based transformation of immune surveillance into tumor-promoting inflammation. Oncogene 27: 5913-5919.

Nimjee, S.M., et al., Rapidly regulating platelet activity in vivo with an antidote controlled platelet inhibitor, Molecular therapy : the journal of the American Society of Gene Therapy, 2012, pp. 391-397, vol. 20.

Palchetti, S, et al. (2015). Transfected poly(I:C) activates different dsRNA receptors, leading to apoptosis or immunoadjuvant response in androgen-independent prostate cancer cells. J Biol Chem 290: 5470-5483.

Pallan, P.S., et al., Unexpected origins of the enhanced pairing affinity of 2'-fluoro-modified RNA, Nucleic acids research, 2011, pp. 3482-3495, vol. 39.

Pandey, S, et al. (2015). Microbial sensing by Toll-like receptors and intracellular nucleic acid sensors. Cold Spring Harb Perspect Biol 7: a016246.

Peng, S, et al. (2009). Polyinosinic-polycytidylic acid liposome induces human hepatoma cells apoptosis which correlates to the up-regulation of RIG-I like receptors. Cancer Sci 100: 529-536.

Poeck, H., et al., 5'-Triphosphate-siRNA: turning gene silencing and Rig-I activation against melanoma, Nature medicine, 2008, pp. 1256-1263, vol. 14.

Robbins, M., et al., 2'-O-methyl-modified RNAs act as TLR7 antagonists, Molecular therapy : the journal of the American Society of Gene Therapy, 2007, pp. 1663-1669, vol. 15.

Robinson, N, et al. (2012). Type I interferon induces necroptosis in macrophages during infection with *Salmonella enterica* serovar Typhimurium. Nat Immunol 13: 954-962.

Sabbah, A, et al. (2009). Activation of innate immune antiviral responses by Nod2. Nat Immunol 10: 1073-1080.

Salaun, B, et al. (2006). TLR3 can directly trigger apoptosis in human cancer cells. J Immunol 176: 4894-4901.

(56) References Cited

OTHER PUBLICATIONS

Schmidt, A., et al., 5'-triphosphate RNA requires base-paired structures to activate antiviral signaling via RIG-I, Proceedings of the National Academy of Sciences of the United States of America, 2009, pp. 12067-12072, vol. 106.

Shir, A., et al., EGF receptor-targeted synthetic double-stranded RNA eliminates glioblastoma, breast cancer, and adenocarcinoma tumors in mice, PLoS medicine, 2006, e6, vol. 3.

Sioud, M., Development of TLR7/8 small RNA antagonists, Methods Mol Biol,, 2010, pp. 387-394, vol. 629.

Sioud, M., Single-stranded small interfering RNA are more immunostimulatory than their double-stranded counterparts: a central role for 2'-hydroxyl uridines in immune responses, European journal of immunology, 2006, pp. 1222-1230, vol. 36.

Song, W, et al. (2015). Structural basis for specific recognition of single-stranded RNA by Toll-like receptor 13. Nat Struct Mol Biol 22: 782-787.

Thiel, K.W. et al., Intracellular delivery of RNA-based therapeutics using aptamers, Therapeutic delivery, 2010, pp. 849-861, vol. 1.

Tormo, D., et al., Targeted activation of innate immunity for therapeutic induction of autophagy and apoptosis in melanoma cells, Cancer cell, 2009, pp. 103-114, vol. 16.

Toroney, R., et al., Mechanistic characterization of the 5'-triphosphate-dependent activation of PKR: lack of 5'-end nucleobase specificity, evidence for a distinct triphosphate binding site, and a critical role for the dsRBD, RNA, 2012, pp. 1862-1874, vol. 18.

Trinchieri, G. et al., Cooperation of Toll-like receptor signals in innate immune defense, Nature reviews. Immunology, 2007, pp. 179-190, vol. 7.

Trinchieri, G., Type I interferon: friend or foe?, The Journal of experimental medicine, 2010, pp. 2053-2063, vol. 207.

Uzri, D. et al., Nucleotide sequences and modifications that determine RIG-I/RNA binding and signaling activities, Journal of virology, 2009, pp. 4174-4184, vol. 83.

Vacchelli, E, et al. (2013). Trial Watch: Toll-like receptor agonists for cancer therapy. Oncoimmunology 2: e25238.

Vermes, I, et al. (1995). A novel assay for apoptosis. Flow cytometric detection of phosphatidylserine expression on early apoptotic cells using fluorescein labelled Annexin V. Journal of immunological methods 184: 39-51.

Wang, Y., et al., Structural and functional insights into 5'-ppp RNA pattern recognition by the innate immune receptor RIG-I, Nature structural & molecular biology, 2010, pp. 781-787, vol. 17.

Yang, H, et al. (2013). The many faces of HMGB1: molecular structure-functional activity in inflammation, apoptosis, and chemotaxis. J Leukoc Biol 93: 865-873.

Yu, N., et al., Double-stranded RNA induces melanocyte death via activation of Toll-like receptor 3, Experimental dermatology, 2011, pp. 134-139, vol. 20.2.

Yu, X, et al. (2016). Activation of the MDA5-IPS1 viral sensing pathway induces cancer cell death and type I interferon-dependent antitumor immunity. Cancer Res. 76(8): 2166-2176.

Zust, R., et al., Ribose 2'-O-methylation provides a molecular signature for the distinction of self and non-self mRNA dependent on the RNA sensor Mda5, Nature immunology, 2011, pp. 137-143, vol. 12.2.

\* cited by examiner

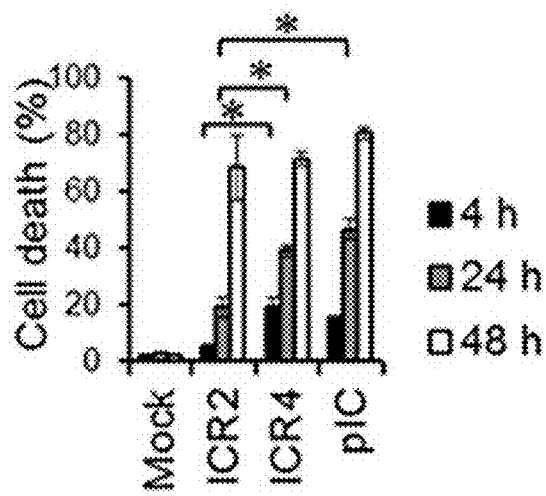
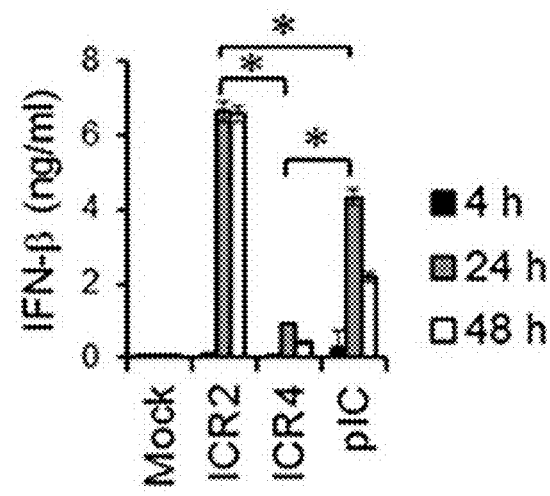
Fig. 3D          Fig. 3E
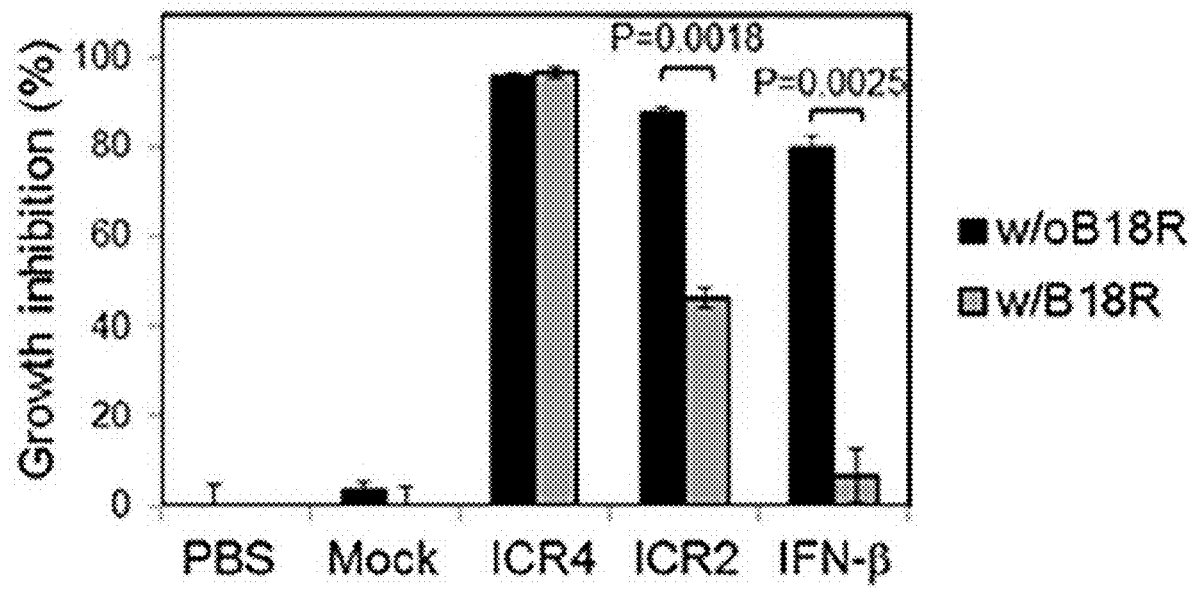
Fig. 3H

COMPOSITIONS AND METHODS FOR DIFFERENTIAL INDUCTION OF CELL DEATH AND INTERFERON EXPRESSION

CROSS-REFERENCE TO RELATED APPLICATIONS

This patent application is a national stage filing under 35 U.S.C. 371 of international Application No. PCT/US2018/025884, filed Apr. 3, 2018, which claims the benefit of priority of U.S. Provisional Patent Application No. 62/480,780, filed Apr. 3, 2017, both of which are incorporated herein by reference in their entirety.

REFERENCE TO A SEQUENCE LISTING

This application is being filed electronically via EFS-Web and includes an electronically submitted Sequence Listing in .txt format. The .txt file contains a sequence listing entitled "2018-04-03_5667-00429_ST25.txt" created on Apr. 3, 2018 and is 4,014 bytes in size. The Sequence Listing contained in this .txt file is part of the specification and is hereby incorporated by reference herein in its entirety.

FIELD OF INVENTION

The disclosed technology is generally directed to compositions and methods for the induction of cell death. More particularly the technology is directed to RNA compositions and their use for the induction of cell death and differential interferon expression.

BACKGROUND

Pattern-recognition receptors (PRRs) are immunological sensors that initiate the host defense response against infections. They are located at the cell surface, within endosomal compartments and in the cytoplasm, where they are poised to recognize different molecular signatures associated with invading pathogens.[1] Viral or bacterial RNAs are known to be potent ligands of multiple PRRs.[1] Retinoic acid inducible gene-I (RIG-I), melanoma differentiation associated gene-5 (MDA-5), RNA-activated protein kinase R (PKR), laboratory of genetics and physiology 2 (LGP2), Nacht leucine-rich repeat protein 3 (NALP3) and interferon-induced protein with tetratricopeptide repeats 1 (IFIT1) are located within the cytoplasm, where they sense specific molecular patterns within RNAs, e.g., 5' triphosphate (5'ppp), 5'diphosphate (5'pp) and double-stranded RNA (dsRNA).[2, 3] Toll-like receptors (TLRs) 3, 7 and 8 are localized to endosomal compartments and are activated by dsRNA (TLR3) and single-stranded RNA (ssRNA) (TLR7 and TLR8).[3]

In addition to anti-infectious immunity, the activation of RNA-sensing PRRs can mediate programmed cell death of infected cells, which allows the host to efficiently block viral replication by sacrificing infected cells.[4] PRR activation induces cell death not only in infected cells but also in non-infected, malignant cells. Transfection with synthetic viral dsRNA analogs, polyinosinic-polycytidylic acid (polyI:C) and short RNA duplex containing 5'ppp induces interferon (IFN)-β production and programmed cell death of various human cancer cells, including melanoma,[5] hepatocellular carcinoma,[6] glioblastoma,[7] prostate cancer,[8] ovarian cancer,[9] breast cancer[10] and pancreatic cancer[11] through activation of RNA-sensing PRRs. Interestingly, RNA-induced PRR activation upregulated pro-apoptotic molecules, e.g., Noxa, Puma and TRAIL in tumor cells but not in non-malignant cells, which may relate to the induction of tumor-selective cell death by PRR-activating RNAs.[5, 12]

Furthermore, PRR-mediated cell death engenders release of damage-associated molecular patterns (DAMPs) (e.g., high-mobility group box 1 protein (HMGB1)), surface translocation of calreticulin, antigen uptake and maturation of dendritic cell (DC), suggesting that RNA-induced tumor cell death is pro-immunogenic and can result in anti-tumor immunity.[11, 13, 14] Type I IFNs, e.g., IFN-α and IFN-β, have a wide range of immune stimulatory activities, including the augmentation of T helper type 1 cell responses, upregulation of MHC class I molecules, generation of natural killer (NK) cell- and T cell-mediated cytotoxicity and anti-tumor activities, including anti-proliferative, anti-angiogenic and pro-apoptotic effects.[15] Thus, PRR-mediated cell death and release of type I IFN can cooperatively and synergistically induce both therapeutic and prophylactic cellular immune responses against tumors.

Currently RNA-sensing PRR agonists have demonstrated little or no overall benefit to patients with cancers.[16, 17] This failure is due, in part, to toxicity driven by non-specific induction of immune reactions.[18] All PRR signaling culminates in the activation of MAP kinases, NF-κB and IFN regulatory factors (IRFs), which ultimately leads to the production of inflammatory cytokines and IFNs.[3] These cytokines and IFNs facilitate the induction of anti-tumor immune responses as well as cancer cell death; on the other hand, they can cause damage of normal tissues and organ failure.[15] Furthermore, the pro-inflammatory cytokines produced by tumor and tumor stroma cells promote tumor growth and survival and contribute to the deregulation of anti-tumor immunity,[19] which negatively impacts the therapeutic effects of anti-cancer PRR agonists. Therefore, the development of safe and effective RNA-sensing PRR agonists is necessary for these to become useful agents clinically.

Multiple RNA-sensing PRRs, including RIG-I,[5] MDA5,[20] TLR3[10] and TLR7,[21] have been shown to induce programmed cell death along with cytokine expression. It is still not clear how the activation of such RNA-sensing PRRs leads to cell death in cancer cells and whether PRR-mediated cell death and cytokine expression can be uncoupled. Recently, Yu et al demonstrated that a MDA5 mutant lacking N-terminal caspase-recruitment domains (CARDs) engaged a programmed cell death program in prostate cancer cells, but did not induce the expression of IFN-β.[22] However, no RNA agonists have been developed to differentially induce cell death and IFN and pro-inflammatory cytokine expression in cancer cells.

BRIEF SUMMARY OF THE INVENTION

Disclosed herein are compositions and methods for inhibiting the growth of cells or inducing cell death. In one aspect of the invention the composition capable of inhibiting the growth of cells or inducing cell death comprises a 5'-triphosphate non-linear RNA. The RNA may comprise a first stem-loop formed from the complete or partial hybridization of at least 8 nucleotide pairings. The RNA may also comprise a second stem-loop formed from the complete or partial hybridization of at least 8 nucleotide pairings and a spacer between the first stem-loop and the second stem loop. In some embodiments, the RNA may comprise one or more 2'-fluoromodified pyrimidines or other modifications such as one or more 2'-fluoromodified purines or phosphorothiolated nucleotides. In some embodiments, the first stem-loop comprises a 5'-triphosphate modified terminal nucleotide capable of hybridizing with its complement to form the first stem-loop and/or the second stem-loop comprises a 5'-triphosphate modified terminal nucleotide or a 3' terminal nucleotide capable of hybridizing with its complement to form the second stem-loop.

In some embodiments, the RNA comprises an oligonucleotide having at least 50%, including without limitation at least 80%, 85%, 90%, or 95%, sequence identity to ICR2 (SEQ ID NO: 8). In certain embodiments, the RNA comprises an oligonucleotide having at least 50% including without limitation at least 80%, 85%, 90%, or 95%, sequence identity to ICR4 (SEQ ID NO: 15), ICR4A (SEQ ID NO: 16), ICR5X (SEQ ID NO: 17), or ICR5Y (SEQ ID NO: 18). In particular embodiments, the RNA consists essentially of a ssRNA oligonucleotide having at least 50%, including without limitation at least 80%, 85%, 90%, or 95%, sequence identity to ICR4 (SEQ ID NO: 15) or ICR4A (SEQ ID NO: 16); or a dsRNA comprising a first oligonucleotide having at least 50%, including without limitation at least 80%, 85%, 90%, or 95%, sequence identity to ICR5X (SEQ ID NO: 17) completely or partially hybridized to a second oligonucleotide having at least 50%, including without limitation at least 80%, 85%, 90%, or 95%, sequence identity to ICR5Y (SEQ ID NO: 18).

In some embodiments, a stem-loop is formed from an oligonucleotide having at least 50%, including without limitation at least 80%, 85%, 90%, or 95%, sequence identity to ICR2 (SEQ ID NO: 8), the oligonucleotide comprising a 5'-triphosphate modified terminal nucleotide capable of hybridizing with its complementary nucleotide to form the stem-loop. In particular embodiment, the stem-loop is formed from an oligonucleotide consisting essentially of ICR2 (SEQ ID NO: 8).

In some embodiments, the spacer comprises a single-stranded segment of RNA. In particular embodiments the spacer comprises a third stem loop formed from the complete or partial hybridization of at least 8 nucleotide pairings. In other embodiments, the spacer comprises a double-stranded segment of RNA.

The composition may further comprise one or more therapeutic agents. The therapeutic agent may be selected from a chemotherapy agent, an anti-cancer biologic, an immunotherapy agent, or any combination thereof.

The composition may further comprise one or more cytoplasmic delivery compositions. The cytoplasmic delivery composition may be selected from a liposome, a synthetic polymer, a cell-penetrating peptide, a nanoparticle, a viral particle, a electroporation buffer, a nucleofection reagent, or any combination thereof.

Another aspect of the invention is pharmaceutical compositions comprising any of the compositions described above. The pharmaceutical composition may comprise a therapeutically effective amount of the composition capable of inhibiting growth of cells or inducing cell death and one or more pharmaceutically acceptable carriers, excipients, or diluents.

Another aspect of the invention is a method of inhibiting growth of cells or inducing cell death. The method may comprise contacting cells with any of the compositions described above capable of inhibiting growth of cells or inducing cell death in an amount effective to inhibit the growth of the cells or induce death of the cells.

Another aspect of the invention is a method of inhibiting growth of cells or inducing cell death in a subject. The method may comprise administering the composition as in any one of the preceding claims to the subject in need of such treatment in an amount effective to inhibit the growth of the cells or induce death of the cells.

In either of the methods described above, the cells may comprise cancer cells. The cancer cells may comprise melanoma, brain cancer, prostate cancer, breast cancer, renal cancer, lung cancer, liver cancer, colorectal cancer, leukemia, lymphoma, or ovarian cancer cells.

In either of the methods described above, the composition, or at least the RNA, is delivered into cytoplasm for at least a plurality of the cells.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 2A-FIG. 2D, culture supernatants were harvested at 24 hr after transfection. FIG. 2E, growth of human PBMCs was measured at 3 days after transfection using MTS assay. Data are the mean of three experiments. Error bars are S.D. *: $P<0.05$.

FIGS. 3A-3E show ICR4 and polyI:C induce acute cell death while ICR2 induced delayed cell death. WM266-4 cells ($2=10^5$ cells/well) were transfected for 4 h with ICR2, ICR4, polyI:C (1 µg/ml each) or transfection agent alone (Mock) in a 24-well plate. Cells and culture supernatants were harvested at 4 (FIG. 3A), 24 (FIG. 3B) and 48 (FIG. 3C) hr after transfection. Cell death was determined using Annexin V and 7-AAD staining (FIG. 3D). % Cell death=(% Annexin V+/7-AAD-)+(% Annexin V-/7-AAD+)+(% Annexin V+/7-AAD+). IFN-β production was determined by ELISA (FIG. 3E). FIGS. 3A-3C the data represents three individual experiments. FIGS. 3D-3E data are the mean of three experiments. Error bars are S.D. *: $P<0.05$.

FIGS. 3F-3H show ICR2 but not ICR4 induce IFN-dependent cell death. WM266-4 cells ($1\times10^4$ cells/well) were transfected for 4 h with ICR2, ICR4 (0.2 µg/ml each) or transfection agent alone (Mock) in a 96-well plate. Recombinant human IFN-β (100 ng/ml) was used as a positive control. Immediately after transfection, cells were cultured for 3 days in the presence or absence of B18R (1 µg/ml). Cytotoxicity was determined by Annexin V/7-AAD assay in the presence (FIG. 3F) or absence (FIG. 3G) of B18R (1 µg/ml) and MTS assay (FIG. 3H). FIGS. 3F-3G the data represents two individual experiments. FIG. 3H data are the mean of three experiments. Error bars are S.D. *: $P<0.05$.

(FIG. 3I) ICR2 and ICR2 antisense complementary to ICR2 were generated by T7 polymerase-induced IVT. ICR2-double strand was generated by hybridization of ICR2 and ICR2 antisense. RNAs were analyzed on 20% polyacrylamide gels. (FIG. 3J) Lower and (FIG. 3K) upper bands of ICR2 IVT were purified and transfected into human melanoma cell line WM266-4. Cell death levels were determined one day after transfection by Flow Cytometry-Based Annexin V-PE/7-AAD Staining Analysis.

(FIG. 4A) WM266-4 cells ($2\times10^5$ cells/well) were pre-incubated for 6 h with z-VAD-fmk, Nec-1, mixture of z-VAD-fmk and Nec-1 or DMSO, followed by transfected for 4 h with ICR2, ICR4 (0.2 µg/ml each) or transfection agent alone (Mock). Cells were cultured for 3 days in the presence of DMSO, z-VAD-fmk and/or Nec-1. Cell death was determined at 72 hr after transfection by Annexin V/7-AAD assay. (FIG. 4B-4C) WM266.4 cells were harvested at 24 h after transfection with ICR2, ICR4 or Mock. Total cell lysates, mitochondrial lysates and nuclear extracts were prepared and analyzed by Western blot. (FIG. 4B) expression of cell death associated molecules, including cleaved caspases 3 and 7, XIAP and TRAIL, in total cell lysates was assessed. β-tubulin expression was used as a loading control. (FIG. 4C) the expression of mitochondrial RIP1 and Cytochrome C oxidase IV (COX IV) in mitochondrial lysates, NF-κB p65 and histone H3 in nuclear extracts and phospho-IRF3 in total cell lysates was determined. Error bars represent the S.D. FIG. 4A data are the mean of three experiments. Error bars are S.D. FIG. 4B and FIG. 4C data represent two individual experiments. *$P<0.05$ (vs DMSO).

(FIG. 5A) Huh7.0 (RIG-I wildtype) and Huh7.5 (RIG-I mutant) cells ($7\times10^3$ cells/well) were transfected with ICR2, ICR4 (1 µg/ml each) or Mock in a 96-well plate. Cytotoxicity was determined at 3 days after transfection by MTS assay. (FIG. 5B) RIG-I, PKR and MDA5 in WM266-4 cells were knocked down three times with siRNAs. Cells ($1\times10^4$ cells/well) were re-plated in a 96-well plate and transfected with ICR2, ICR4 (0.2 µg/ml each) or Mock. Cytotoxicity was determined at 3 days after transfection by MTS assay. (FIG. 5C) Knockdown of RIG-I, MDA5 and PKR in human melanoma cells. siRNA-mediated knockdown efficiency was assessed 4 days after mock transfections (control) or siRNA (lacking 5'ppp) transfections by western blot using siRNA corresponding antibodies as indicated. β-Actin antibody was used as a loading control. (FIG. 5D) HEK-TLR3 and HEK-TLR7 reporter cells ($4\times10^4$ cells/well each) were transfected with ICR2, ICR4 or polyI:C (pIC) (0.5 µg/ml each). Non-transfected polyI:C (polyI:C) and R848 were used as positive controls for TLR3 and TLR7, respectively. PBS treatment was used as a negative control. ICR2 and ICR4 were dephosphorylated by treatment with a bacterial alkaline phosphatase (BAP) to investigate INF-β (FIG. 5E) and growth inhibition (FIG. 5F). The dephosphorylation was repeated twice. WM266-4 cells were transfected with BAP-treated and BAP-untreated ICR2 or ICR4 (30 nM each) or mock transfection. Cytotoxicity and IFN-β production was determined at 2 days after transfection. Error bar represent the S.D. *$P<0.05$.

(FIG. 5G) Cytotoxicity and (FIG. 5H) IFN-β production was assessed at 72 h post transfection. Error bars represent the S.D. *$P<0.05$.

(FIG. 6A) WM266-4 ($2\times10^5$ cells/well) cells were transfected with ICR2 or ICR4 (0.5 µg/ml each) in a 24-well plate and harvested at 24 h after transfection. Surface expression of Calreticulin was determined by flow cytometry. (FIG. 6B) uptakes of dead/dying WM266-4 cells treated with ICR2, ICR4 or Doxorubicin (Dox) by DCs were determined by phagocytosis assay. (FIG. 6C) secretion of nuclear protein HMGB1 from cells treated with ICR2, ICR4 or Dox was determined by ELISA. (FIG. 6D-6F) DAMPs were isolated from WM266-4 cells treated with transfection agent alone (Mock DAMP), ICR2 (ICR2 DAMP), ICR4 (ICR4 DAMP), polyI:C (pIC DAMP) or Doxorubicin (Dox DAMP) as described in the Methods. HEK-TLR2, HEK-TLR3, HEK-TLR4 and HEK-TLR9 reporter cells ($5\times10^4$ cells/well) were incubated with DAMPs (25% v/v). Activation of TLR 4 (FIG. 6D), TLR3 (FIG. 6E), TLR2 (FIG. 6F), and TLR9

(FIG. 6G) was determined by colorimetric assay. Pam3CSK4, non-transfected PolyI:C, LPS and CpG 2006 were used as positive controls of TLR reporter assays. FIGS. 6A-6B the data represent two individual experiments. FIGS. 6C-6G data are the mean of three experiments. Error bars are S.D. *P<0.05.

(FIGS. 7A-7B) Human melanoma WM266-4 cells ($7\times10^5$) were injected subcutaneously into a nude mouse. Tumor-bearing mice were intratumorally injected daily for 5 consecutive days with ICR2, ICR4 or polyI:C (pIC) (20 µg/mouse each) using in vivo-jetPEI (n=9). Tumor growth (FIG. 7A) was measured every other day and survival rate (FIG. 7B) was determined. (FIG. 7C) B16-F0 mouse melanoma cells ($2\times10^5$) were injected subcutaneously into a syngeneic C57BL/6 mouse. Either ICR4 or pIC (20 µg/mouse each) was administered intratumorally for 4 consecutive days (n=5), and survival rate (FIG. 7C) was determined. Error bar are S.D. *P<0.05 (vehicle vs ICR2, ICR4, pIC).

DETAILED DESCRIPTION OF THE INVENTION

Figure 1A:
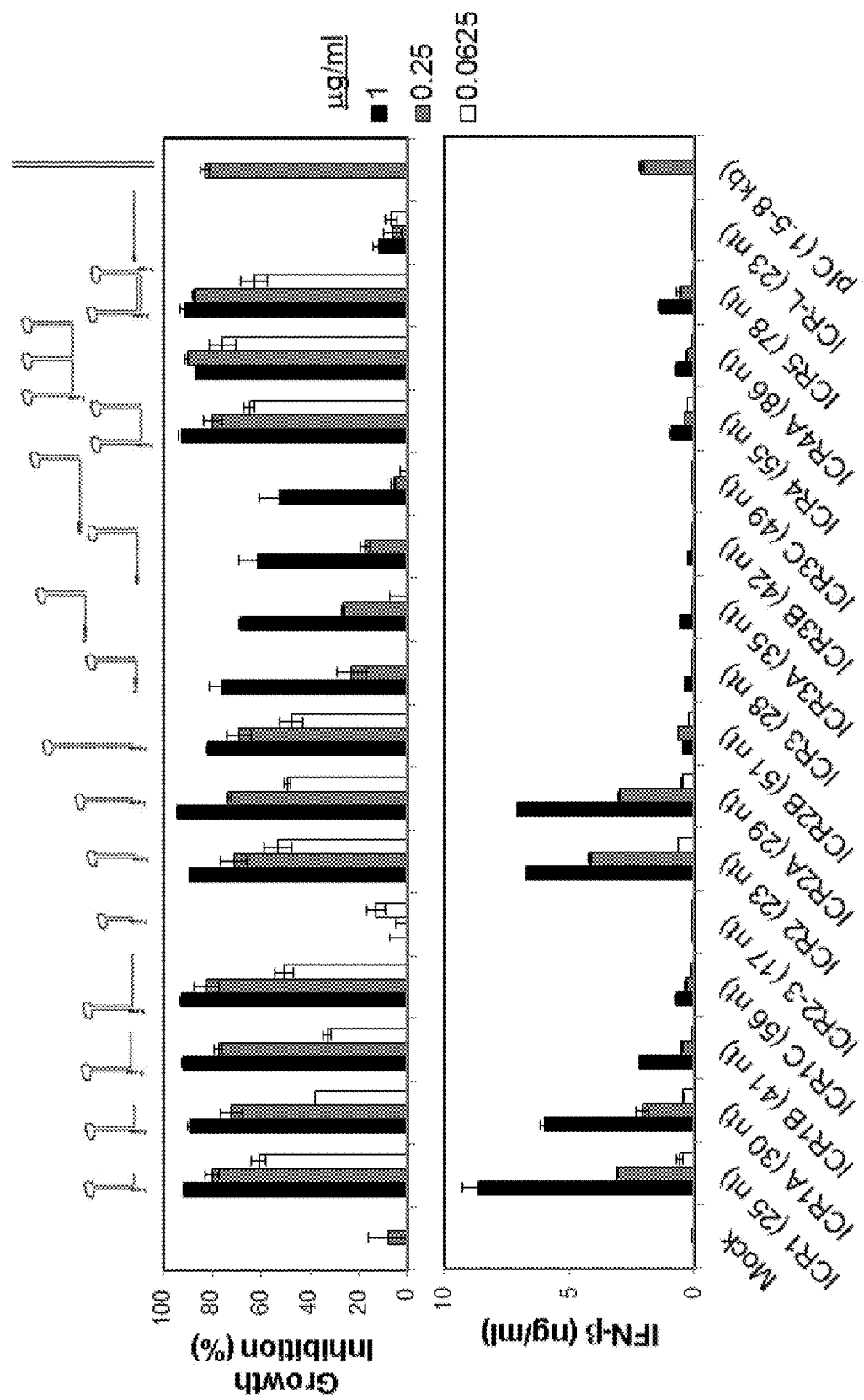
FIG. 1A illustrates differential induction of growth inhibition and IFN-β expression by 2'F-modified 5'ppp RNAs in a structure dependent manner. 2'F pyrimidine-incorporated 5'ppp RNAs were designed and generated to contain 5'ppp and various secondary structures including 3'-overhanged hairpin (ICR1 (SEQ ID NO: 1), ICR1A (SEQ ID NO: 2), ICR1B (SEQ ID NO: 3), ICR1C (SEQ ID NO: 4)), blunt-ended hairpin (ICR2-3 (SEQ ID NO: 5), ICR2 (SEQ ID NO: 8), ICR2A (SEQ ID NO: 9), ICR2B (SEQ ID NO: 10)), 5' overhanged hairpin (ICR3 (SEQ ID NO: 11), ICR3A (SEQ ID NO: 12), ICR3B (SEQ ID NO: 13), ICR3C (SEQ ID NO: 14)) and multiple stem-loops (ICR4 (SEQ ID NO: 15), ICR4A (SEQ ID NO: 16), ICR5 (SEQ ID NOS: 17 and 18)) at various length. Linear 5'ppp ssRNA (ICR-L (SEQ ID NO: 19)) and long dsRNA (pIC) were also generated. The RNA secondary structure was predicted using mFold. To treat cancer cells with these RNAs, WM266.4 human melanoma cells ($1\times10^4$ cells/well) were transfected for 4 h with the indicated concentrations of RNAs in a 96-well plate. At 72 hr after RNA treatment, cells and culture supernatants were harvested and analyzed for growth inhibition and IFN-β expression, respectively. The data represent two individual experiments. Error bars are S.D.

Disclosed herein are multiple nuclease-resistant RNA molecules that can differentially induce immunogenic cancer cell death with or without concomitant expression of pro-inflammatory cytokines, including INF-β, TNF-α, or IL-6. The compositions include a 5' triphosphate, 2' fluoro-modified pyrimidine non-linear single-stranded RNA (ssRNA) or double-stranded RNA (dsRNA). As demonstrated in the Examples that follow, the compositions elicit potent cytotoxicity. In some cases, the compositions also induce a substantial amount of type I IFN production. In other cases, however, the compositions do not induce a substantial amount of cytokine production. Thus the compositions disclosed herein provide for potent cytotoxicity but differential induction of cytokine production.

The RNA compositions described herein share the common structural motif of a stem-loop. RNA compositions comprising multiple stem loops demonstrated some of the highest levels of cytotoxicity or growth inhibition at the lowest concentrations tested without substantial induction of cytokine production. Although some of the RNA compositions with a single stem-loop demonstrate substantial cytotoxicity or growth inhibition without substantial induction of cytokine production, those single-stemmed compositions tended to demonstrate lower cytotoxicity or growth inhibition or greater cytokine production at comparable concentrations to the multi-stemmed compositions. In some cases, the single-stemmed compositions demonstrate lower cytotoxicity or growth inhibition or greater IFN production at comparable concentrations.

Cytokines are immunomodulating agents comprising an array of proteins such as interferons, interleukins, tumor necrosis factors, chemokines, and lymphokines. As demonstrated in the Examples that follow the RNA compositions may differentially induce the production of cytokines such as INF-β, TNF-α, or IL-6.

Stem-loops are formed from the complete or partial hybridization of nucleotides and result in hair-pin structural motifs. The stem-loop may be formed from any suitable number of nucleotide pairings, including any number of nucleotide pairings between about 5 and about 30 or about 8 to about 25. In certain embodiments, the stem-loop comprises 5, 6, 7, 8, 9, 10, 11, 12, 13, 14, 15, 16, 17, 18, 19, 20, 21, 22, 23, 24, 25, 26, 27, 28, 29, or 30 nucleotide pairings or any number of nucleotide pairings therebetween. Stem-loops having only partial hybridization may have any number of nucleotide-pair mismatches that prevent nucleotide pairing between complementary nucleotides along the stem. Preferably, the stem-loop remains stable under physiological conditions. In some cases, the stem-loop has 1, 2, 3, 4, or 5 nucleotide-pair mismatches or any range of nucleotide-pair mismatches therebetween. The mismatches within the stem may be called a bulge in the stem-loop. As used herein, stable may be thermodynamic stability or kinetic stability.

The RNA compositions may comprise a 5'-end modification. The 5'-end modification may comprise a 5'-triphosphate. Where the RNA composition comprises dsRNA, one or both of the 5'-ends may be modified to comprise a 5'-triphosphate.

The RNA compositions may comprise 2'-fluoro modified pyrimidines or 2'-fluoro modified purines. The 2'-fluoro modification may be present on at least one pyrimidine or purine, and may be present on any number of pyrimidines or purines, including all of the pyrimidines, all of the purines, or all of the pyrimidines and purines. Suitably the 2'-fluoro-modification is present in 10%, 20%, 30%, 40%, 50%, 60%, 70%, 80%, 90% or 100% of the pyrimidines and/or purines or any range therebetween. The 2-fluoro modification may be present on a uridine, a cytidine, a guanine, an adenine, or any combination thereof. In some embodiments, only uridines are 2'-fluoro modified. In an embodiment, all of the uridines in the RNA are 2'-fluoro-modified, all of the cytidines in the RNA are 2'-fluoro-modified, all of the guanines in the RNA are 2'-fluoro-modified, all of the adenines in the RNA are 2'-fluoro-modified, or any combination thereof.

The RNA compositions may comprise phosphorothioate modified nucleotides where a sulfur atom is substituted for a non-bridging oxygen of the phosphate. Suitably the phosphorothioate modification is present in 10%, 20%, 30%, 40%, 50%, 60%, 70%, 80%, 90% or 100% of the nucleotides or any range therebetween. In certain embodiments, the last 3 to 5 nucleotides at the 5'- and/or 3'-end of the oligonucleotide are phosphorothioate modified. In other embodiments, all of the nucleotides of the oligonucleotide are phosphorothioate modified.

The RNA compositions may comprise a blunt-end stem loop, a stem-loop having a 5'-overhang, a stem-loop having a 3'-overhang, or both a 5'-overhang and a 3'-overhang. Blunt-end stem loops comprise a 5'-terminal nucleotide and its 3'-terminal complement that are capable of hybridizing with each other, forming the stem-loop. Stem-loops having only a 5'-overhang comprise a 3'-terminal nucleotide capable of hybridizing with its complement to form the stem loop. Stem-loops having only a 3'-overhang comprise a 5'-terminal nucleotide capable of hybridizing with its complement to form the stem loop. For stem-loops having both a 5'-overhang and a 3'-overhang, neither the 5'-terminal nucleotide nor the 3'-terminal nucleotide form a part of the stem-loop.

A 5'- or 3'-overhang may be any length that allows for the RNA composition to inhibit cell growth or induce cell death. Suitably, the 5'- and/or 3'-overhang may be about 1 to about 50 nucleotides in length. In some embodiments, the 5'- and/or 3'-overhang is about 1 to about 10 nucleotides in length, including lengths of 1, 2, 3, 4, 5, 6, 7, 8, 9, or 10 nucleotides or any range of lengths therebetween. In other cases, the 5'- and/or 3'-overhang is about 10 to about 50 nucleotides in length, including lengths of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides or any range of lengths therebetween. Those of skill in the art will be able to select an appropriate overhang length to result in desired activity. As the Examples show, RNA compositions comprising shorter overhangs, especially 3'-overhangs, are more likely to demonstrate an ability to inhibit cell growth or induce cell death and induce cytokine production. In contrast, RNA compositions comprising longer overhangs are more likely to demonstrate an ability to inhibit cell growth or induce cell death without inducing cytokine production.

In certain embodiments, the RNA composition comprises multiple stem-loops. As shown in the Examples that follow, RNA compositions comprising two or three stem-loops are surprisingly effective in inhibiting growth of cells or inducing cell death without also inducing substantial IFN production. RNA compositions having multiple stem-loops minimally comprise a first stem-loop, a second stem-loop, and a spacer between the stem-loops. The stem-loops may be the same, but need not be as shown in the Examples.

The RNA composition may comprise a nucleotide sequence allowing for a terminal nucleotide to hybridize with it complement to form either the first stem-loop, the second stem-loop, or both. In some embodiments, the RNA composition comprises a 5'-triphosphate modified terminal nucleotide capable of hybridizing with its complementary nucleotide to form either the first or second stem-loop. In some embodiments, the RNA composition comprises a 3'-terminal nucleotide capable of hybridizing with its complementary nucleotide to form either stem-loop. As shown in the Examples, the RNA compositions may comprise a 5'-triphosphate modified terminal nucleotide capable of hybridizing with its complementary nucleotide to form a first stem-loop and a 3'-terminal nucleotide capable of hybridizing with its complementary nucleotide to form a second stem-loop. As also shown in the Examples, the RNA compositions may be double stranded and comprise a 5'-triphosphate modified terminal nucleotide capable of hybridizing with its complementary nucleotide to form a first stem-loop and a 5'-triphosphate modified terminal nucleotide capable of hybridizing with its complementary nucleotide to form a second stem-loop.

The RNA composition may comprise a 5'- or 3'-overhang associated with either or both of the first stem-loop and the second stem-loop. The 5'- or 3'-overhang associated with either the first stem-loop or the second stem-loop may be any length that allows for the RNA composition to inhibit cell growth or induce cell death. Suitably, the 5'- and/or 3'-overhang may be about 1 to about 50 nucleotides in length. In some embodiments, the 5'- and/or 3'-overhang is about 1 to about 10 nucleotides in length, including lengths of 1, 2, 3, 4, 5, 6, 7, 8, 9, of 10 nucleotides or any range of lengths therebetween. In other cases, the 5'- and/or 3'-overhang is about 10 to about 50 nucleotides in length, including lengths of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides or any range of lengths therebetween. Those of skill in the art will be able to select an appropriate overhang length to result in desired activity.

The spacer connects the stem loops in a multi-stem loop composition. In some embodiments, the spacer comprises a segment of ssRNA, a segment of dsRNA, or a combination thereof. A dsRNA segment may comprise a completely or partially hybridized segment of a segment of a first nucleotide sequence with a second nucleotide sequence. Spacers having only partial hybridization may have any number of nucleotide-pair mismatches that prevent nucleotide pairing between complementary nucleotides along the spacer. Preferably, the spacer remains thermodynamically or kinetically stable under physiological conditions. In some cases, the stem-loop has 1, 2, 3, 4, 5, or more nucleotide-pair mismatches.

The spacer may be any suitable length to provide the benefit of cytotoxicity without substantially inducing IFN production. Suitably, the length of the spacer may include between about 5 to about 100 nucleotides along a ssRNA segment, about 5 to about 100 hybridized or mismatched nucleotide pairs along a dsRNA segment, or a combination thereof. In some embodiments, the length of the spacer is about 5 to about 50 nucleotides, including lengths of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides or any range of lengths therebetween.

In some embodiments, the spacer is not associated with secondary structure. In other embodiments, the spacer is associated with secondary structure. Structured spacers may comprise a stem-loop, resulting in RNA compositions comprising at least a third stem-loop. The third stem-loops may be formed from the complete or partial hybridization of nucleotides and result in a hair-pin structural motif. The stem-loop may be formed from any suitable number of nucleotide pairings, including any number of nucleotide pairings between about 5 and about 30 or about 8 to about 25. In certain embodiments, the stem-loop comprises 5, 6, 7, 8, 9, 10, 11, 12, 13, 14, 15, 16, 17, 18, 19, 20, 21, 22, 23, 24, 25, 26, 27, 28, 29, or 30 nucleotide pairings or any number of nucleotide pairings therebetween. Stem-loops having only partial hybridization may have any number of nucleotide-pair mismatches that prevent nucleotide pairing between complementary nucleotides along the stem so long as the stem-loop remains stable under physiological conditions. In some cases, the stem-loop has 1, 2, 3, 4, or 5 nucleotide-pair mismatches or any range of nucleotide-pair mismatches therebetween.

Exemplary RNA oligonucleotides are provided in Table 1. The RNA compositions, referred to as Immunogenic Cancer cell-killing RNAs (ICRs), comprising 2'F pyrimidine-incorporated 5'ppp RNAs were designed and generated to contain 5'ppp and various predicted secondary structures including 3'-overhanged hairpin (ICR1, ICR1A, ICR1B, ICR1C), blunt-ended hairpin (ICR2-3, ICR2, ICR2A, ICR2B), 5' overhanged hairpin (ICR3, ICR3A, ICR3B, ICR3C), ssRNA comprising multiple stem-loops (ICR4, ICR4A) and dsRNA comprising multiple stem-loops (ICR5, which is formed from the hybridization of ICR5X and ICR5Y) at various lengths. Linear 5'ppp ssRNA (ICR-L) and long dsRNA (pIC) were also generated for comparison. As will be apparent to those of skill in the art, each of ICR1, ICR1A, ICR1B, ICR1C, ICR2A, ICR2B, ICR3, ICR3A, ICR3B, ICR3C, ICR4, ICR4A, ICR5X, and ICR5Y comprise the oligonucleotide sequence of ICR2.

TABLE 1

Single-stranded RNA

| RNA | Sequence (5'→3') | SEQ ID NO |
|---|---|---|
| ICR1 | ggaug cggua ccuga cagca uccua | SEQ ID NO: 1 |
| ICR1A | ggaug cggua ccuga cagca uccua aagug | SEQ ID NO: 2 |
| ICR1B | ggaug cggua ccuga cagca uccua aagug gugga aguga g | SEQ ID NO: 3 |
| ICR1C | ggaug cggua ccuga cagca uccua aagug gugga aguga gugag ugaaa uaaaa a | SEQ ID NO: 4 |
| ICR2-3 | ggacg uaccu gacgu cc | SEQ ID NO: 5 |
| ICR2-2 | ggauc guacc ugacg aucc | SEQ ID NO: 6 |
| ICR2-1 | ggauc gguac cugac agauc c | SEQ ID NO: 7 |
| ICR2 | ggaug cggua ccuga cagca ucc | SEQ ID NO: 8 |
| ICR2A | ggacg augcg guacc ugaca gcauc gucc | SEQ ID NO: 9 |
| ICR2B | ggaug cggua ccuga cagca uccac cuggg augcu gucag guacc gcauc c | SEQ ID NO: 10 |
| ICR3 | ggagc ggaug cggua ccuga cagca ucc | SEQ ID NO: 11 |
| ICR3A | gggga ggaca gcgga ugcgg uaccu gacag caucc | SEQ ID NO: 12 |
| ICR3B | ggaau gaggg gagga cagcg gaugc gguac cugac agcau cc | SEQ ID NO: 13 |
| ICR3C | gggua aguga augag gggag gacag cggau gcggu accug acagc aucc | SEQ ID NO: 14 |
| ICR4 | ggaug cggua ccuga cagca uccua aacuc auggu ccaug uuugu ccaug gacca | SEQ ID NO: 15 |
| ICR4A | ggaug cggua ccuga cagca uccua aacuc auggu ccaug uuugu ccaug gacca acuac cgaca uugua ugugu ugaua uaaug u | SEQ ID NO: 16 |
| ICR5X | ggaug cggua ccuga cagca uccug aguuu aguug uugu | SEQ ID NO: 17 |
| ICR5Y | ggaug cggua ccuga cagca uccac aacaa cuaaa cuca | SEQ ID NO: 18 |
| ICR-L | gguuu uuuuu uuuuu uuuuu uuu | SEQ ID NO: 19 |

In some embodiments, the RNA composition comprises an oligonucleotide capable of forming a stem-loop. In some embodiments, the RNA composition comprises one or more stem-loops formed from the complete or partial hybridization of an oligonucleotide having at least 50% sequence identity to ICR2. In particular embodiments, the RNA composition comprises one or more stem-loops formed from the complete or partial hybridization of an oligonucleotide having at least 60%, 70%, 80%, 81%, 82%, 83%, 84%, 85%, 86%, 87%, 88%, 89%, 90%, 91%, 92,%, 93%, 94%, 95%, 96%, 97%, 98%, 99%, or 100% sequence identity to ICR2. The RNA composition may also consist essentially of one or more stem-loops formed from the complete or partial hybridization of an oligonucleotide having at least 50%, 60%, 70%, 80%, 81%, 82%, 83%, 84%, 85%, 86%, 87%, 88%, 89%, 90%, 91%, 92,%, 93%, 94%, 95%, 96%, 97%, 98%, 99%, or 100% sequence identity to ICR2.

In some embodiments, the RNA composition comprises one or more oligonucleotides having at least 50% sequence identity to ICR1, ICR1A, ICR1B, ICR1C, ICR2A, ICR2B, ICR3, ICR3A, ICR3B, ICR3C, ICR4, ICR4A, ICR5X, or ICR5Y. In particular embodiments, the RNA composition comprises one or more oligonucleotides having at least 60%, 70%, 80%, 81%, 82%, 83%, 84%, 85%, 86%, 87%, 88%, 89%, 90%, 91%, 92,%, 93%, 94%, 95%, 96%, 97%, 98%, 99%, or 100% sequence identity to any ICR1, ICR1A, ICR1B, ICR1C, ICR2A, ICR2B, ICR3, ICR3A, ICR3B, ICR3C, ICR4, ICR4A, ICR5X, or ICR5Y. The RNA composition may also consist essentially of one or more oligonucleotides having at least 50%, 60%, 70%, 80%, 81%, 82%, 83%, 84%, 85%, 86%, 87%, 88%, 89%, 90%, 91%, 92,%, 93%, 94%, 95%, 96%, 97%, 98%, 99%, or 100% sequence identity to any of ICR1, ICR1A, ICR1B, ICR1C, ICR2A, ICR2B, ICR3, ICR3A, ICR3B, ICR3C, ICR4, ICR4A, ICR5X, or ICR5Y.

As show in Example 1, the ICRs demonstrated dose-dependent cytotoxicity except for the linear ICRs and the ICR containing the shortest stem loop. For those ICRs demonstrating cytotoxicity, cytokine expression was differentially induced. ICRs with a blunt end on a 9-12 bp long stem loop induced 2 to 3-fold higher production of IFN-β by human melanoma cells than polyI:C, the length of 5' and 3' overhangs and the number and length of stem loops were inversely correlated with IFN-β expression.

As used herein, the RNA composition that induces a substantial or significant amount of cytokine if it induces the production of at least as much cytokine as a polyI:C under the same conditions or, alternatively, cytokine production is increased 5, 6, 7, 8, 9, 10 or more fold as compared to the production of IFN in untreated control cells. In some cases, the measured cytokine is INF-β, TNF-α, or IL-6.

PRR-induced cancer cell death accompanies release of multiple immune and hemostatic modulators, e.g., IFNs, inflammatory cytokines, DAMPs, that orchestrate to stimulate innate and adaptive immune responses against cancer and also, potentially, cause destructive inflammatory responses against normal tissues and thrombotic complications. It has long been asked how the dichotomous responses generated by PRR-induced cancer cell death are favorably modified to enhance anti-cancer therapeutic effects and overall benefits of PRR therapeutics. As demonstrated below, both ICR2 and ICR4 are novel PRR-stimulating ssRNAs that provoke strong immunogenic cell death of human cancer cells and significantly reduced TNF-α production by human cancer and immune cells compared with polyI:C. ICR2 induces IFN-dependent necropsis of human cancer cells and much higher amounts of type I IFN than ICR4. In contrast, ICR4 induces RIG-I-dependent apoptotic cell death and generated significantly less inflammatory and less coagulative DAMPs than ICR2.

It has been thought that a physiological cell death such as apoptosis is poorly immunogenic or tolerogenic, whereas a pathological death such as necrosis is immunogenic.[32] However, it has also been shown that certain apoptotic agents, e.g., doxorubicin, induced more immunogenic cancer cell death than necrotic agents.[34, 38] It is still unclear how the immune system differentially responds to different cancer cell death. Although types of TLRs stimulated by ICR4-generated DAMPs were similar to those stimulated by ICR2- and polyI:C-generated DAMPs, the signal strength of TLRs stimulated by ICR4-generated DAMPs was significantly lower than that of TLRs stimulated by ICR2- and polyI:C-generated DAMPs. Consistent with TLR signal strength, ICR4-induced cell death released significantly less amounts of endogenous TLR4 ligand HMGB1 than did ICR2- and polyI:C-induced cell death.

The levels of DAMPs are not always directly correlated with the immunogenicity and TLR stimulatory activity of cell death. Both ICR4 and doxorubicin induced apoptotic cancer cell death, and they produced comparable amounts of HMGB1 release. However, TLR4 reporter cells were stimulated by ICR4-generated DAMPs but not by doxorubicin-generated DAMPs. Depending on the oxidative state, HMGB1 was shown to differentially induce innate and inflammatory responses.[39] Reduced HMGB1 is able to stimulate TLR4 and has immune stimulatory activity, but oxidized HMGB1 does not stimulate TLR4 and has tolerogenic activity.[39, 40] These data suggest that different types of cell death may generate quantitatively and qualitatively different DAMPs and lead to different TLR stimulation and different immune responses.

Kohlway et al demonstrated that 5'ppp RNA hairpin with duplex length of 10 bp effectively stimulated RIG-I ATPase activity in vitro, and transfection with this RNA hairpin induced IFN-β production by a RIG-I-expressing 293T cell line.[24] The ICR2 is a 2'F-modified 5'ppp RNA hairpin with duplex length of 9 bp. The secondary structure of ICR2 is very similar to Kohlway's RNA hairpin. However, ICR2 does not contain known RIG-I stimulating motifs, e.g., U/UC,[41] whereas Kohlway's RNA has a U/UC motif. We demonstrated that treatment with ICR2 showed comparable cytotoxicity to both Huh7.0 and RIG-I-deficient Huh7.5 cell lines. Furthermore, ICR2-induced cancer cell death and IFN-β expression was not significantly affected by the deficiency of individual RIG-I, MDA5 and PKR. Without wishing to be bound by theory, one possibility is that ICR2 may be recognized by other RNA-sensing PRRs. For example, TLR13 is an endosomal TLR whose functions and ligands remain poorly understood. A recent study has demonstrated that a viral-derived 16-nt ssRNA predicted to form a stem-loop structure stimulated mouse TLR13.[42] Human TLR13 gene and its anti-cancer activities have not been elucidated yet. Nucleotide-binding oligomerization domain 2 (NOD2) is another cytoplasmic PRR that recognizes bacterial peptidoglycan as well as viral ssRNAs.[43] NOD2 triggers activation of IRF3 and expression of IFN-β in human and mouse cells.[44] Furthermore, IFIT1 selectively binds to 5'ppp RNA in a sequence-independent manner and induce anti-viral responses.[2] Another possibility is that multiple RNA-sensing PRRs may simultaneously recognize ICR2 and play compensatory roles in ICR2-induced IFN-β expression and cell death.

The RNA compositions described herein may be combined with one or more therapeutic agents. The therapeutic agent may be an anti-cancer therapeutic agent used to treat cancer in a subject. Suitable anti-cancer therapeutic agents may include, without limitation, radiation, chemotherapy agents, anti-cancer biologics, or immunotherapy agents.

Chemotherapy agents are chemotherapeutic compounds that may be used to treat cancer. Suitable chemotherapy agents may include, without limitation, 5-fluorouracil, aclacinomycin, activated cytoxan, bisantrene, bleomycin, carmofur, CCNU, cis-platinum, daunorubicin, doxorubicin, DTIC, melphalan, methotrexate, mithromycin, mitomycin, mitomycin C, peplomycin pipobroman, plicamycin, procarbazine, retinoic acid, tamoxifen, taxol, tegafur, VP16, or VM25.

Anti-cancer biologics are biomolecules (e.g., polynucleotides, polypeptides, lipids, or carbohydrates) that may be used to treat cancer. Anti-cancer biologics may include, without limitation, cytokines such as IL-1α, IL-2, IL-2β, IL-3, IL-4, CTLA-2, IFN-α, IFN-γ, granulocyte-macrophage colony stimulating factor (GM-CSF), IL-12, IL-23, IL-15, IL-7, or any combination thereof; or anti-cancer antibodies such as Rituximab, Trastuzumab, Gemtuzumab, Alemtuzumab, Ibritumomab tiuxetan, Tositumomab, Cetuximab, Bevacizumab, Panitumumab, Ofatumumab, Brentuximab Vedotin, Pertuzumab, Adotrastuzumab emtansine, and Obinutuzumab.

The term "immunotherapy agent(s)" refers to any therapeutic that is used to treat cancer in a subject by inducing and/or enhancing an immune response in that subject. Immunotherapy agents may include, without limitation, checkpoint inhibitors, cancer vaccines, immune cells such as engineered T cells, anti-cancer viruses, or bispecific antibodies. Checkpoint inhibitors are therapeutics, such as antibodies, that block the immune checkpoint pathways in immune cells that are responsible for maintaining self-tolerance and modulating the degree of an immune response. Tumors often exploit certain immune checkpoint pathways as a major mechanism of immune resistance against T cells that are specific for tumor antigens. Many of the immune checkpoints are initiated by receptor-ligand interactions and thus may be blocked by antibodies to either the ligand or receptor or may be modulated by soluble recombinant forms of the ligands or receptors. Such immune checkpoint blockade allows tumor-specific T cells to continue to function in an otherwise immunosuppressive tumor microenvironment.

Exemplary checkpoint inhibitors include, without limitation, antibodies or other therapeutics targeting programmed cell death protein 1 (PD1, also known as CD279), programmed cell death 1 ligand 1 (PD-L1, also known as CD274), PD-L2, cytotoxic T-lymphocyte antigen 4 (CTLA4, also known as CD152), A2AR, CD27, CD28, CD40, CD80, CD86, CD122, CD137, OX40, GITR, ICOS, TIM-3, LAG3, B7-H3, B7-H4, BTLA, IDO, KIR, or VISTA. Suitable anti-PD1 antibodies include, without limitation, lambrolizumab (Merck MK-3475), nivolumab (Bristol-Myers Squibb BMS-936558), AMP-224 (Merck), and pidilizumab (CureTech CT-011). Suitable anti-PD-L1 antibodies include, without limitation, MDX-1105 (Medarex), MEDI4736 (Medimmune) MPDL3280A (Genentech/Roche) and BMS-936559 (Bristol-Myers Squibb). Exemplary anti-CTLA4 antibodies include, without limitation, ipilimumab (Bristol-Myers Squibb) and tremelimumab (Pfizer).

A recent study has demonstrated that combination of immunogenic cell death-inducing cancer therapeutics and checkpoint inhibitors, e.g., anti-CTLA4 and anti-PD-L1, synergistically enhanced anti-tumor response and anti-tumor immunity.[45] ICR2 and ICR4 are potent PRR-stimulating cytotoxic agents against human cancers. ICR2 and ICR4 have distinctive immune stimulatory and hemostatic activities. Combination of checkpoint inhibitors and the RNA compositions described herein would be a potent and effective anti-cancer therapy against advanced cancers.

Cancer vaccines stimulate the body's immune system to attack cancer cells. Cancer vaccines generally include a tumor antigen in an immunogenic formulation that activates tumor antigen-specific helper T cells and/or cytotoxic T cells and B cells. Vaccines can be in a variety of formulations, including, without limitation, dendritic cells, monocytes, viral, liposomal and DNA vaccines. Exemplary cancer vaccines include, without limitation, Sipuleucel-T (Provenge®, or APC8015). Sipuleucel-T is an FDA-approved cancer vaccine developed from autologous dendritic cells (DC) loaded with engineered fusion protein of prostatic acid phosphatase (PAP) and granulocyte-macrophage colony-stimulating factor (GM-CSF).

An immunotherapy agent may include immune cells (i.e., T cells or B cells) that are adoptively transferred into a subject to attack or reduce cancer cells or cancer cell growth. The immune cells may be autologous or derived from a subject that is different from the subject receiving the immune cells and modified to reduce rejection. The immune cells may also have a natural or genetically engineered reactivity to a subject's cancer. For example, natural autologous T cells have been shown to be effective in treating metastatic cancers. See, e.g., Rosenberg S A et al., *Nat. Rev. Cancer* 8 (4): 299-308 (2008). Natural autologous T cells may be found within a resected subject's tumor. Such T cells can be induced to multiply in vitro using high concentrations of IL-2, anti-CD3 and allo-reactive feeder cells. These T cells are then transferred back into the subject along with, for example, exogenous administration of IL-2 to further boost their anti-cancer activity.

The compositions described herein may also include a cytoplasmic delivery mechanism. Such delivery mechanisms are available to those skilled in the art and include all gene delivery mechanisms including but not limited to synthetic polymers (such as those used for siRNA delivery), cell-penetrating peptides (such as VP16), nanoparticles, viral or liposomal delivery to the cytoplasm of cells (lipofection), delivery via a gene gun, or may include transfection, nucleofection or electroporation. The cytoplasmic delivery mechanisms may be targeted to only deliver the compositions to cells in which cell growth inhibition or induction of programmed cell death is desired. For example, the cellular delivery mechanism may specifically target the RNAs to cancer cells or virally infected cells. The compositions may be targeted to cells for uptake by receptor-mediated endocytosis as well. In addition, cells could be genetically engineered to express the RNA compositions described herein. The RNAs could be operably connected to a promoter, such as an inducible promoter, to allow expression of the RNA only upon proper stimulation.

The compositions described herein may also be used to inhibit cancer cell growth or induce programmed cell death of cancer cells which may result in treating cancer in a subject. The compositions may also be useful in treating other non-cancerous proliferative disorders or in treating infected cells, such as cells infected with a virus or other intracellular pathogen. The compositions provided herein may also be administered as an adjuvant to stimulate an immune response to an antigen, pathogen or cancer cell. Subjects that may be administered the compositions described herein include, but are not limited to mammals, domesticated animals and humans and may specifically include dogs, cats, fish, chickens, cows, pigs, sheep, goats.

Along these lines, methods of inhibiting the growth of cells or inducing programmed cell death using the compositions comprising the ssRNAs or dsRNAs described herein are also provided. The methods include contacting cells with the compositions or alternatively administering the compositions to subjects in an amount effective to inhibit the growth of cells, induce programmed cell death of cells or increase inflammatory cytokine production by cells. The cells may be melanoma cells, or other cancer cells, including but not limited to brain, prostate, ovarian, renal, lung, liver, colorectal and breast cancer cells or leukemia or lymphoma cells.

Suitably, the composition is delivered to the cytoplasm of the cell. The compositions may be delivered through the cytoplasmic delivery mechanisms described above and include but are not limited to liposomes, synthetic polymers, cell penetrating peptides, nanoparticles, viral encapsulation, receptor-mediated endocytosis, electroporation or any other means to deliver the composition to the cytoplasm of the cells.

Cells may be contacted with the composition directly or indirectly in vivo, in vitro, or ex vivo. Contacting encompasses administration to a cell, tissue, mammal, patient, or human. Further, contacting a cell includes adding the composition to a cell culture with a cytoplasmic delivery mechanism or introducing the composition into the cytoplasm of the cell via any available means. Other suitable methods may include introducing or administering the composition to a cell, tissue, mammal, or patient using appropriate procedures and routes of administration as defined below.

Administration of the compositions described herein may inhibit the growth of cancer cells or treat cancer. This effect may be due to a general immunostimulatory effect of administration of the compositions or by programmed cell death initiated by contact with the compositions. The administration of the compositions described herein may inhibit the growth of the cells by 20%, 30%, 40%, 50%, 60%, 65%, 70%, 75%, 80% or more as compared to control treated cells. The administration of the compositions described herein may also induce cell death, suitably programmed cell death in 5%, 10%, 15%, 20%, 25%, 30%, 35%, 40%, 45%, 50%, 55%, 60%, 65%, 70% or more than 75% of the treated cells. Programmed cell death includes any means of cell death mediated by an intracellular program and includes, but is not limited to apoptosis, autophagy, necroptosis, anoikis, or other non-apoptotic forms of programmed cell death.

The compositions described herein may be administered to a subject to treat cancer in the subject. Treating cancer includes, but is not limited to, reducing the number of cancer cells or the size of a tumor in the subject, reducing progression of a cancer to a more aggressive form, reducing proliferation of cancer cells (inhibiting the growth of) or reducing the speed of tumor growth, killing of cancer cells (via any means), reducing metastasis of cancer cells or reducing the likelihood of recurrence of a cancer in a subject. Treating a subject as used herein refers to any type of treatment that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc.

The compositions may be used to make pharmaceutical compositions. Pharmaceutical compositions comprising the RNAs and compositions described above and a pharmaceutically acceptable carrier are provided. A pharmaceutically acceptable carrier is any carrier suitable for in vivo administration. Examples of pharmaceutically acceptable carriers suitable for use in the composition include, but are not limited to, water, buffered solutions, glucose solutions, oil-nucleotided or bacterial culture fluids. Additional components of the compositions may suitably include, for example, excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The composition may also be emulsified.

An effective amount or a therapeutically effective amount as used herein means the amount of the composition that, when administered to a subject for treating a state, disorder or condition, such as cancer, is sufficient to effect a treatment (as defined above). The therapeutically effective amount will vary depending on the composition, the disease and its severity and the age, weight, physical condition and responsiveness of the subject to be treated.

The compositions described herein may be administered by any means known to those skilled in the art, including, but not limited to, oral, topical, intranasal, intraperitoneal, parenteral, intravenous, intracranial, intratumoral, intramuscular, subcutaneous, intrathecal, transcutaneous, nasopharyngeal, or transmucosal absorption. Thus the compositions may be formulated as an ingestable, injectable, topical or suppository formulation. The compositions may also be delivered with in a lipoplex, polyplex, target-specific nanoparticle or time-release vehicle. Administration of the compositions to a subject in accordance with the invention appears to exhibit beneficial effects in a dose-dependent manner. Thus, within broad limits, administration of larger quantities of the composition is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the compositions being administered, the disease to be treated or inhibited, the condition of the subject, and other relevant medical factors that may modify the activity of the composition or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the composition will reduce symptoms of the condition at least 10%, 20%, 30%, 40%, 50%, 60%, 70%, 80%, 90% or 100% compared to pre-treatment symptoms or symptoms is left untreated. It is specifically contemplated that pharmaceutical preparations and compositions may palliate or alleviate symptoms of the disease without providing a cure, or, in some embodiments, may be used to cure the disease or disorder.

Suitable effective dosage amounts for administering the compositions may be determined by those of skill in the art, but typically range from about 1 microgram to about 100,000 micrograms per kilogram of body weight weekly, although they are typically about 1,000 micrograms or less per kilogram of body weight weekly. In some embodiments, the effective dosage amount ranges from about 10 to about 10,000 micrograms per kilogram of body weight weekly. In another embodiment, the effective dosage amount ranges from about 50 to about 5,000 micrograms per kilogram of body weight weekly. In another embodiment, the effective dosage amount ranges from about 75 to about 1,000 micrograms per kilogram of body weight weekly. The effective dosage amounts described herein refer to total amounts administered, that is, if more than one composition is administered, the effective dosage amounts correspond to the total amount administered. The composition can be administered as a single dose or as divided doses. For example, the composition may be administered two or more times separated by 4 hours, 6 hours, 8 hours, 12 hours, a day, two days, three days, four days, one week, two weeks, or by three or more weeks.

Miscellaneous

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

REFERENCES

1. Pandey, S, Kawai, T, and Akira, S (2015). Microbial sensing by Toll-like receptors and intracellular nucleic acid sensors. *Cold Spring Harb Perspect Biol* 7: a016246.
2. Pichlmair, A, Lassnig, C, Eberle, C A, Gorna, M W, Baumann, C L, Burkard, T R, et al. (2011). IFIT1 is an antiviral protein that recognizes 5'-triphosphate RNA. *Nat Immunol* 12: 624-630.
3. Jensen, S, and Thomsen, A R (2012). Sensing of RNA viruses: a review of innate immune receptors involved in recognizing RNA virus invasion. *J Virol* 86: 2900-2910.
4. Blander, J M (2014). A long-awaited merger of the pathways mediating host defence and programmed cell death. *Nat Rev Immunol* 14: 601-618.
5. Besch, R, Poeck, H, Hohenauer, T, Senft, D, Hacker, G, Berking, C, et al. (2009). Proapoptotic signaling induced by RIG-I and MDA-5 results in type I interferon-independent apoptosis in human melanoma cells. *J Clin Invest* 119: 2399-2411.
6. Peng, S, Geng, J, Sun, R, Tian, Z, and Wei, H (2009). Polyinosinic-polycytidylic acid liposome induces human hepatoma cells apoptosis which correlates to the up-regulation of RIG-I like receptors. *Cancer Sci* 100: 529-536.
7. Glas, M, Coch, C, Trageser, D, Dassler, J, Simon, M, Koch, P, et al. (2013). Targeting the cytosolic innate immune receptors RIG-I and MDA5 effectively counteracts cancer cell heterogeneity in glioblastoma. *Stem Cells* 31: 1064-1074.
8. Palchetti, S, Starace, D, De Cesaris, P, Filippini, A, Ziparo, E, and Riccioli, A (2015). Transfected poly(I:C) activates different dsRNA receptors, leading to apoptosis or immunoadjuvant response in androgen-independent prostate cancer cells. *J Biol Chem* 290: 5470-5483.
9. Kubler, K, tho Pesch, C, Gehrke, N, Riemann, S, Dassler, J, Coch, C, et al. (2011). Immunogenic cell death of human ovarian cancer cells induced by cytosolic poly(I:C) leads to myeloid cell maturation and activates NK cells. *Eur J Immunol* 41: 3028-3039.
10. Salaun, B, Coste, I, Rissoan, M C, Lebecque, S J, and Renno, T (2006). TLR3 can directly trigger apoptosis in human cancer cells. *J Immunol* 176: 4894-4901.
11. Duewell, P, Steger, A, Lohr, H, Bourhis, H, Hoelz, H, Kirchleitner, S V, et al. (2014). RIG-I-like helicases induce immunogenic cell death of pancreatic cancer cells and sensitize tumors toward killing by CD8(+) T cells. *Cell Death Differ* 21: 1825-1837.
12. Matsushima-Miyagi, T, Hatano, K, Nomura, M, Li-Wen, L, Nishikawa, T, Saga, K, et al. (2012). TRAIL and Noxa are selectively upregulated in prostate cancer cells downstream of the RIG-I/MAVS signaling pathway by non-replicating Sendai virus particles. *Clin Cancer Res* 18: 6271-6283.
13. Kubler, K, Gehrke, N, Riemann, S, Bohnert, V, Zillinger, T, Hartmann, E, et al. (2010). Targeted activation of RNA helicase retinoic acid-inducible gene-I induces proimmunogenic apoptosis of human ovarian cancer cells. *Cancer Res* 70: 5293-5304.
14. Lion, E, Anguille, S, Berneman, Z N, Smits, E L, and Van Tendeloo, V F (2011). Poly(I:C) enhances the susceptibility of leukemic cells to NK cell cytotoxicity and phagocytosis by DC. *PLoS One* 6: e20952.
15. Trinchieri, G (2010). Type I interferon: friend or foe? *J Exp Med* 207: 2053-2063.
16. Lampkin, B C, Levine, A S, Levy, H, Krivit, W, and Hammond, D (1985). Phase II trial of a complex polyriboinosinic-polyribocytidylic acid with poly-L-lysine and carboxymethyl cellulose in the treatment of children with acute leukemia and neuroblastoma: a report from the Children's Cancer Study Group. *Cancer Res* 45: 5904-5909.
17. Vacchelli, E, Eggermont, A, Sautes-Fridman, C, Galon, J, Zitvogel, L, Kroemer, G, et al. (2013). Trial Watch: Toll-like receptor agonists for cancer therapy. *Oncoimmunology* 2: e25238.
18. Kaczanowska, S, Joseph, A M, and Davila, E (2013). TLR agonists: our best frenemy in cancer immunotherapy. *J Leukoc Biol* 93: 847-863.
19. Mumm, J B, and Oft, M (2008). Cytokine-based transformation of immune surveillance into tumor-promoting inflammation. *Oncogene* 27: 5913-5919.
20. Duewell, P, Beller, E, Kirchleitner, S V, Adunka, T, Bourhis, H, Siveke, J, et al. (2015). Targeted activation of melanoma differentiation-associated protein 5 (MDA5) for immunotherapy of pancreatic carcinoma. *Oncoimmunology* 4: e1029698.
21. He, W A, Calore, F, Londhe, P, Canella, A, Guttridge, D C, and Croce, C M (2014). Microvesicles containing miRNAs promote muscle cell death in cancer cachexia via TLR7. *Proc Natl Acad Sci USA* 111: 4525-4529.
22. Yu, X, Wang, H, Li, X, Guo, C, Yuan, F, Fisher, P B, et al. (2016). Activation of the MDA5-IPS1 viral sensing pathway induces cancer cell death and type I interferon-dependent antitumor immunity. *Cancer Res*.
23. Schmidt, A, Schwerd, T, Hamm, W, Hellmuth, J C, Cui, S, Wenzel, M, et al. (2009). 5'-triphosphate RNA requires base-paired structures to activate antiviral signaling via RIG-I. *Proc Natl Acad Sci USA* 106: 12067-12072.

24. Kohlway, A, Luo, D, Rawling, D C, Ding, S C, and Pyle, A M (2013). Defining the functional determinants for RNA surveillance by RIG-I. *EMBO Rep* 14: 772-779.
25. Kato, H, Takeuchi, O, Mikamo-Satoh, E, Hirai, R, Kawai, T, Matsushita, K, et al. (2008). Length-dependent recognition of double-stranded ribonucleic acids by retinoic acid-inducible gene-I and melanoma differentiation-associated gene 5. *J Exp Med* 205: 1601-1610.
26. Kleinman, M E, Yamada, K, Takeda, A, Chandrasekaran, V, Nozaki, M, Baffi, J Z, et al. (2008). Sequence- and target-independent angiogenesis suppression by siRNA via TLR3. *Nature* 452: 591-597.
27. Heil, F, Hemmi, H, Hochrein, H, Ampenberger, F, Kirschning, C, Akira, S, et al. (2004). Species-specific recognition of single-stranded RNA via toll-like receptor 7 and 8. *Science* 303: 1526-1529.
28. Lee, Y, Urban, J H, Xu, L, Sullenger, B A, and Lee, J (2016). 2'Fluoro Modification Differentially Modulates the Ability of RNAs to Activate Pattern Recognition Receptors. *Nucleic Acid Ther* 26: 173-182.
29. Vermes, I, Haanen, C, Steffens-Nakken, H, and Reutelingsperger, C (1995). A novel assay for apoptosis. Flow cytometric detection of phosphatidylserine expression on early apoptotic cells using fluorescein labelled Annexin V. *Journal of immunological methods* 184: 39-51.
30. Chawla-Sarkar, M, Leaman, D W, and Borden, E C (2001). Preferential induction of apoptosis by interferon (IFN)-beta compared with IFN-alpha2: correlation with TRAIL/Apo2L induction in melanoma cell lines. *Clin Cancer Res* 7: 1821-1831.
31. Robinson, N, McComb, S, Mulligan, R, Dudani, R, Krishnan, L, and Sad, S (2012). Type I interferon induces necroptosis in macrophages during infection with *Salmonella enterica* serovar *Typhimurium*. *Nat Immunol* 13: 954-962.
32. Chattopadhyay, S, Marques, J T, Yamashita, M, Peters, K L, Smith, K, Desai, A, et al. (2010). Viral apoptosis is induced by IRF-3-mediated activation of Bax. *EMBO J* 29: 1762-1773.
33. Kroemer, G, Galluzzi, L, Kepp, O, and Zitvogel, L (2013). Immunogenic cell death in cancer therapy. *Annual review of immunology* 31: 51-72.
34. Obeid, M, Tesniere, A, Ghiringhelli, F, Fimia, G M, Apetoh, L, Perfettini, J L et al. (2007). Calreticulin exposure dictates the immunogenicity of cancer cell death. *Nat Med* 13: 54-61.
35. Gando, S, and Otomo, Y (2015). Local hemostasis, immunothrombosis, and systemic disseminated intravascular coagulation in trauma and traumatic shock. *Crit Care* 19: 72.
36. Alonso, D F, Ripoll, G V, Garona, J, Iannucci, N B, and Gomez, D E (2011). Metastasis: recent discoveries and novel perioperative treatment strategies with particular interest in the hemostatic compound desmopressin. *Curr Pharm Biotechnol* 12: 1974-1980.
37. Green, D R, Ferguson, T, Zitvogel, L, and Kroemer, G (2009). Immunogenic and tolerogenic cell death. *Nat Rev Immunol* 9: 353-363.
38. Casares, N, Pequignot, M O, Tesniere, A, Ghiringhelli, F, Roux, S, Chaput, N, et al. (2005). Caspase-dependent immunogenicity of doxorubicin-induced tumor cell death. *J Exp Med* 202: 1691-1701.
39. Kazama, H, Ricci, J E, Herndon, J M, Hoppe, G, Green, D R, and Ferguson, T A (2008). Induction of immunological tolerance by apoptotic cells requires caspase-dependent oxidation of high-mobility group box-1 protein. *Immunity* 29: 21-32.
40. Yang, H, Antoine, D J, Andersson, U, and Tracey, K (2013). The many faces of HMGB1: molecular structure-functional activity in inflammation, apoptosis, and chemotaxis. *J Leukoc Biol* 93: 865-873.
41. Uzri, D, and Gehrke, L (2009). Nucleotide sequences and modifications that determine RIG-I/RNA binding and signaling activities. *J Virol* 83: 4174-4184.
42. Song, W, Wang, J, Han, Z, Zhang, Y, Zhang, H, Wang, W, et al. (2015). Structural basis for specific recognition of single-stranded RNA by Toll-like receptor 13. *Nat Struct Mol Biol* 22: 782-787.
43. Strober, W, and Watanabe, T (2011). NOD2, an intracellular innate immune sensor involved in host defense and Crohn's disease. *Mucosal Immunol* 4: 484-495.
44. Sabbah, A, Chang, T H, Harnack, R, Frohlich, V, Tominaga, K, Dube, P H, et al. (2009). Activation of innate immune antiviral responses by Nod2. *Nat Immunol* 10: 1073-1080.
45. Twyman-Saint Victor, C, Rech, A J, Maity, A, Rengan, R, Pauken, K E, Stelekati, E, et al. (2015). Radiation and dual checkpoint blockade activate non-redundant immune mechanisms in cancer. *Nature* 520: 373-377.
46. Lee, J, Boczkowski, D, and Nair, S (2013). Programming human dendritic cells with mRNA. *Methods Mol Biol* 969: 111-125.

EXAMPLES

Materials and Methods

Cell Culture

Human melanoma cell line WM266-4 (ATCC, Manassas, Va.) was maintained in Eagle's Minimum Essential Medium supplemented with 10% FBS, 1× non-essential Amino Acid (NEAA) and 1 mM sodium pyruvate (all from Invitrogen, Carlsbad, Calif.). Human prostate cancer cell line DU145 (ATCC) was cultured in Dulbecco's Modified Eagle's Medium (DMEM) (Invitrogen) supplemented with 1×NEAA and 1 mM sodium pyruvate, 10% FBS. Human hepatocellular carcinoma cell lines, Huh7.0 and Huh7.5, were kindly provided by Dr. Stacy M. Homer, Duke University. Huh7.0, Huh7.5, human pancreatic cancer cell line PANC-1 (ATCC), murine pancreatic cancer cell line PANC-02 (NIH) and murine melanoma cell line B16.F0 (ATCC) were maintained in DMEM supplemented with 10% FBS. Human pancreatic cancer cell line BxPC3 cells were maintained in RPMI 1640 (Invitrogen) with 10% FBS and 2 mM L-glutamine. TLR reporter cell lines, HEK-Blue Null, HEK-Blue hTLR2, HEK-Blue hTLR3, HEK-Blue hTLR4 and HEK-Blue hTLR9 cells (all purchased from InvivoGen, San Diego, Calif.) stably express an NF-kB/AP-1-inducible secreted embryonic alkaline phosphatase (SEAP) and corresponding TLR, and these cells were maintained by following the manufacturer's instructions. Human normal peripheral blood mononuclear cells (PBMCs) (Stemcell Technologies, Vancouver, Canada) were cultured in RPMI 1640 with 10% FBS and 2 mM L-glutamine. Immature dendritic cells (DCs) were generated from PBMCs as previously described[46]. All cells were incubated at 37° C. in a humidified atmosphere with 5% $CO_2$.

Generation of ICRs

All ICRs were produced by in vitro transcription from DNA templates using the Y639F mutant T7 RNA polymerase, followed by gel purification, as previously described.[28] All pyrimidines in the ICRs are 2' fluoro-modified.

In Vitro RNA Treatment and PRR Stimulation

ICRs and polyI:C were transfected with either Dharma-FECT® Duo liposomal transfection reagent (Thermo Scientific, Waltham, Mass.) at a transfection reagent (μl):RNA (μg) ratio of 3:1 according to the manufacturer's instructions. RNAs were transfected into 80-90% confluent cells. Cells were incubated with an RNA-transfection agent complex for 4 h, followed by replenishment with fresh culture medium. Cells and culture supernatants were harvested at various time points. Pam3CSK4, CpG 2006, PolyI:C, R848 (all from InvivoGen) and LPS (Sigma) were used as control TLR and PRR agonists.

Quantification of Cell Growth Inhibition and Cell Death

Growth inhibition relative to untreated cells was quantified at 72 h after treatments using Celltiter 96® MTS Cell Proliferation Assay Kit (Promega, Madison, Wis.), according to the manufacturer's instructions. The percent growth inhibition was calculated by using the following equation: % growth inhibition=$([O.D.]_{untreated}-[O.D.]_{treated})/[O.D.]_{untreated} \times 100$. Cell death was measured using the PE Annexin V Apoptosis Detection Kit I (BD Biosciences, San Jose, Calif.).

Inhibition of Type I IFNs, RIPK and Caspases

Cells were treated with type I IFN decoy receptor B18R (1 μg/ml) (eBioscience, San Diego, Calif.), RIP kinase inhibitor necrostatin-1 (100 μM) (Sigma, Saint Louis, Mo.) and pan-caspase inhibitor Z-VAD-fmk (50 μM) (InvivoGen) for 6 h before and immediately after RNA treatment. To induce IFN-3-dependent cell death, cells were treated with recombinant human IFN-β (100 ng/ml) (Peprotech, Rocky Hill, N.J.).

siRNA Knockdown of RIG-I, PKR and MDA5 Expression

Transient knockdown of RIG-I, PKR and MDA5 were performed as previously described.[28] At 5 h after the second siRNA transfection, cells were harvested, replated into a 96-well plate and incubated overnight. Cells were then treated with PRR-activating RNAs.

Generation of DAMPs

To generate DAMPs, $5 \times 10^5$ WM266-4 cells were transfected with RNAs (1 μg/ml) or incubated with doxorubicin (7.5 μM) (Sigma). After 4 h, cells were washed 5 times with fresh culture media and incubated for 2-3 days in 1 ml of culture media. Dead cells were counted using Trypan blue. When over 95% cells were dead, culture supernatants were collected by centrifugation for 5 min at 1200 RPM and stored at −80° C. until use.

Phagocytosis Assay

Cells were labeled using PKH67 Green Fluorescent Cell Linker Kit (Sigma). PKH67-labeled cells were killed using RNAs or doxorubicin (7.5 μM) (Sigma). Dead/dying cells were harvested at 48 h after treatment and incubated for 1 h with immature DCs. Phagocytosis of PKH67-labeled dead/dying cells was determined by flow cytometry.

DAMP-Induced TLR Activation and DC Stimulation

DAMPs were diluted to 25% (v/v) with complete media. $5 \times 10^4$ TLR reporter cells or $1 \times 10^5$ immature DCs were incubated overnight with diluted DAMPs in a 96-well plate. To determined TLR activation, the level of SEAP release was determined using a colorimetric assay. Briefly, 40 μl culture supernatants were harvested and incubated for 3 h with 180 μl QUANTI-Blue™ (InvivoGen) in a flat-bottom 96-well plate. SEAP activity was accessed by reading the optical density (OD) at 650 nm with BioTek Power Wave XS2 ELISA plate reader (BioTek, Winooski, Vt.). Pam3CSK4 (TLR2 agonist), CpG 2006 (TLR9 agonist), PolyI:C (TLR3 agonist) and LPS (all from InvivoGen) were used as control TLR stimulators. To determine DC stimulation, cytokine production by DCs was determined by ELISA.

In Vivo Anti-Tumor Therapy 5-6 weeks old NU/J mice were obtained from the Jackson Laboratory (Bar Harbor, Me.). $7 \times 10^5$ WM266-4 human melanoma cells were implanted subcutaneously into the right flank of a NU/J nude mouse. When mice have a palpable tumor, the tumor-bearing mice were intratumorally injected with 20 μg of RNA molecules using in vivo-jetPEI® (Polyplus transfection, New York, N.Y.) at N/P=8. RNAs were daily injected for 5 consecutive days. Tumor growth was evaluated every other day by measuring tumor diameter using a caliper. Tumor volume was defined as $[(width)^2 \times (length)]/2$. Mice bearing tumor volume exceeding 2000 mm³ were euthanized. All experimental procedures involving the use of mice were performed in accordance with the guidelines and in compliance with the Animal Care and Use Committee of Duke University.

Enzyme-Linked Immunosorbent Assay (ELISA)

TNF-α, IL-6 and IL-8 were determined using BD OptEIA™ ELISA sets (BD Biosciences, Franklin Lakes, N.J.). IFN-β production was determined using IFN-β ELISA kit (PBL Biomedical Laboratories, Piscataway, N.J.). HMGB-1 secretion was determined using HMGB1 ELISA kit (Tecan, Morrisville, N.C.) by following the manufacturer's instructions.

Immunoblot Analysis and Antibodies

Mitochondria and nuclear fractions were isolated using Mitochondria Isolation kit and NE-PER Nuclear Extraction reagent, respectively, (both from Thermo Scientific). Mitochondrial lysates, nuclear lysates and total cell lysates were prepared in 1×RIPA buffer (Sigma, St. Louis, Mo.) in the presence of the complete protease inhibitor cocktail and phosphatase inhibitor cocktail (Sigma). 30 μg of protein lysates were electrophoretically separated on 4-20% Mini-PROTEAN® TGX™ polyacrylamide gels (Bio-Rad, Hercules, Calif.) and transferred to polyvinylidene fluoride (PVDF) membranes (PolyScreen®, PerkinElmer). After rinsing in TBST20, membranes were blocked for 1 h in 5% dry milk in TBTS20, followed by overnight incubation with primary antibodies anti-XIAP (1:1000) (3B6; Cell Signaling, Danvers, Mass.), anti-TRAIL (1:1000) (C92B9; Cell Signaling), anti-phospo (p)-IRF-3 (1:500) (4D4G; Cell Signaling), anti-cleaved caspase-3 (1:200) (D3E9; Cell Signaling), anti-caspase-7 (1:200) (Cell Signaling), anti-NF-κB p65 (1:1,000) (L8F6; Cell Signaling), anti-RIP (1:1,000) (Cell Signaling), anti-RIG-I (1:500) (D14G6; Cell Signaling, Danvers, Mass.), anti-MDA5 (1:500) (D74E4; Cell Signaling) and anti-PKR (1:350) (Catalog No 3072; Cell Signaling). When different proteins were sequentially detected on the same membrane, membranes were treated for 8 minutes with Restore Western Blot Stripping Buffer (Thermo Scientific, Rockford, Ill.), washed, blocked and probed again, as described above. Primary antibodies were detected using horseradish peroxidase (HRP)-conjugated anti-rabbit (1:2,000) (Cell Signaling) or anti-mouse (1:2,000) (Cell Signaling) secondary antibodies. Anti-β-Tubulin (1:1,000) (9F3; Cell Signaling), anti-CoxIV (1:1,000) (3E11; Cell Signaling) and anti-Histone H3 (1:1,000) (D1H2; Cell Signaling) were used as loading controls. HRP activity was visualized using the Western Lightning Plus Kit (PerkinElmer, Waltham, Mass.).

Detection of Surface Calreticulin and Cytoplasmic HMGB-1

The expression of surface Calreticulin was determined by flow cytometry after co-staining with anti-Calreticulin-PE (1/100 dilution) (Abcam, Cambridge, Mass.) and 7-AAD (BD Biosciences). For the detection of HMGB1, cells were fixed with a 4% paraformaldehyde solution followed by blocking and permeabilization with 5% BSA, 0.2% Triton X-100 in PBS, and stained overnight with anti-HMGB1 (1/1000 dilution) (Abcam), Alexa Fluor 488-conjugated goat anti-rabbit IgG (1/1000 dilution) (Abcam) was used as a secondary antibody. DAPI (4',6-Diamidino-2-phenylindole) (Sigma) was used as a nuclear counterstain. The expression of HMGB1 and DAPI was observed under a Zeiss Axio Observer microscope, and the images were analyzed using MetaMorph software (Sunnyvale, Calif.).

Clotting Assay

5 µl DAMPs or culture media were mixed with 50 µL normal pooled human plasma (George King Bio-Medical Inc., Overland Park, Kans.). The mixture was incubated for 3 min at 37° C., followed by the addition of 50 µL $CaCl_2$ (25 mM). Clotting times were recorded using STart® Hemostasis Analyzer (Diagnostica Stago, Parsippany, N.J.).

Statistical Analysis

The difference of cell growth, cell death, cytokine production and tumor volume among experimental groups was compared using the two-tailed Student's t test. Significance of survival was determined by log-rank (Mantel-Cox) test. A probability of less than 0.05 ($p<0.05$) was used for statistical significance.

Example 1: Screening of RNA Molecules for Differential Induction of Cancer Cell Death and Expression of IFN-β and Pro-Inflammatory Cytokines 5'(p)pp and short RNA duplex composed of interstranded or intrastranded base pairs (10-20 bp) are well-known motifs recognized by RIG-I.[23, 24] MDA5 and TLR3 are activated by long dsRNA (0.5-6 kb)[25] and short dsRNAs (>21 bp),[26] respectively, in a sequence-independent manner, whereas TLR7 is activated by AU- and GU-rich short ssRNAs in a sequence-dependent manner.[27] However, other motifs recognized by RIG-I, MDA5, TLR3 and TLR7 likely exist. We recently found that transfection with RNA aptamers containing 5'ppp and stem-loop(s) induced cell death and IFN-β expression in human melanoma cells in a RIG-I and IPS-I-dependent manner.[28] Using the structure and sequence information of these RNA ligands, we first designed ssRNAs containing 5'ppp, AU and GU motifs and various length and numbers of stem-loops to determine optimal RNA structures for enhancement of PRR-mediated immunogenic cell death and type I IFN expression in human cancer cells (FIG. 1A and Table 1). To increase stability and cellular half-life of RNA ligands, we incorporated 2'fluoro (2'F) pyrimidines into the RNAs. These RNAs are referred to as Immunogenic Cancer cell-killing RNAs (ICRs).

Figure 1B:
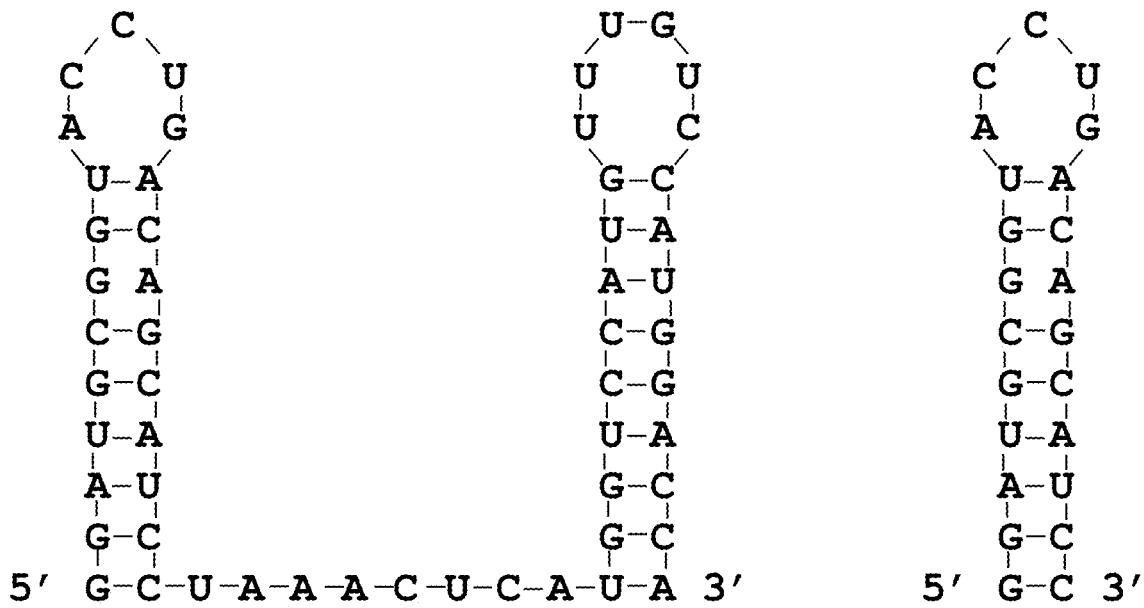
FIGS. 1B-1C illustrates (FIG. 1B) the predicted structure of ICR4 (SEQ ID NO: 15), ICR2 (SEQ ID NO: 8), ICR2-1 (SEQ ID NO: 7), ICR2-2 (SEQ ID NO: 6), and ICR2-3 (SEQ ID NO: 5) and (FIG. 1C) the cytotoxicity of 5'ppp 2'F hairpin RNAs with 6-9 bp stems. WM266-4 cells were transfected for 4 h with the indicated RNA. Cell growth rates were determined at 3 days after transfection by MTS assay. Error bars are S.D.
Figure 1B:
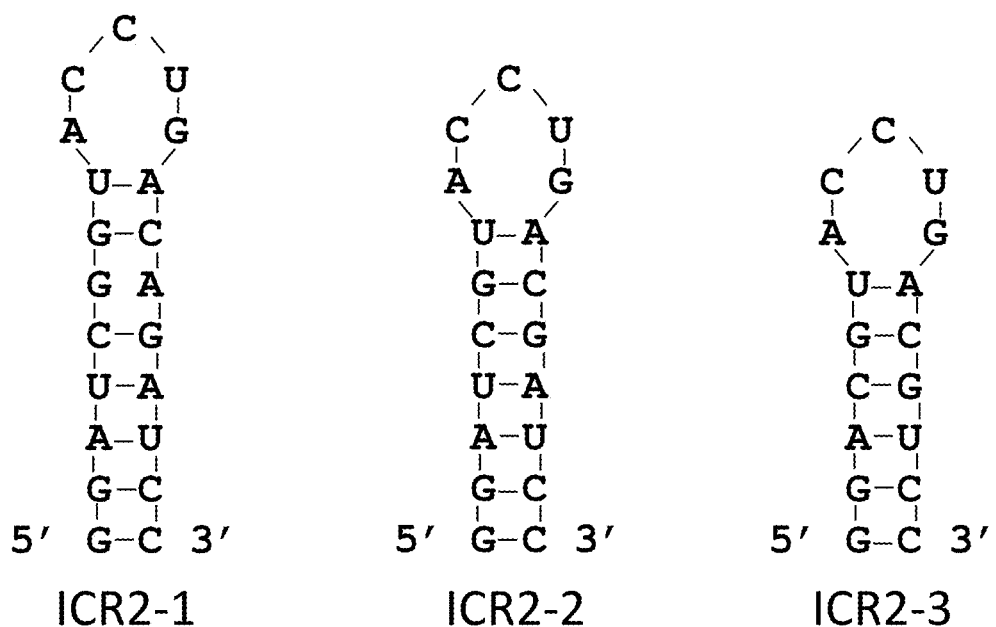
Figure 1C:
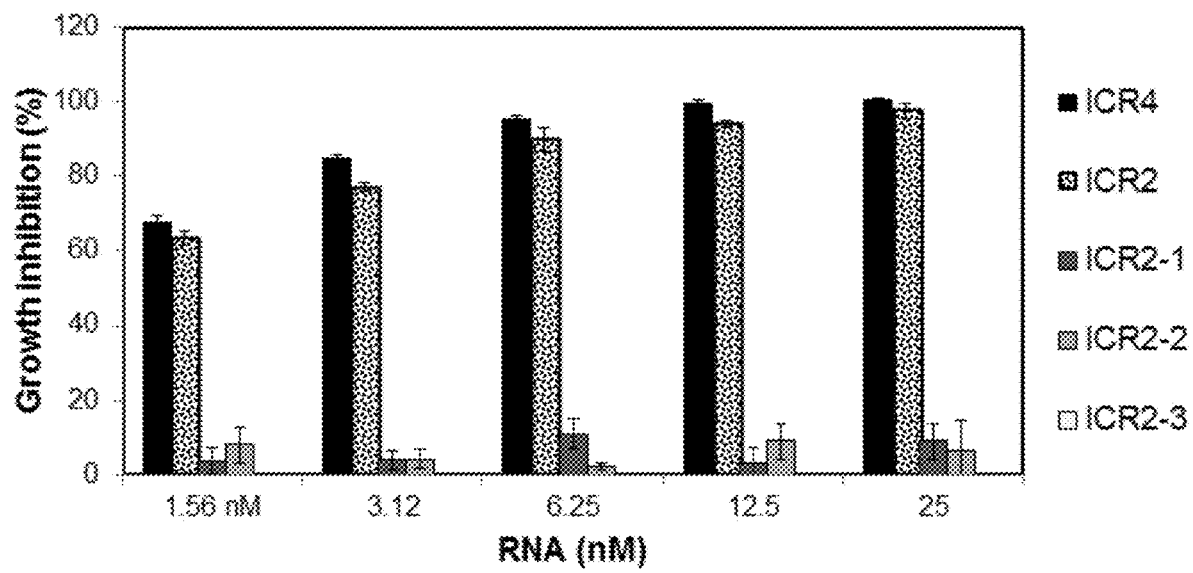
Figure 2A:
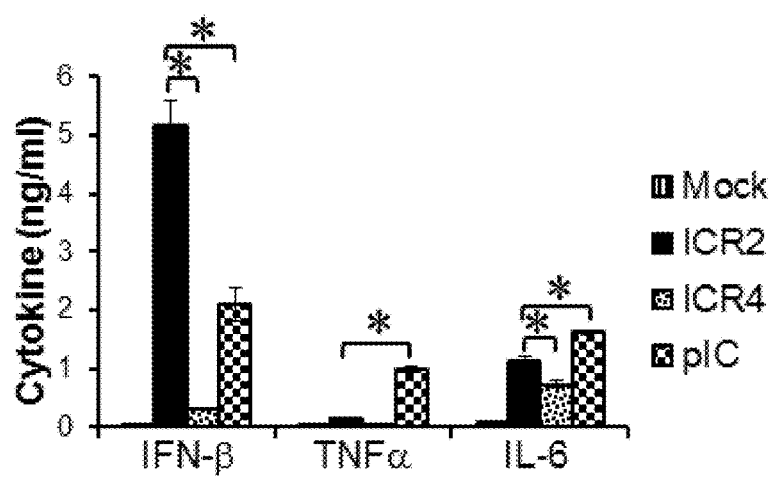
FIGS. 2A-2E shows ICR4 induces decreased IFN-β and pro-inflammatory cytokine expression in human cancer cells and innate immune cells compared with ICR2. WM266-4 cells ($1\times10^4$ cells/well) (FIG. 2A), human PBMCs ($1\times10^5$ cells/well) (FIG. 2B, FIG. 2E) and human DCs ($5\times10^4$ cells/well) (FIG. 2C-2D) were transfected for 4 h with ICR2, ICR4, polyI:C (1 µg/ml each) or transfection agent alone (Mock) in a 96-well plate.

Transfection with ICRs containing at least one stem structure longer than 9 bp induced cytotoxicity in human melanoma cells in a dose-dependent manner, whereas linear ICRs and ICRs containing a stem structure shorter than 9 bp had no cytotoxicity in these cells (FIG. 1A-1C). Interestingly, the 5'-overhang length but not the 3'-overhang length is inversely correlated with cytotoxicity. Unlike cytotoxicity, ICRs with blunt end on 9-12 bp long stem loop induced 2 to 3-fold higher production of IFN-β by human melanoma cells than polyI:C, whereas the length of 5' and 3' overhangs and the number and length of stem loops were inversely correlated with IFN-β expression in human melanoma cells (FIGS. 1A and 2A). To elucidate the difference between cytotoxicity and IFN-β expression patterns of different ICRs, we further investigated two representative ICRs, ICR2 and ICR4. ICR2 is a blunt-ended, hairpin RNA with 23 nt in length and induced high cytotoxicity and high IFN-β expression, whereas ICR4 is predicted to form a double stem-loop structure with 55 nt in length and induced high cytotoxicity and low IFN-β expression (FIG. 1A-1C).

Figure 2B:
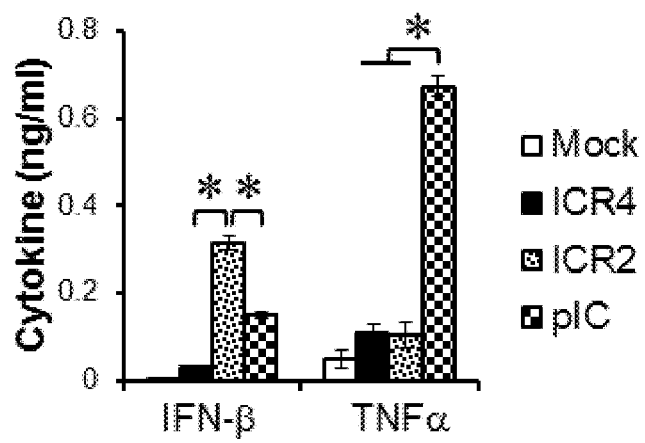
Figure 2C:
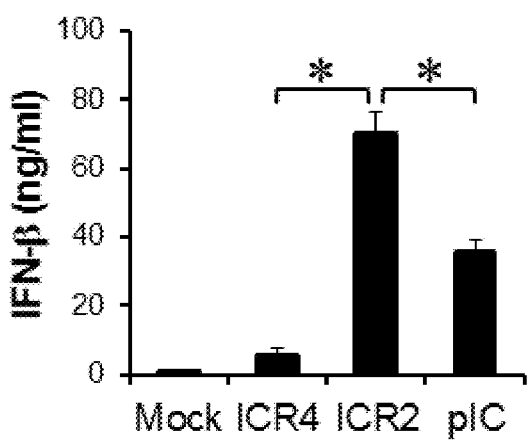
Figure 2D:
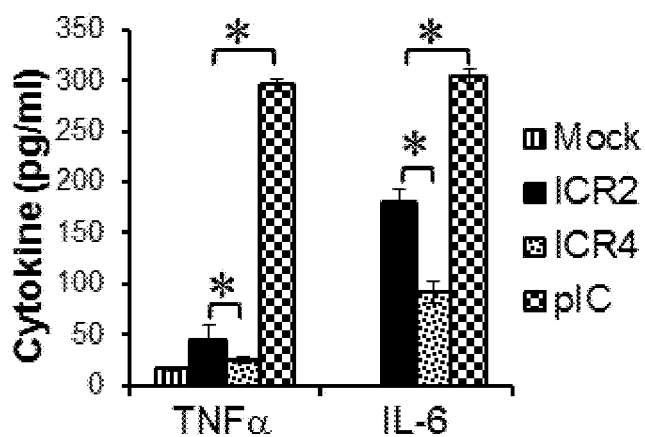
Figure 2E:
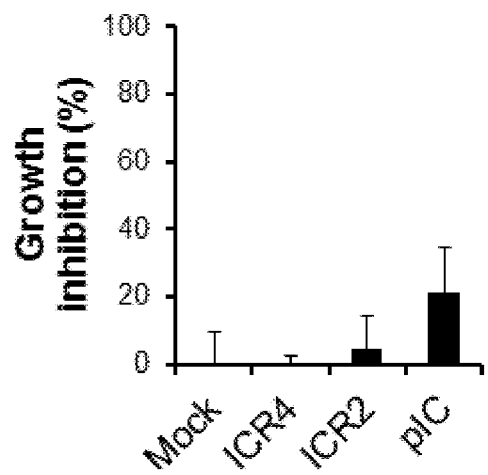
Figure 2F:
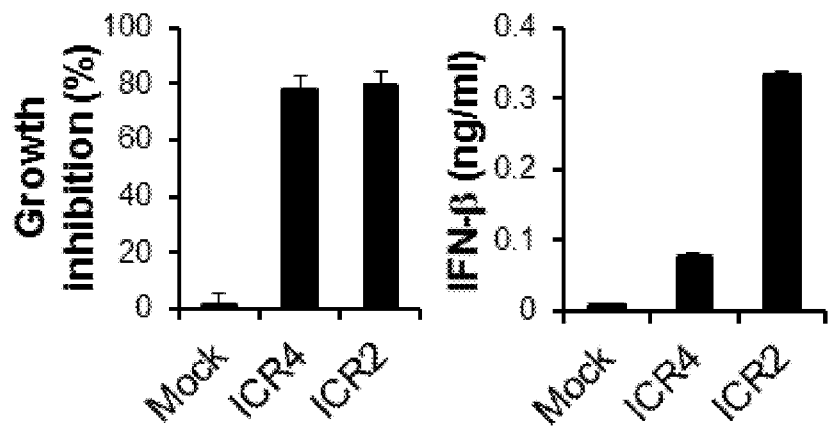
FIGS. 2F-2H show differential induction of IFN-β expression and growth inhibition of human prostate and human pancreatic cancer cells by ICR2 and ICR4. DU-145 human prostate cancer cell line (FIG. 2F), PANC-1 human pancreatic cancer cell line (FIG. 2G) and BxPC3 human pancreatic cancer cell line (FIG. 2H) were transfected with ICR2, ICR4 (1 µg/ml each) or transfection reagent alone (Mock). Cell growth and IFN-β production were determined by MTS assay and ELISA, respectively. Error bars are S.D.
Figure 2G:
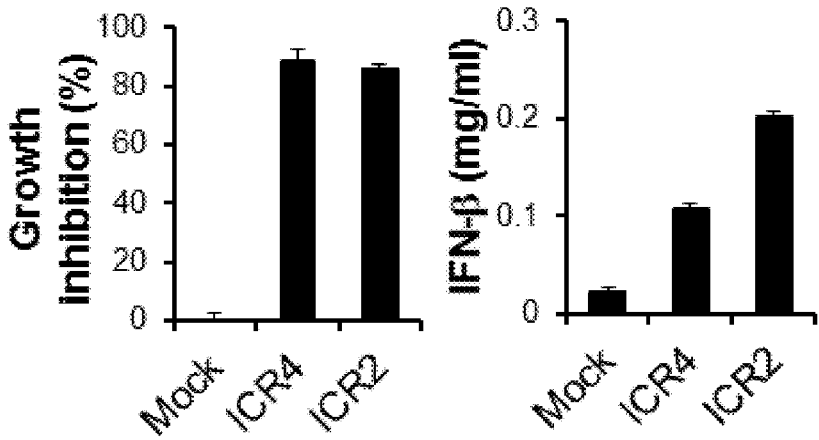
Figure 2H:
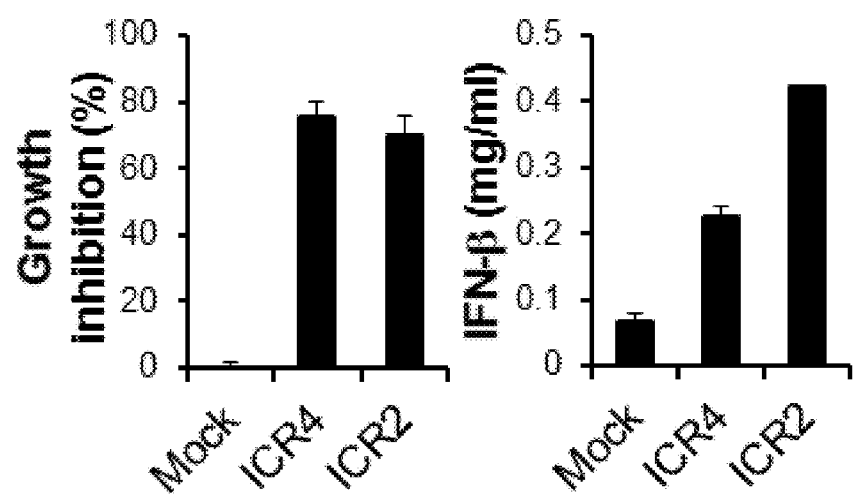
Figure 2I:
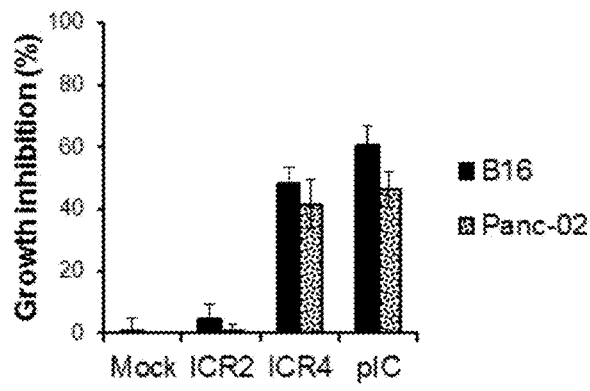
FIG. 2I-2L show cytotoxicity (FIG. 2I) and cytokine production (FIG. 2J-L) by mouse cancer cells transfected with ICR2, ICR4 and polyI:C. B16 mouse melanoma cell line and PANC-02 mouse pancreatic cancer cell line were transfected with transfection reagent alone (Mock), ICR2, ICR4 or polyI:C (pIC) (1 µg/ml each). Cells and culture supernatants were harvested at 3 days after transfection. Cell growth (FIG. 2I) and production of (FIG. 2J) IFN-β, (FIG. 2K) IL-6 and (FIG. 2L) TNFα were determined by MTS assay and ELISA, respectively. Error bars are S.D.
Figure 2J:
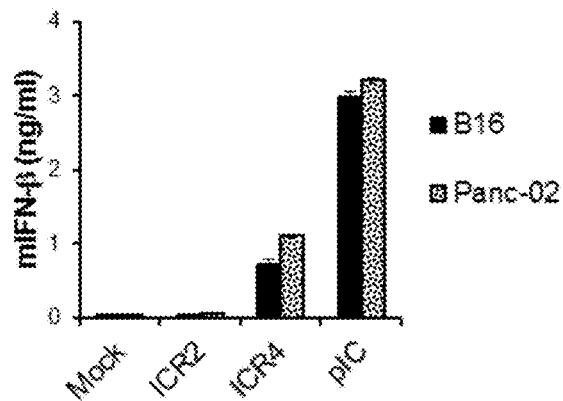
Figure 2K:
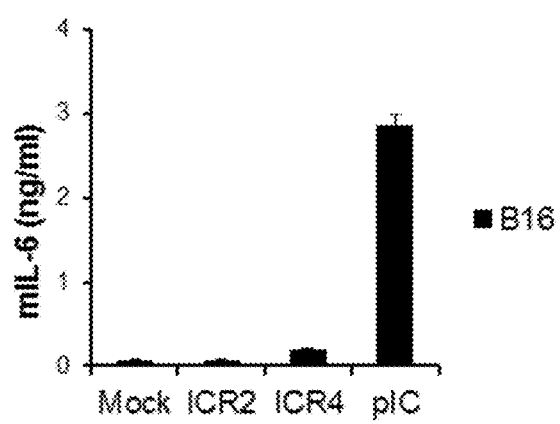
Figure 2L:
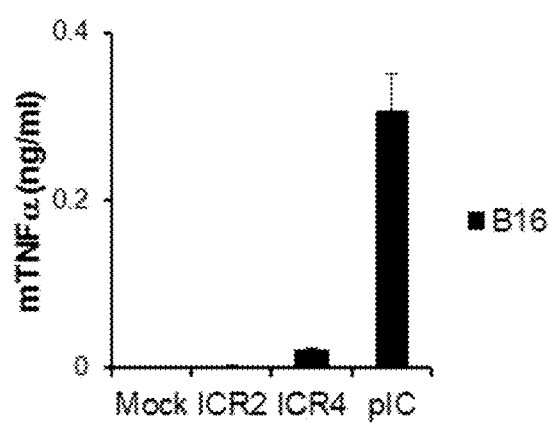

Example 2: ICR2 and ICR4 Differentially Induced Expression of Pro-Inflammatory Cytokines and IFN-β in Human and Mouse Cancer Cells and Innate Immune Cells We next asked whether ICR2 and ICR4 differentially induced cytotoxicity and IFN-β expression in different types of cancer cells other than melanoma cells. Both ICR2 and ICR4 induced over 70% decrease in proliferation of human prostate cancer cells (DU-145) and human pancreatic cancer cells (PANC-1 and BxPC3). ICR2 induced more than a two-fold higher increase in IFN-β expression in these cells than did ICR4 (FIGS. 2F-2G). Differential induction of IFN-β expression by ICR2 and ICR4 was also observed in innate immune cells, including human PBMC and DC (FIGS. 2B-2C). In addition to IFN-β, the expression of pro-inflammatory cytokines, e.g., tumor necrosis factor (TNF) α and interleukin (IL)-6, in human DCs were significantly less induced by ICR4 than ICR2 (FIG. 2D). Interestingly, transfection with ICR2 induced significantly higher IFN-β expression in human cancer cells and DCs than did transfection with polyI:C, but transfection with ICR2 induced significantly lower expression of TNFα and IL-6 than did transfection with polyI:C (FIGS. 2A, 2C, and 2D). In contrast to cancer cells, ICR2 and ICR4 did not induce cytotoxicity in human PBMCs (FIG. 2E). Surprisingly, ICR2 did not induce cytotoxicity nor expression of IFN-β, TNFα and IL-6 in mouse cancer cells. ICR4 induced cytotoxicity and IFN-β expression in mouse melanoma and mouse pancreatic cancer cells although the cytotoxic effects were much less in mouse cancer cells compared with human counterparts (48.11±5.365% (B16) vs 92.7075±1.223% (WM266-4); 41.59±7.809% (PANC-02) vs 88.39±4.470% (PANC-1) (FIGS. 2F-2H and 2I-2L).

Figure 3A:
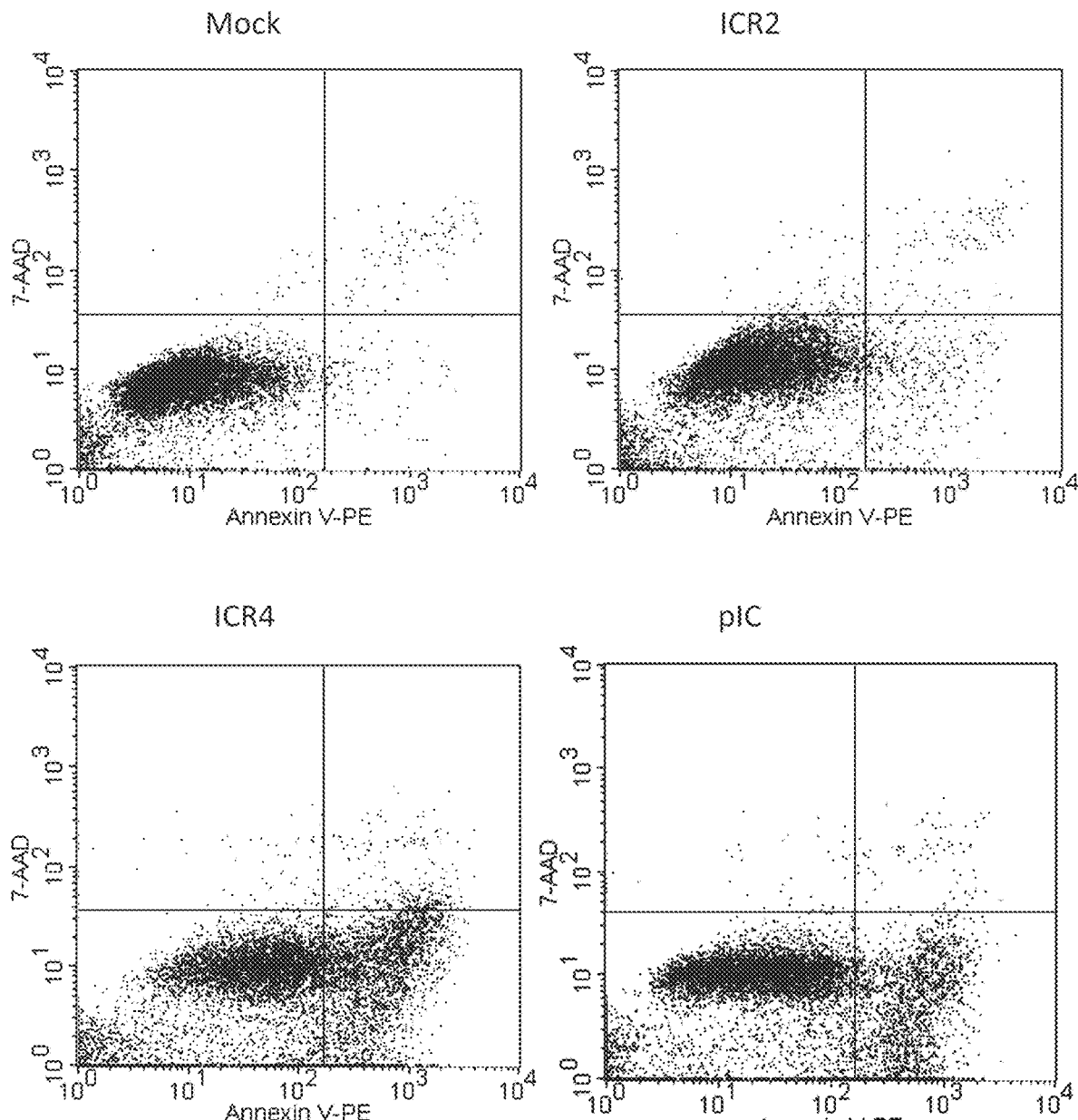
Figure 3B:
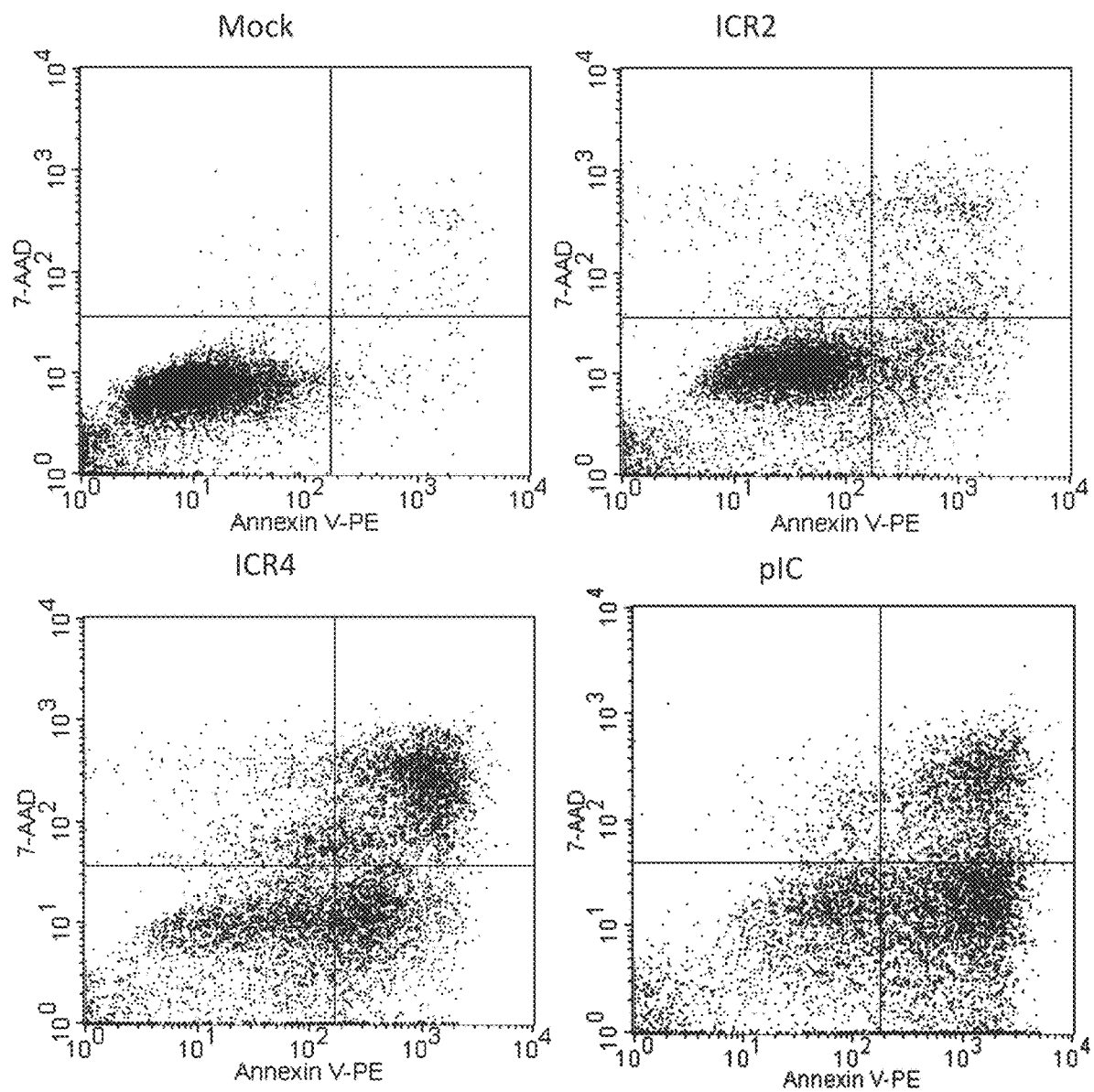
Figure 3C:
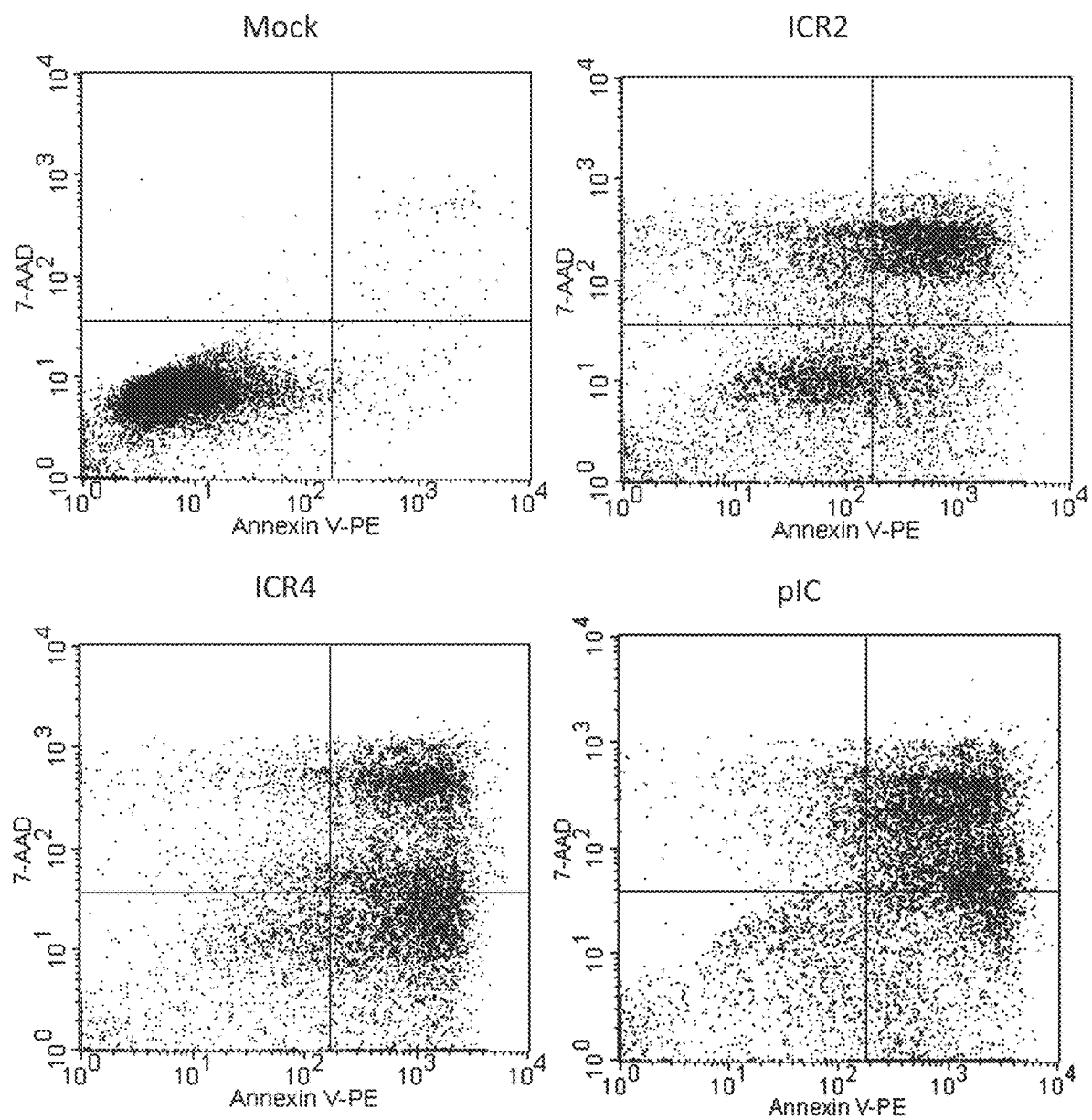
Figure 3F:
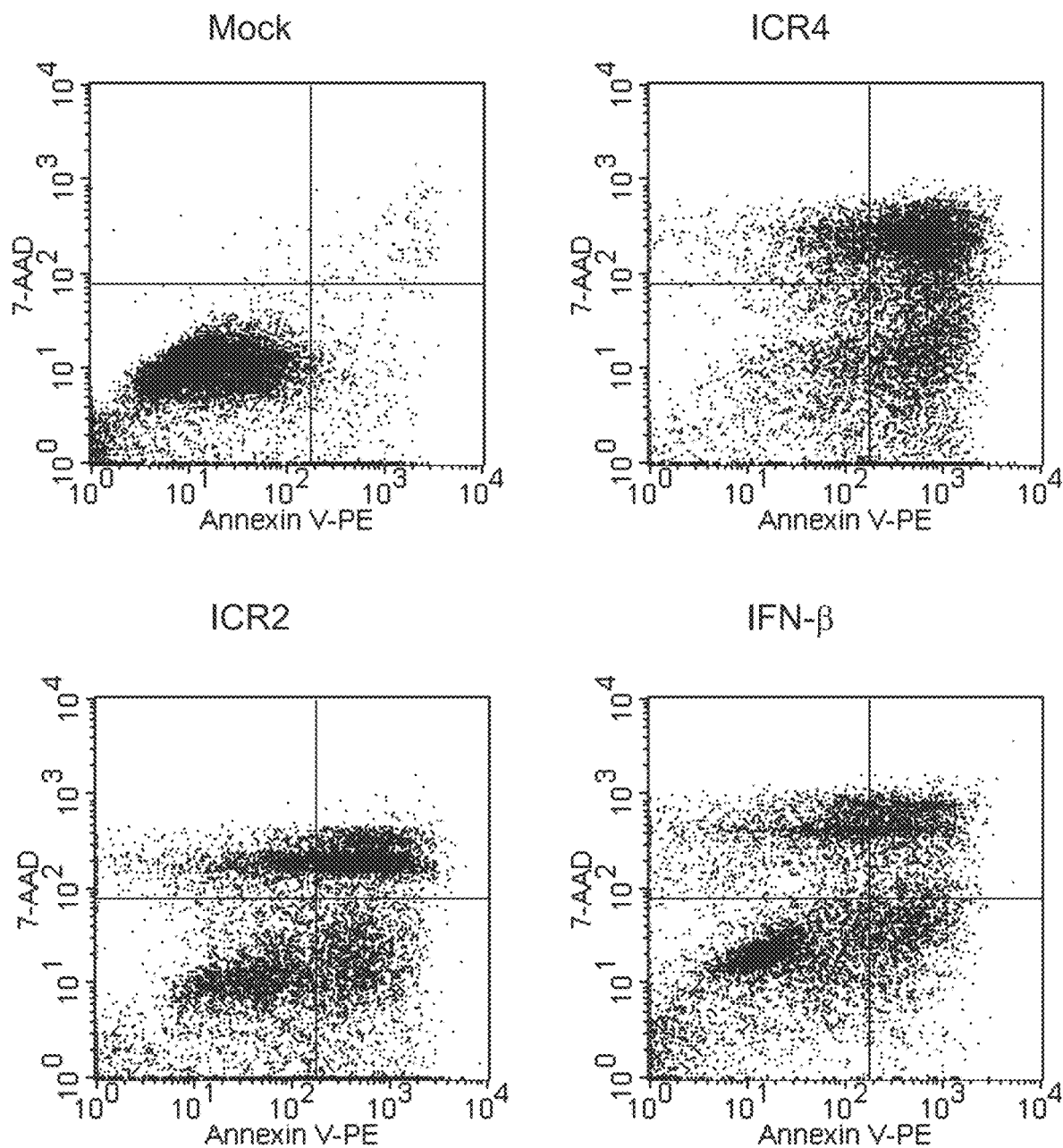
Figure 3G:
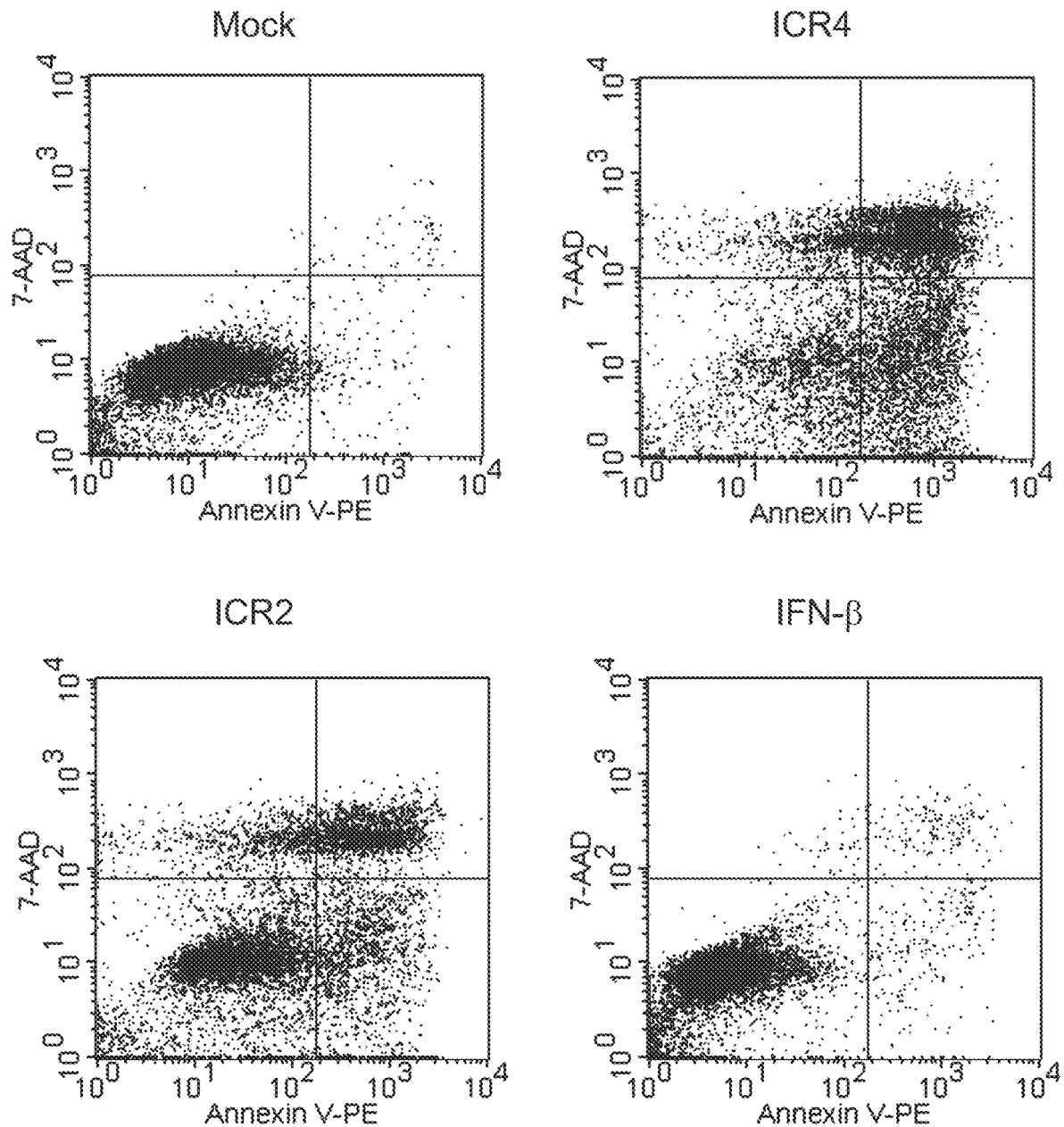
Figure 3I:
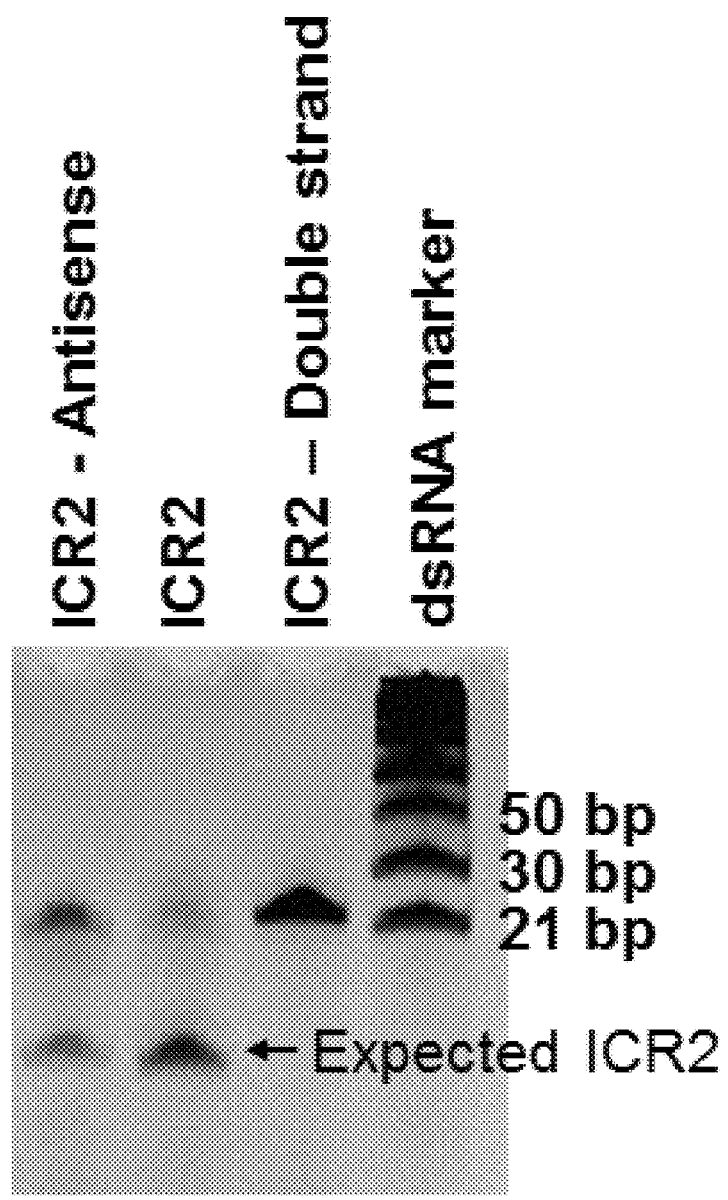
FIGS. 3I-3K show generation of T7 polymerase-induced IVT byproduct.
Figure 3J:
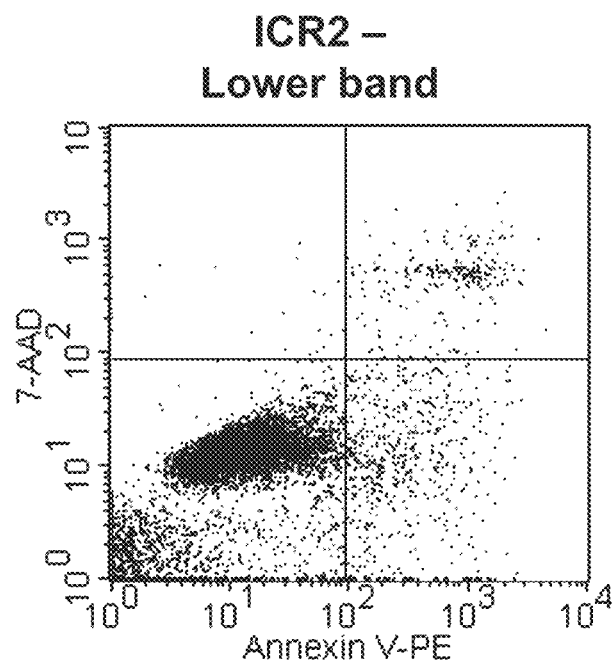
Figure 3K:
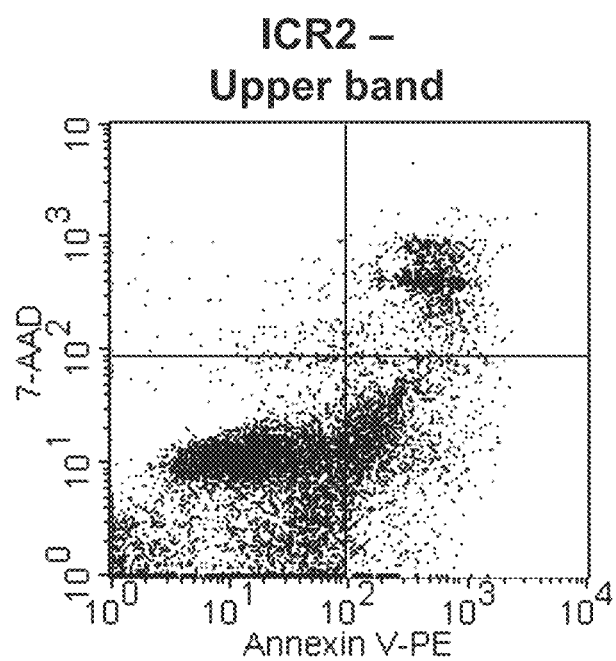

Example 3: ICR2 Induced Delayed, IFN-Dependent Cell Death, Whereas ICR4 Induced Acute, IFN-Independent Cell Death We next elucidated the mechanism of cytotoxicity induced by ICR2 and ICR4 in human cancer cells. Annexin V single positive cells represent early apoptosis, whereas Annexin V and 7-AAD double positive cells are primary and secondary necrotic cells.[9] Early apoptosis appeared at 4 h after transfection with ICR4 or polyI:C, and both early apoptosis and primary and secondary necrosis gradually increased in these cells during culture (FIGS. 3A-3G). In the cells transfected with ICR2, no significant cell death appeared at 4 h and only marginal early apoptosis and necrosis appeared at 24 h. Interestingly, cells transfected with ICR2 showed much more necrotic events than early apoptotic events at 48 h (FIGS. 3A-3E). It has been shown that T7 RNA polymerase has a RNA-dependent-RNA polymerase activity and T7 RNA polymerase-induced IVT potentially forms non-templated self-complementary products.[23] We observed that ICR2 produced by T7 RNA polymerase-induced IVT contained both expected length of ICR2 RNA and longer length of ICR2 IVT product than expected (FIG. 3I). Transfection with the longer length of ICR2 IVT product induced pronounced cell death at 24 h after transfection (FIGS. 3J-3K). To avoid non-specific cell death induced by IVT byproducts, expected length of ICRs were purified by polyacrylamide gel electrophoresis. Unlike cell death, IFN-β production by human melanoma cells was not observed at 4 h after transfection with ICR2, ICR4 or polyI:C. IFN-β was continuously detected at 24 h and 48 h after transfection. Cells transfected with ICR2 produced 8 to 10 fold higher amounts of IFN-β than cells transfected with ICR4 (FIG. 3H). IFN-3 is known to induce cell death via multiple mechanisms including caspase-dependent apoptosis[30] and programmed necrosis, called necroptosis.[31] Thus, we speculated that ICR2 induced IFN-dependent cancer cell death, whereas ICR4 induced IFN-independent cancer cell death. To further elucidate the mechanism(s) of IFN-dependent or -independent cell death by ICR2 and ICR4, human melanoma cells were transfected with either ICR2 or ICR4, followed by treatment with vaccinia virus encoded interferon α and β decoy receptor B18R. B18R significantly inhibited ICR2- and IFN-β-induced cell death but not ICR4-induced cell death (FIGS. 3F-3H). This data suggests that ICR2 induces cell death, at least in part, in an IFN-dependent manner, whereas ICR4 induces apoptosis in an IFN-independent manner.

Figure 4A:
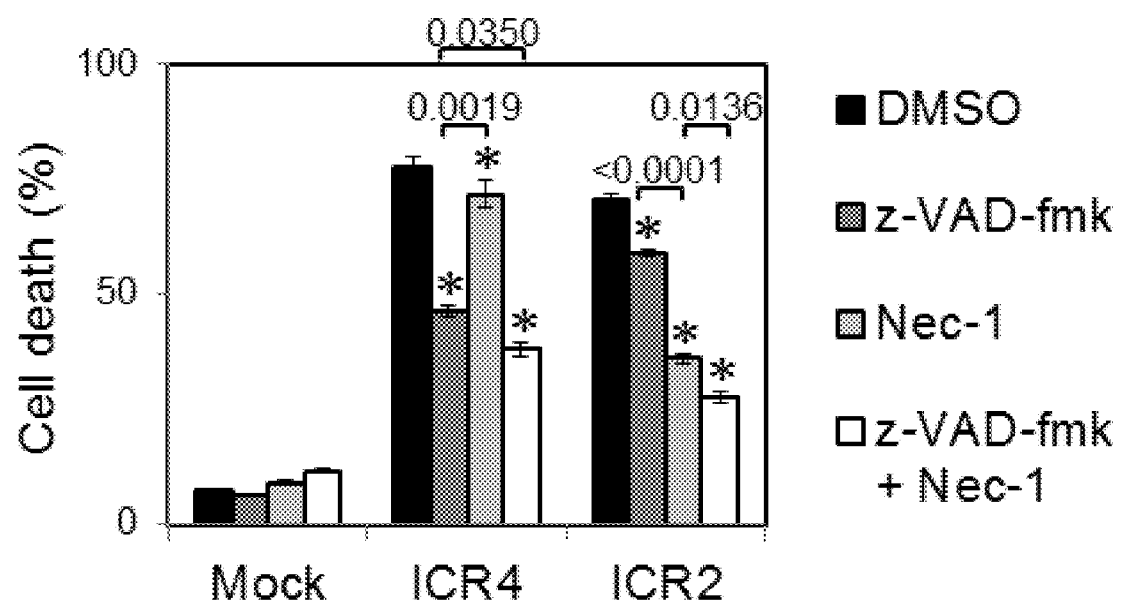
FIGS. 4A-4C show ICR2 and ICR4 trigger differential activation of cell death and PRR signaling pathways.
Figure 4B:
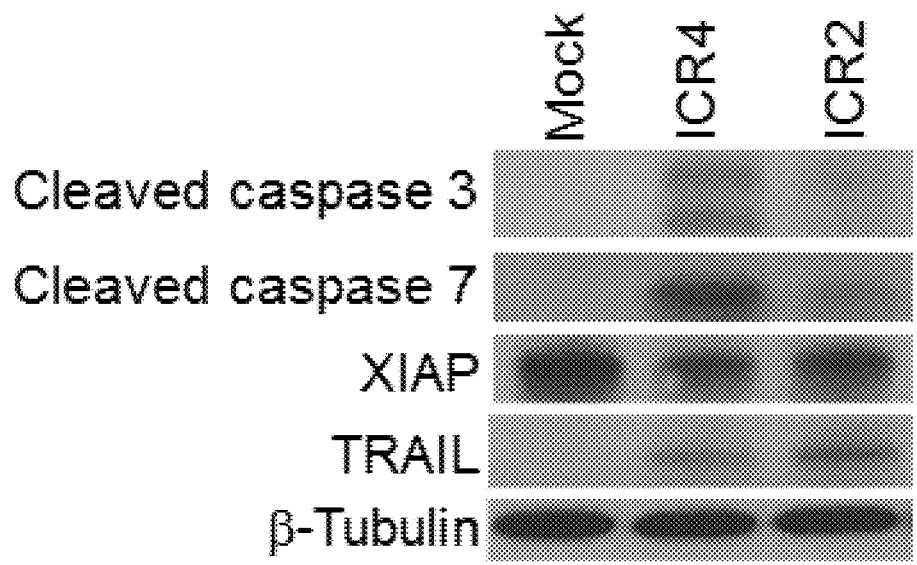
Figure 4C:
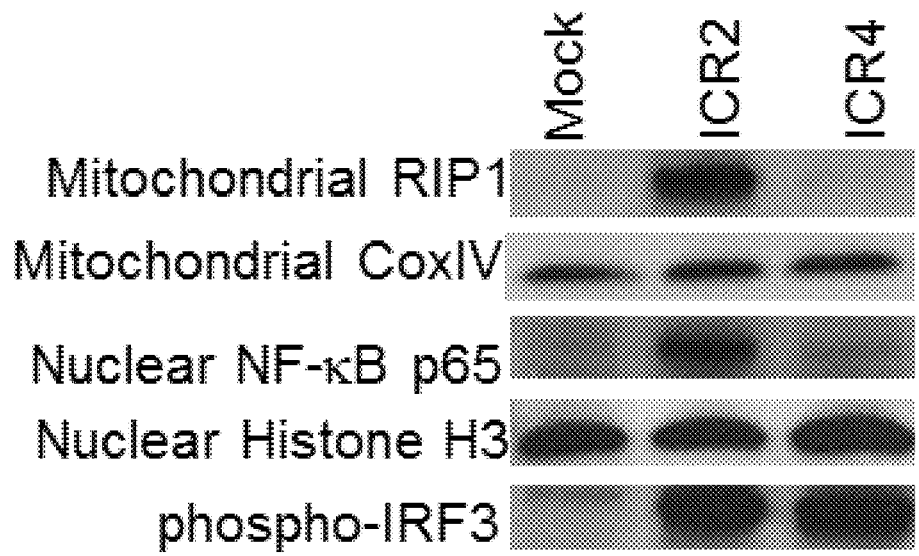

Example 4: ICR2 and ICR4 Triggered Different Cell Death Mechanisms in Human Cancer Cells We next investigated cell death mechanisms and signaling pathways in human cancer cells treated with ICR2 and ICR4. Z-VAD-fmk is a pan-caspase inhibitor and is thus considered an apoptosis inhibitor. Necrostatin-1 (Nec-1) is an inhibitor of receptor-interacting serine/threonine protein kinase 1 (RIP1) and commonly used as a necroptosis inhibitor. Cell death induced by ICR4 is more inhibited by z-VAD-fmk than by Nec-1, whereas the converse is true for ICR2 as cell death is more inhibited by Nec-1 than by z-VAD-fmk (FIG. 4A). Co-treatment with both z-VAD-fmk and Nec-1 inhibited cancer cell death to a greater extent than did single treatment with either z-VAD-fmk or Nec-1 (FIG. 4A). These data indicate that ICR2-induced cell death is much more dependent on RIP1 than caspases, whereas ICR4-induced cell death is more dependent on caspases than RIP1. Consistent with this result, the expression levels of cleaved Caspases 3 and 7 in melanoma cells treated with ICR4 were found to be much higher than in cells treated with ICR2 (FIG. 4B). In contrast, cells treated with ICR2 had significantly more RIP1 translocated in mitochondria than did cells treated with ICR4 (FIG. 4C). Interestingly, both ICR2 and ICR4 significantly downregulated anti-apoptotic protein X-linked inhibitor of apoptosis (XIAP) and upregulated pro-apoptotic protein TNF-related apoptosis-inducing ligand (TRAIL) in human melanoma cells (FIG. 4B). These observations suggest that both ICR2 and ICR4 sensitize human cancer cells to programmed cell death by downregulation of XIAP and upregulation of TRAIL.

Example 5: Differential Activation of NF-κB in Cancer Cells Treated with ICR2 and ICR4

Cells treated with ICR2 produced much more IFN-β and pro-inflammatory cytokines than did cells treated with ICR4 (FIGS. 2A-2D). We speculated that ICR2 and ICR4 differentially activated NF-kB and IRF signaling pathways which led to the expression of inflammatory cytokines and IFNs, respectively. NF-κB was highly detected in the nuclear fraction of cells transfected with ICR2 but only marginally detected in the nuclear fraction of cells transfected with ICR4, whereas phosphorylated IRF3 was similarly detected in cells transfected with either ICR2 or ICR4 (FIG. 4C). Activation of IRF3 is known to have dual roles in anti-viral responses, including induction of apoptosis and expression of type I IFN genes.[32] Although IRF3 was equally activated by ICR2 and ICR4 in human melanoma cells, IRF3 might play different roles in cells transfected with ICR2 and ICR4. Further studies are needed to elucidate the functional activity of IRF3 in cells transfected with ICR2 and ICR4.

Example 6: Activation of RNA-Sensing PRRs by ICR2 and ICR4

Figure 5A:
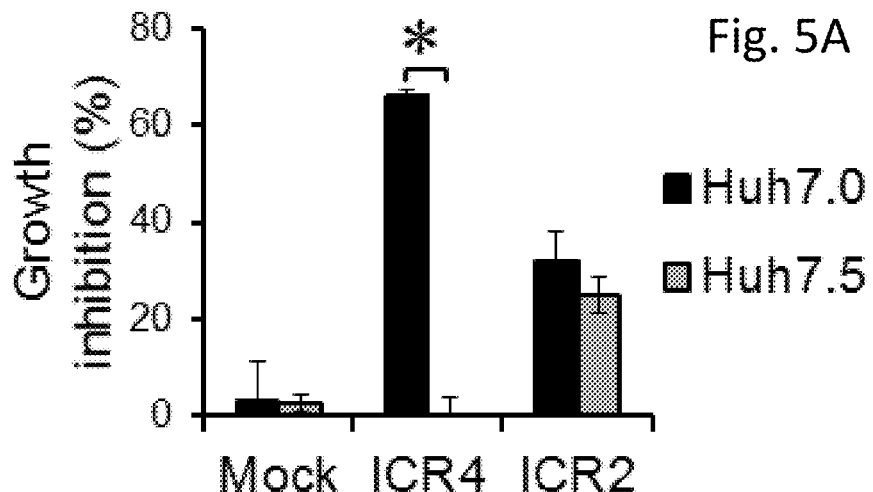
FIGS. 5A-5F show induction of RNA-sensing PRR-mediated cytotoxicity by ICR2 and ICR4.
Figure 5B:
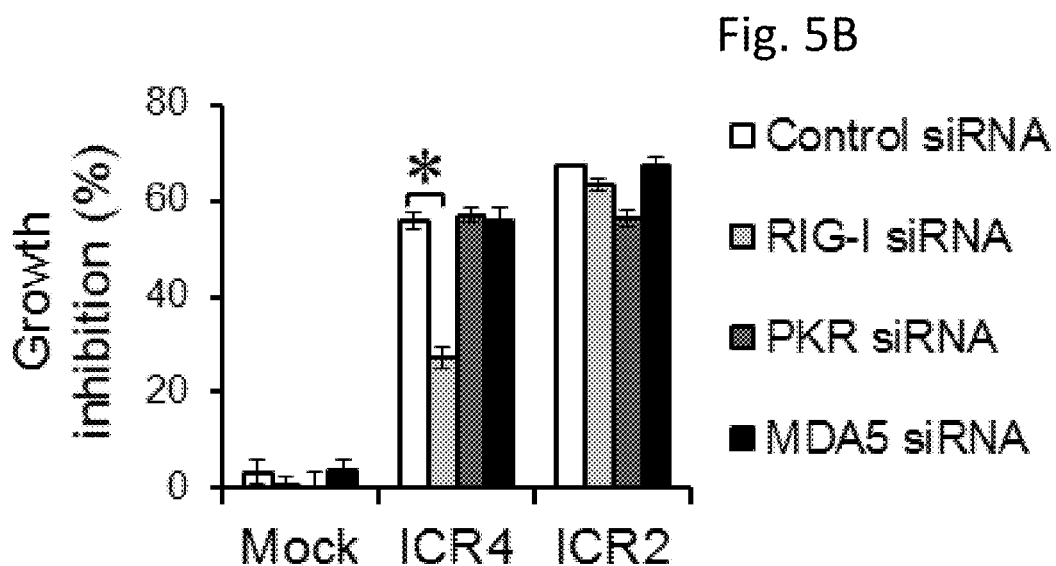
Figure 5C:
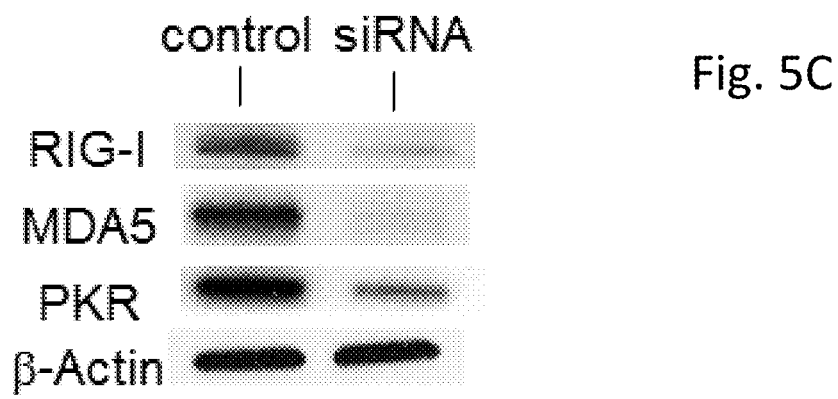
Figure 5D:
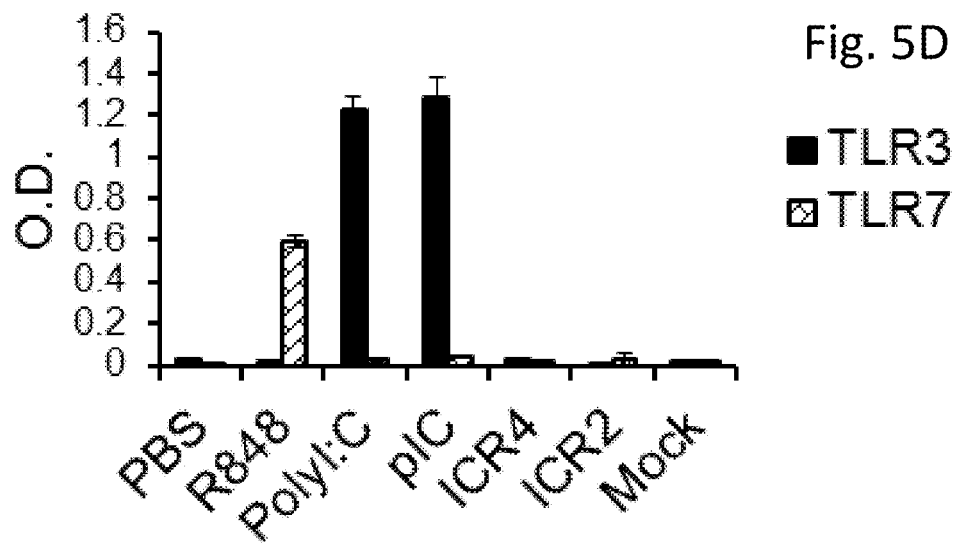
Figure 5E:
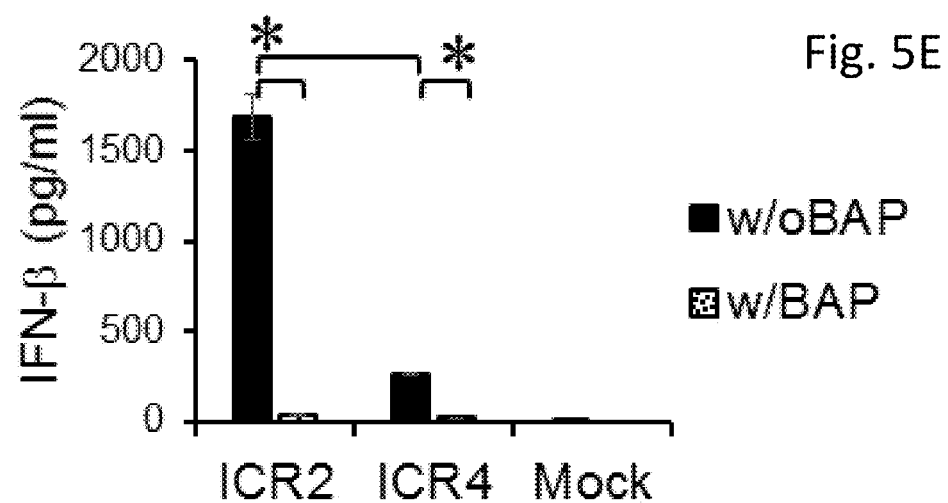
Figure 5F:
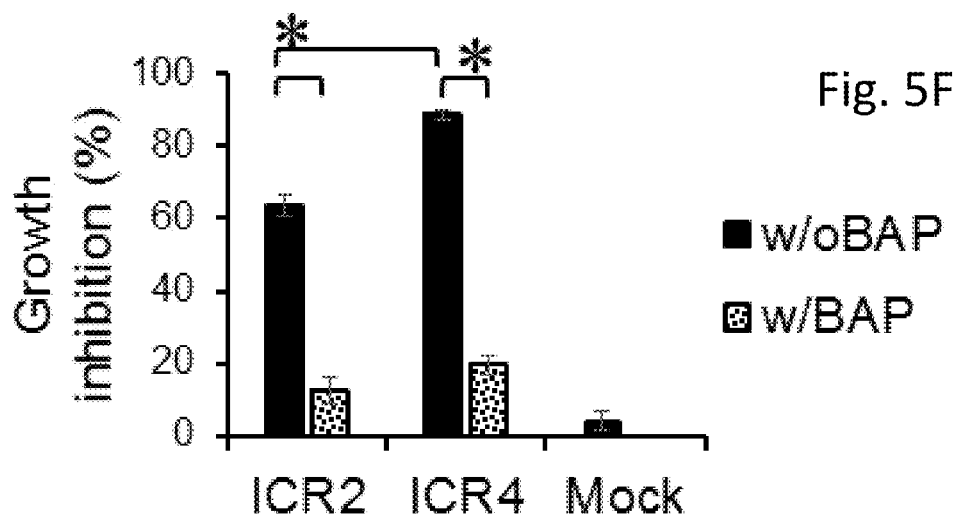
Figure 5G:
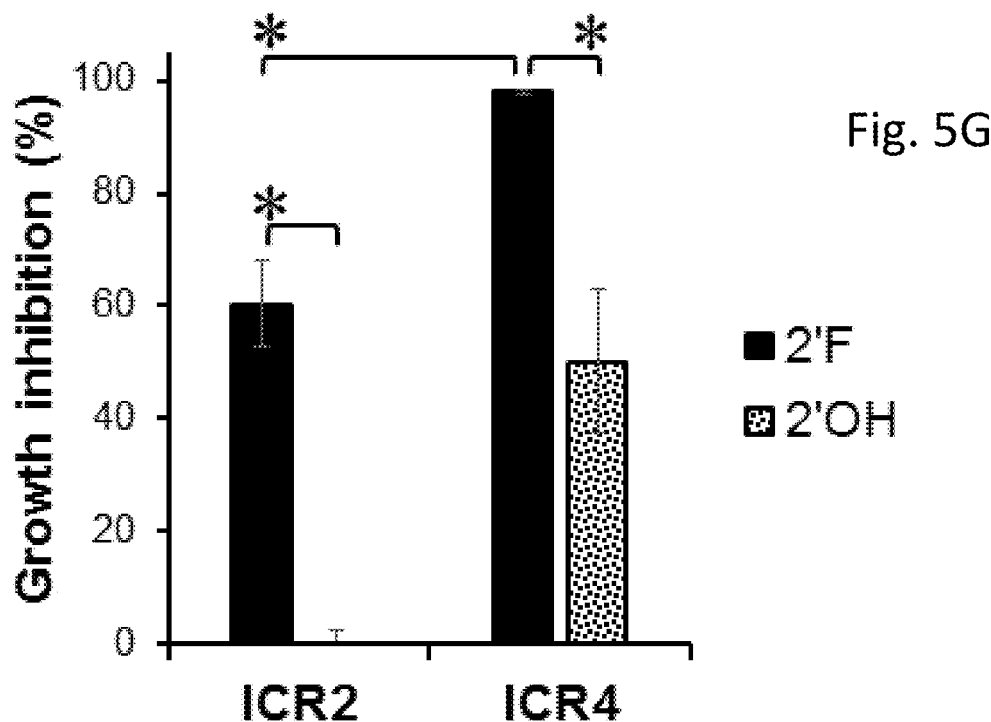
FIGS. 5G-5H show a comparison of cell death- and IFN-β-inducing activities of ICR2 and ICR4 containing 2'F pyrimidine or 2'OH pyrimidine. WM266-4 cells were transfected with 2'F ICR2, 2'OH ICR2, 2'F ICR4 or 2'OH ICR4 (35 nM each).
Figure 5H:
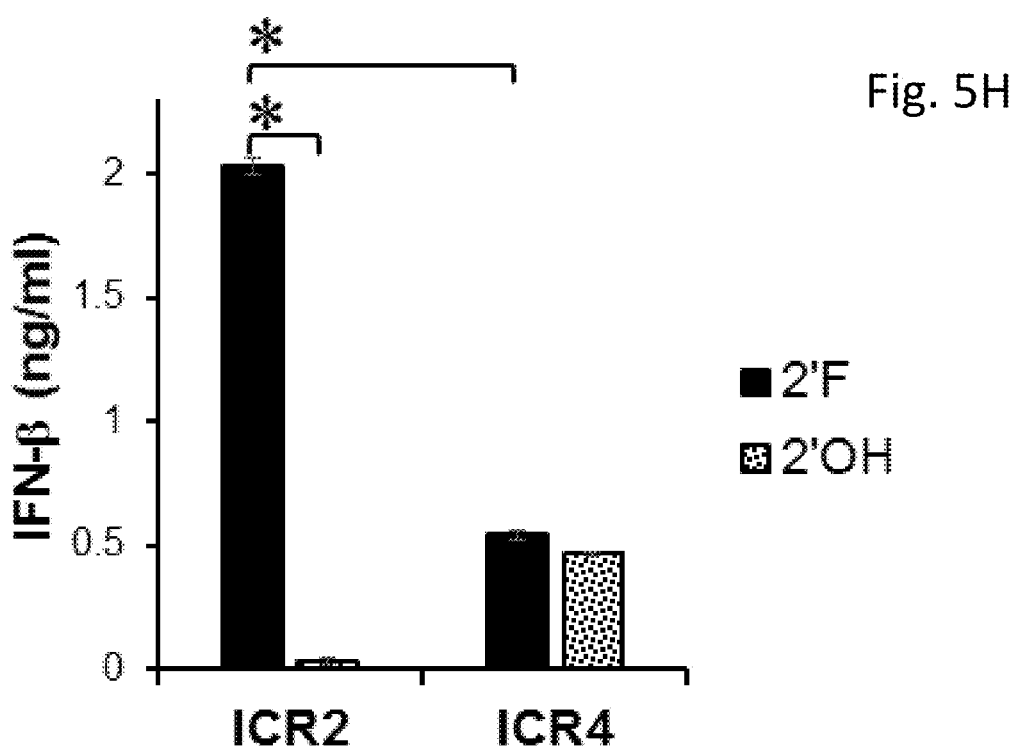

Our recent studies demonstrated that 2'F-modified RNA aptamers containing 5'ppp and stem loop(s) induced programmed cell death and IFN-β production by human melanoma and hepatocellular carcinoma cells in a RIG-I-dependent manner.[28] To answer whether ICR2 and ICR4 induced RIG-I-dependent cell death of human cancer cells, we treated Huh7.0, a RIG-I-wild type human hepatocellular carcinoma cell line, and Huh7.5, a RIG-I-mutant Huh7.0 cell line, with either ICR2 or ICR4. ICR4 was cytotoxic to Huh7.0 cells but not to Huh7.5 (FIG. 5A). Interestingly, ICR2 induced similar cytotoxicity in Huh7.0 and Huh7.5. Moreover, ICR4 but not ICR2 had significantly reduced cytotoxicity in human melanoma cells with siRNA-mediated RIG-I knockout, whereas ICR4 and ICR2 led to similar levels of cytotoxicity in human melanoma cells with knockout of other cytoplasmic RNA-sensing PRRs, including PKR and MDA5 (FIGS. 5B-5C). Furthermore, human TLR3 and TLR7 reporter cells were not stimulated by ICR2 and ICR4 (FIG. 5D). Removing 5'ppp of ICR2 and ICR4 by bacterial alkaline phosphatase (BAP)-induced dephosphorylation significantly prevented cell death and IFN-β production by human melanoma cells (FIG. 5E-5F). Interestingly, 2'OH pyrimidine-incorporated ICR4 significantly decreased cytotoxicity but not IFN-β-inducing activity compared to 2'F pyrimidine-incorporated ICR4, whereas 2'OH pyrimidine-incorporated ICR2 completely abrogated both cytotoxicity and IFN-β-inducing activity (FIGS. 5G-5H). Thus, ICR4 induced anti-cancer responses in RIG-I-dependent but PKR- and MDA5-independent manner. By contrast, ICR2-induced anti-cancer responses did not appear to be affected by the loss of RIG-I, MDA5 or PKR.

Example 7: ICR2 and ICR4 Induced Translocation of Calreticulin and HMGB1

Figure 6A:
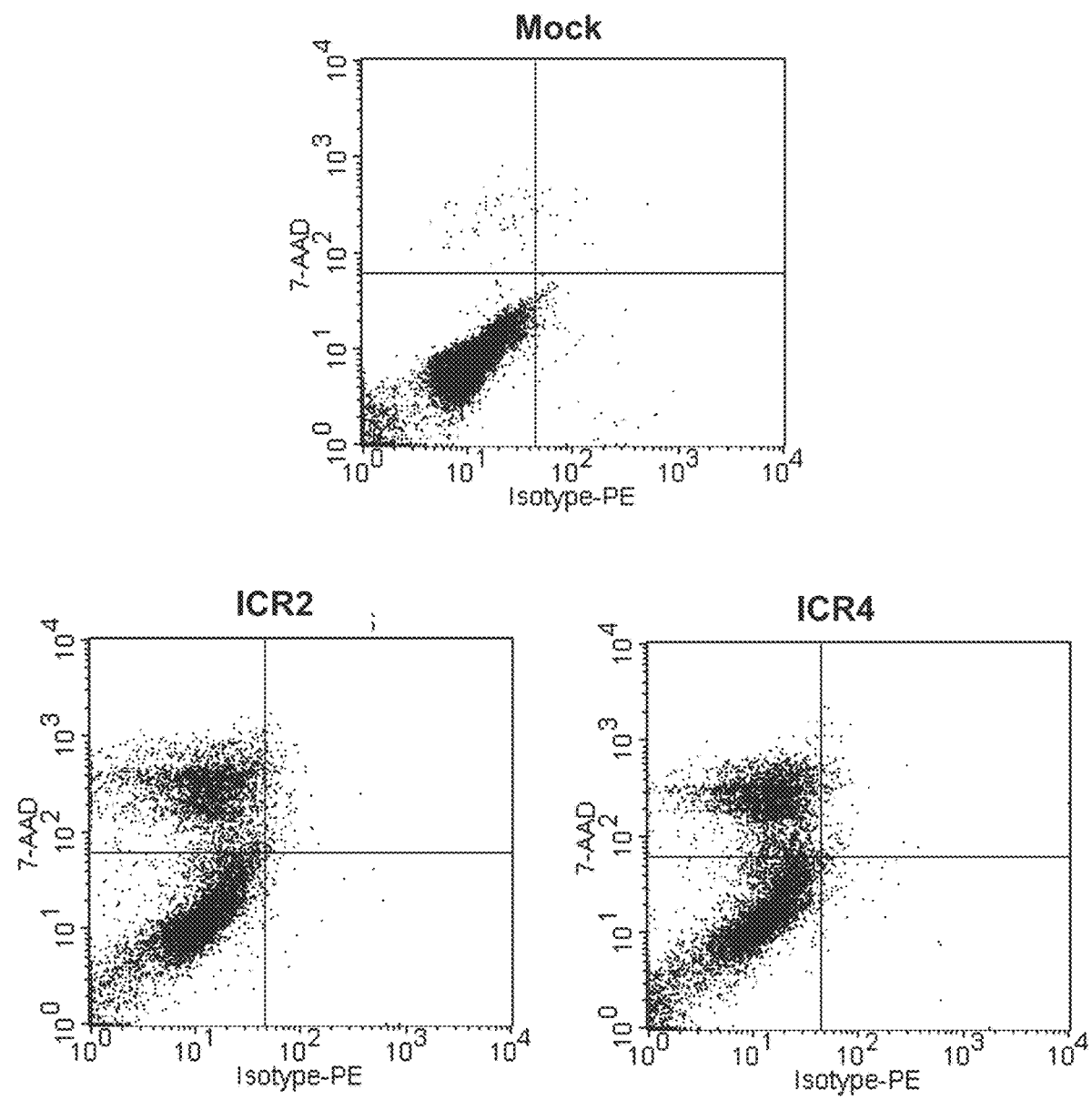
FIG. 6A-6G show release of innate immune stimulatory DAMPs and Calreticulin from human cancer cells after treatments with immunogenic cell death-inducing agents.
Figure 6A:
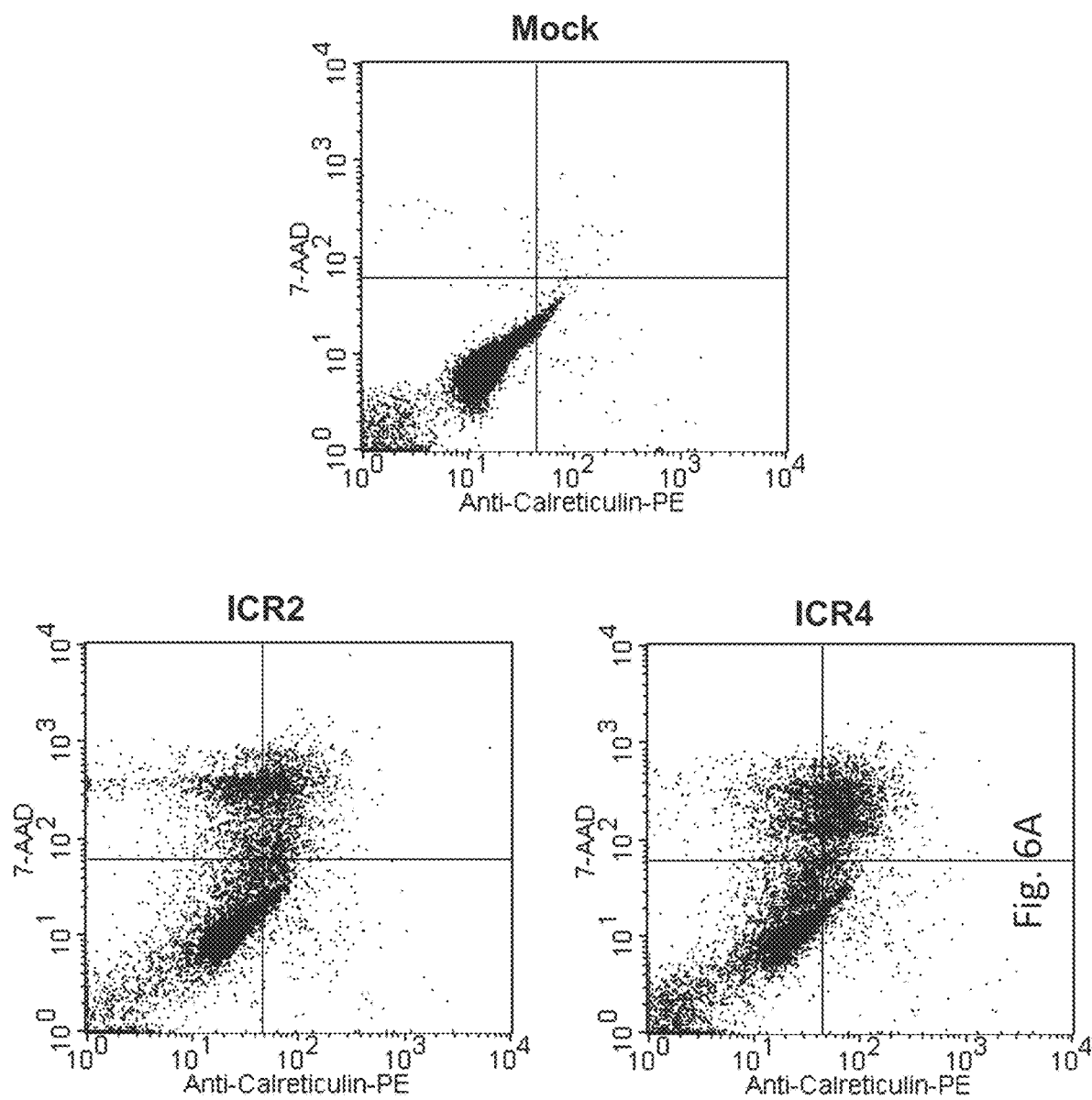
Figure 6B:
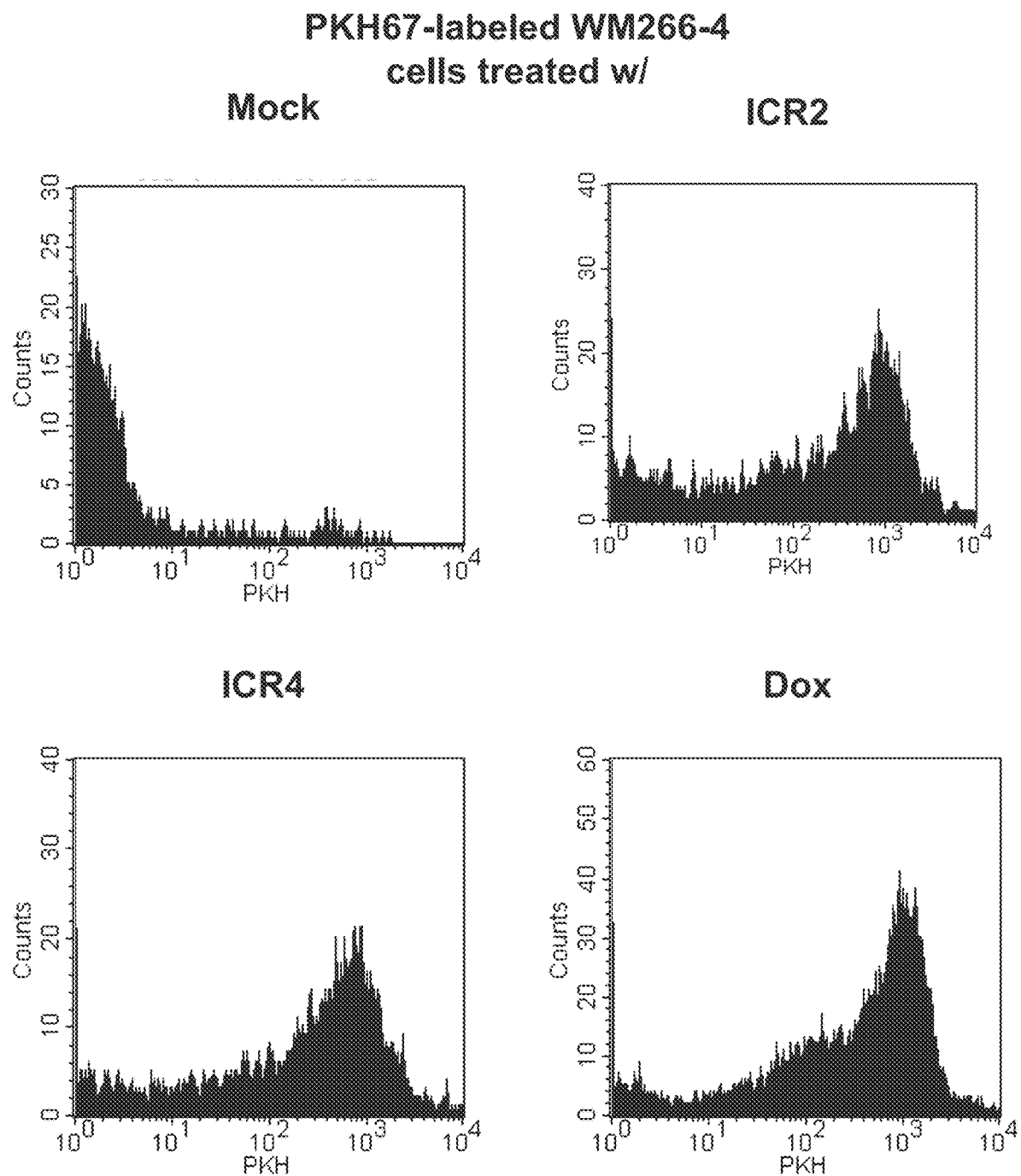
Figure 6C:
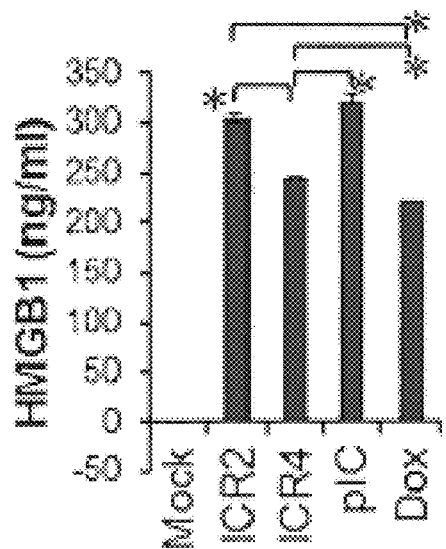
Figure 6D:
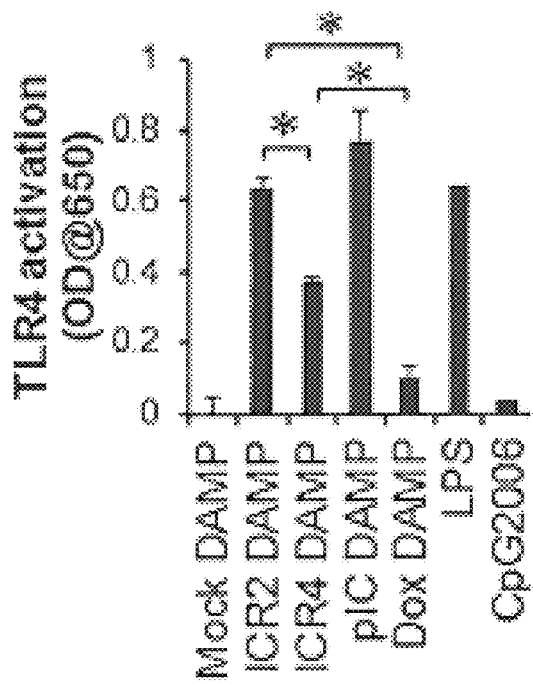
Figure 6E:
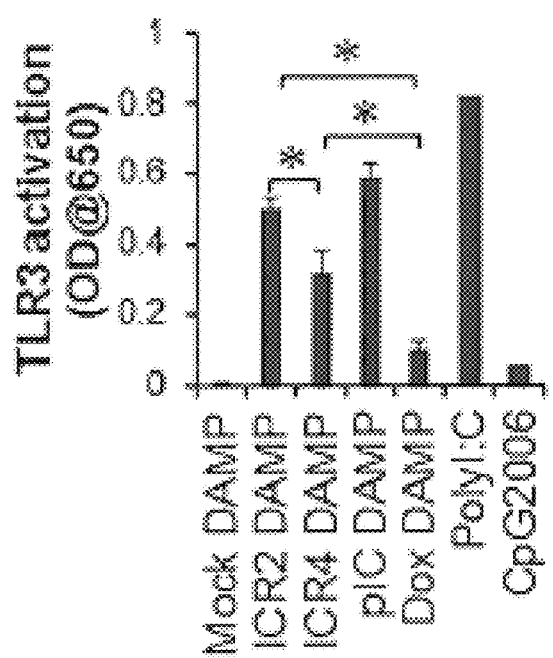
Figure 6F:
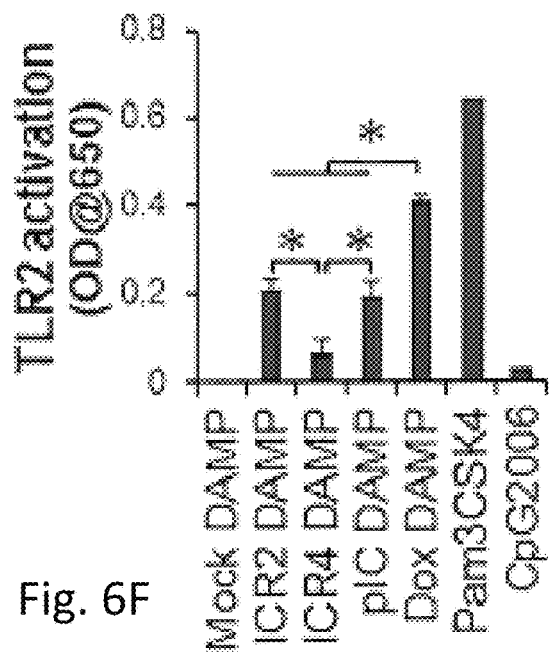
Figure 6G:
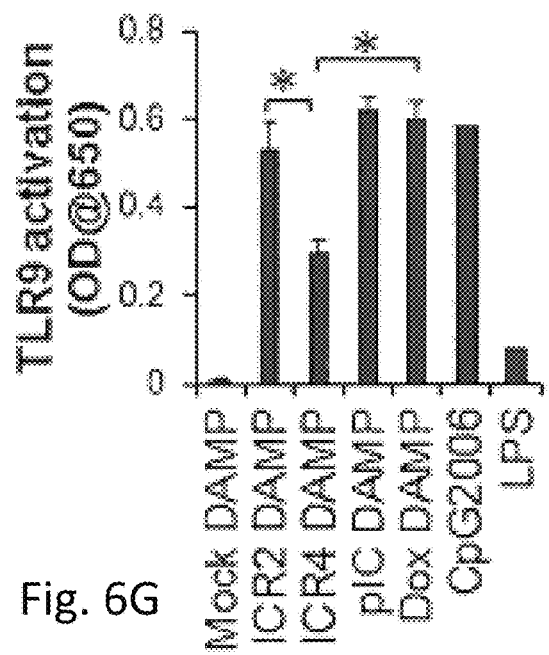
Figure 6H:
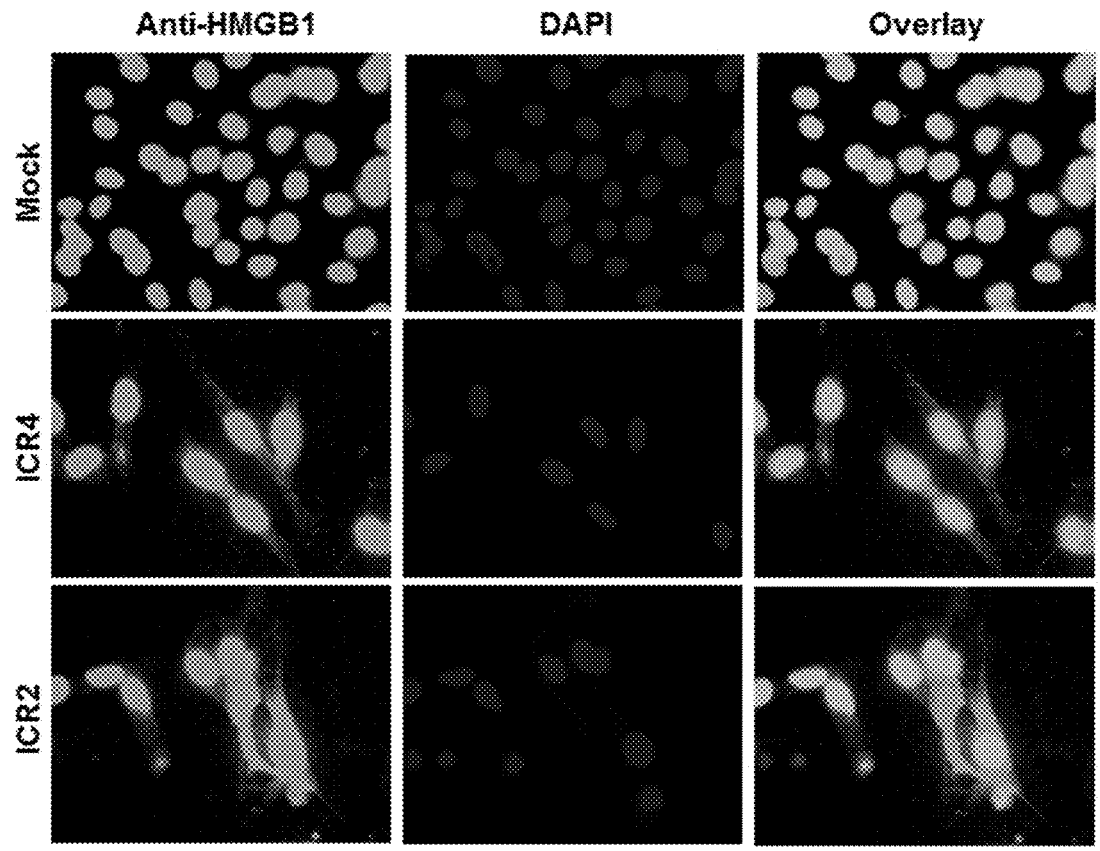
FIG. 6H shows cytoplasmic translocation of nuclear protein HMGB1 in cells transfected with ICR2 and ICR4. WM266-4 cells were transfected for 4 h with ICR2, ICR4 or transfection reagent alone (Mock). Cells were harvested at 24 h after transfection and co-stained with anti-HMGB1 (Green) and DAPI (blue). The expression of nuclear and cytoplasmic HMGB1 and nuclear DAPI was detected by fluoresce microscopy.

Certain types of anti-cancer agents, e.g., doxorubicin, can induce immunogenic cell death characterized by the release of DAMPs, the surface expression of "eat-me" signal (e.g., endoplasmic reticulum-residential protein Calreticulin) and the activation of innate immune cells such as DCs and NK cells.[23] This immunogenic cell death significantly contributes overall therapeutic outcomes of cancer therapies by the induction of anti-tumor immune responses. Both ICR2 and ICR4 slightly induced surface translocation of Calreticulin (FIG. 6A). It has been shown that surface Calreticulin facilitates phagocytosis of doxorubicin-treated cancer cells by DCs. To study phagocytosis of ICR2- and ICR4-treated cancer cells by DCs, human immature DCs were incubated with human melanoma cells killed by ICR2 and ICR4 as shown in FIG. 6B. These dead/dying cancer cells were taken up by DCs as effectively as cells killed by doxorubicin. Translocation of HMGB1 from the nucleus to the cytoplasm was also observed in human melanoma cells treated with ICR2 and ICR4 (FIG. 6H). Interestingly, treatment with ICR2 induced significantly higher levels of HMGB1 release from human melanoma cells than did treatment with ICR4 or doxorubicin, and similar high levels as treatment with polyI:C (FIG. 6C). Consistent with increased HMGB1 release, DAMPs generated by ICR2-induced melanoma cell death induced significantly more activation of HMGB1-recognizing TLR4 than DAMPs generated by ICR4-induced cell death (FIG. 6D), even though DAMPs released by ICR4-induced cell death were significantly more potent in stimulating TLR4 than DAMPs released by doxorubicin-induced cell death.

Figure 6I:
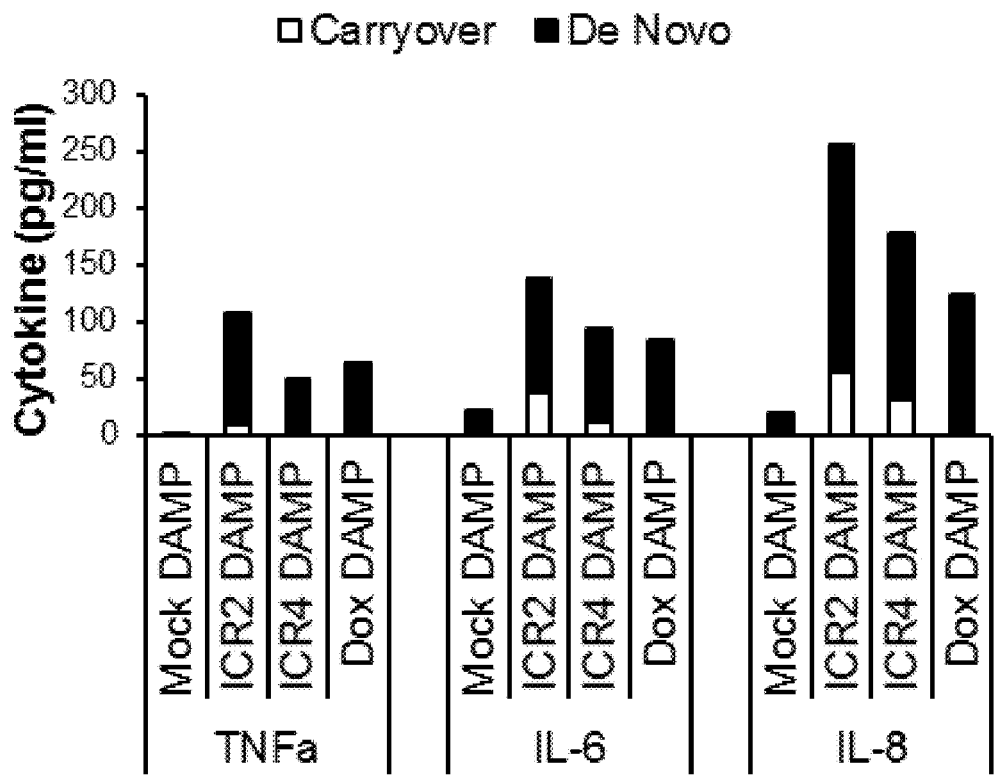
FIG. 6I shows human DCs stimulated with DAMPs produced cytokines. Human PBMC-derived immature DCs were stimulated with DAMPs isolated from WM266-4 cells treated with transfection reagent alone (Mock DAMP), ICR2 (ICR2 DAMP), ICR4 (ICR4 DAMP) or doxorubicin (Dox DAMP). De novo production of TNFα, IL-6 and IL-8 by stimulated DCs (De Novo) and pre-existing cytokines in DAMPs (Carryover) were determined by ELISA.
Figure 6J:
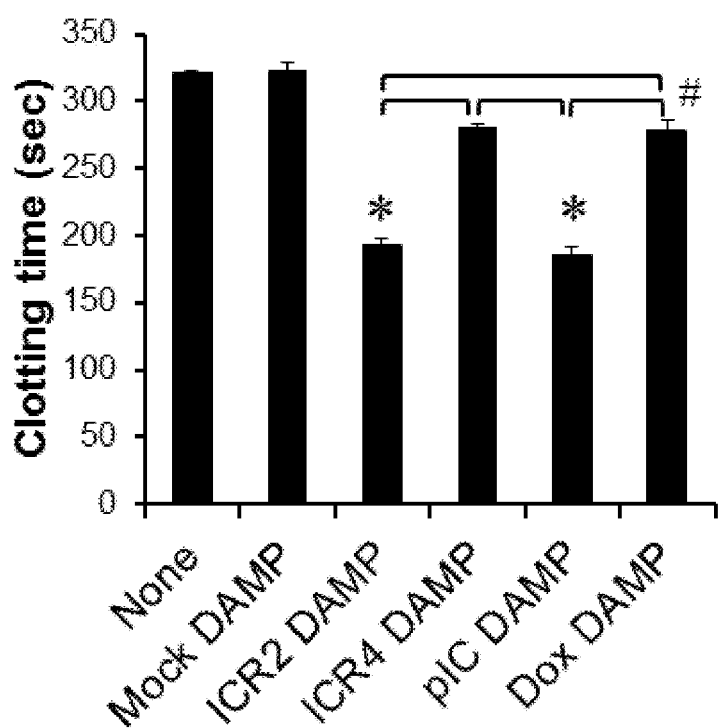
FIG. 6J shows release of pro-coagulative DAMPs from human cancer cells treated with immunogenic cell death inducing agents. Enhancement of human plasma coagulation by DAMPs released from cells treated with transfection reagent alone (Mock DAMP), ICR2 (ICR2 DAMP), ICR4 (ICR4 DAMP), polyI:C (pIC DAMP) and Doxorubicin (Dox DAMP) was determined by coagulation assay. n=3, Error bar are S.D. #P<0.05 (indicated comparison). *P<0.05 (vs normal plasma clotting time (None)).

Example 8: ICR2 and ICR4 Induced the Release of Innate Immune Stimulatory and Pro-Coagulant DAMPs from Human Cancer Cells To elucidate whether DAMPs released from cancer cells treated with ICR2 and ICR4 stimulate other TLRs, we collected and incubated DAMPs released from dead/dying human melanoma cells with TLR2, TLR3 and TLR9 reporter cells. The levels of activation of these TLR reporter cells were not significantly different between DAMPs released from ICR2-treated cells and from polyI:C-treated cells. DAMPs released from ICR2-treated cells, however, more potently activated TLR reporter cells than DAMPs released from ICR4-treated cells. ICR4-treated cells induced significantly higher TLR3 activation than doxorubicin-treated cells (FIG. 6E), whereas ICR4-treated cells induced significantly less TLR2 and TLR9 activation than doxorubicin-treated cells (FIGS. 6F-6G). These DAMPs released from ICR2- and ICR4-treated cancer cells stimulated immature human DCs to produce cytokines (FIG. 6I). In addition to immune stimulatory activities, DAMPs are known to facilitate hemostasis and thrombosis[35] and may play an important roles in tumor recurrence and metastasis after anti-cancer therapies.[36] Interestingly, DAMPs released from ICR2- and polyI:C-treated human melanoma cells activated coagulation of plasma compared to DAMPs released from mock-transfected cells, whereas DAMPs released from ICR4- and doxorubicin-treated melanoma cells did not significantly change plasma coagulation times (FIG. 6J). These data suggested that ICR4-treated cancer cells released lower amounts of innate immune stimulators and pro-coagulants than ICR2-treated cells.

Figure 7A:
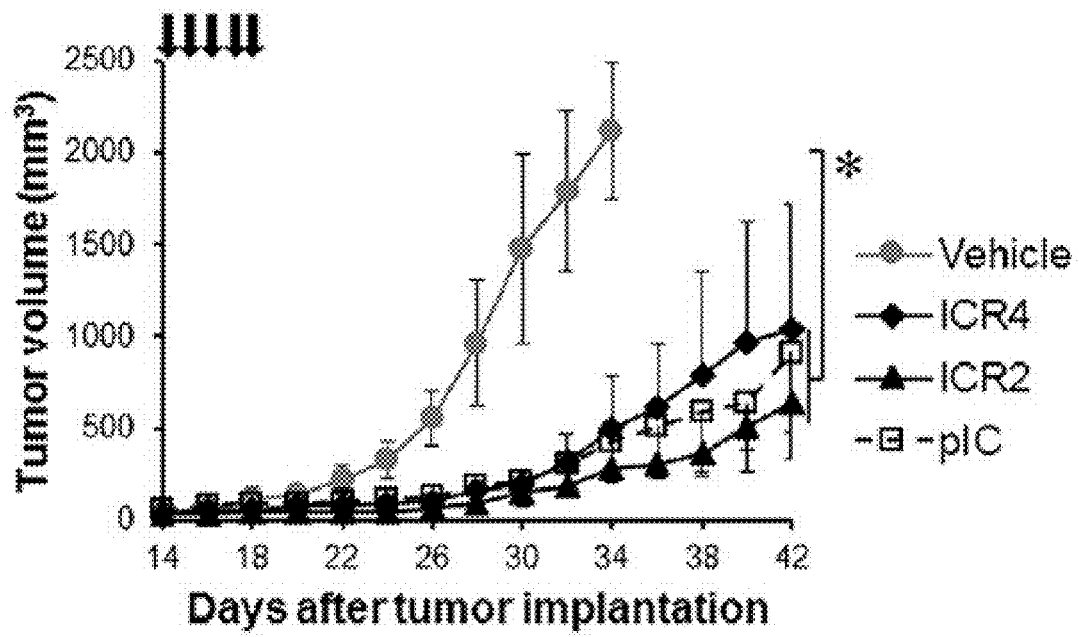
FIGS. 7A-7C shows inhibition of tumor growth by ICR2 and ICR4.
Figure 7B:
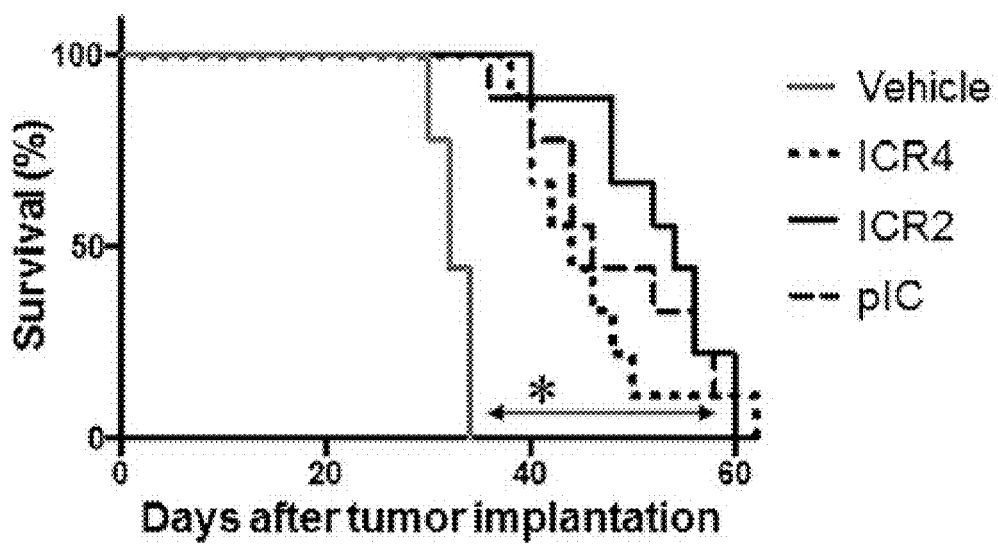
Figure 7C:
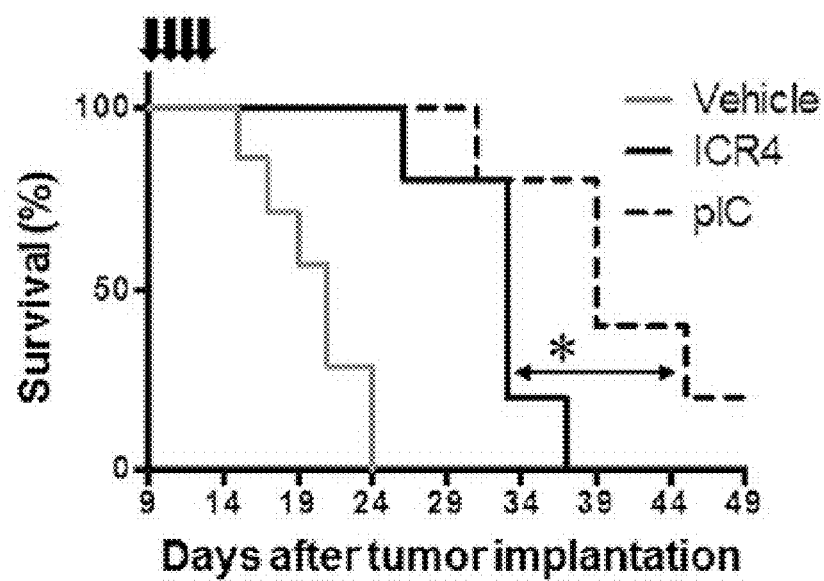

Example 9: In Vivo Transfection with ICR2 and ICR4 Extended Survival in Melanoma-Bearing Mice Finally, we evaluated the in vivo therapeutic efficacy of ICR2 and ICR4 in a human melanoma xenograft model. Repeated intratumoral treatments with ICR2 or ICR4 inhibited tumor growth (FIG. 7A) and significantly enhanced survival in nude mice with subcutaneous human melanoma xenografts (FIG. 7B). A trend toward reduced therapeutic effect of ICR4 compared with ICR2 and gold standard PRR-stimulating RNA agonist polyI:C was observed; however, the difference between ICR2, ICR4 and polyI:C was not statistically significant. In immunocompetent mice bearing B16 mouse melanoma, ICR4 treatment appeared to be significantly less therapeutically effective than polyI:C treatment (FIG. 7C).

We claim:

1. A composition capable of inducing cell death comprising a 5'-triphospate, 2'-fluoro modified pyrimidine non-linear RNA,
   wherein the RNA comprises:
   (a) a first stem-loop formed from the complete or partial hybridization of at least 8 nucleotide pairings;
   (b) a second stem-loop formed from the complete or partial hybridization of at least 8 nucleotide pairings; and
   (c) a spacer between the first stem-loop and the second stem loop,
   wherein the RNA comprises an oligonucleotide having at least 95% sequence identity to ICR2 (SEQ ID NO: 8).

2. The composition of claim 1, wherein the RNA comprises an oligonucleotide having at least 95% sequence identity to ICR4 (SEQ ID NO: 15), ICR4A (SEQ ID NO: 16), ICR5X (SEQ ID NO: 17), or ICR5Y (SEQ ID NO: 18).

3. The composition of claim 1, wherein the first stem-loop is formed from an oligonucleotide consisting essentially of ICR2 (SEQ ID NO: 8).

4. The composition of claim 1, wherein the RNA consists essentially of:
   (i) a ssRNA oligonucleotide having at least 95% sequence identity to ICR4 (SEQ ID NO: 15) or ICR4A (SEQ ID NO: 16); or
   (ii) a dsRNA comprising a first oligonucleotide having at least 95% sequence identity to ICR5X (SEQ ID NO: 17) completely or partially hybridized to a second oligonucleotide having at least 95% sequence identity to ICR5Y (SEQ ID NO: 18).

5. The composition of claim 1,
   wherein the first stem-loop comprises a 5'-triphosphate modified terminal nucleotide capable of hybridizing with its complement to form the first stem-loop or
   wherein the second stem-loop comprises a 5'-triphosphate modified terminal nucleotide or a 3' terminal nucleotide capable of hybridizing with its complement to form the second stem-loop.

6. The composition of claim 1, wherein the spacer comprises a single-stranded segment of RNA, wherein the spacer comprises a third stem loop formed from the complete or partial hybridization of at least 8 nucleotide pairings, or wherein the spacer comprises a double-stranded segment of RNA.

7. A composition capable of inducing cell death comprising 2'-fluoro modified pyrimidine non-linear RNA comprising a stem-loop formed from an oligonucleotide having at least 95% sequence identity to ICR2 (SEQ ID NO: 8), the oligonucleotide comprising a 5'-triphosphate modified terminal nucleotide capable of hybridizing with its complementary nucleotide to form the stem-loop.

8. The composition of claim 7, wherein the RNA further comprises a second stem loop formed from the complete or partial hybridization of at least 8 nucleotide pairings and a spacer between the stem-loop formed from an oligonucleotide having at least 95% sequence identity to ICR2 (SEQ ID NO: 8) and the second stem loop.

9. The composition of claim 8, wherein the RNA comprises an oligonucleotide having at least 95% sequence identity to ICR4 (SEQ ID NO: 15), ICR4A (SEQ ID NO: 16), ICR5X (SEQ ID NO: 17), or ICR5Y (SEQ ID NO: 18).

10. The composition of claim 8, wherein the stem-loop is formed from an oligonucleotide consisting essentially of ICR2 (SEQ ID NO: 8).

11. The composition of claim 1 further comprising a therapeutic agent.

12. The composition of claim 1 further comprising a cytoplasmic delivery composition.

13. A pharmaceutical composition comprising a therapeutically effective amount of the composition of claim 1 and one or more pharmaceutically acceptable carriers, excipients, or diluents.

14. A method of inhibiting growth of cells or inducing cell death comprising contacting cells with the composition as in claim 1 in an amount effective to inhibit the growth of the cells or induce death of the cells.

15. A method of inhibiting growth of cells or inducing cell death in a subject comprising administering the composition as in claim 1 to the subject in need of such treatment in an amount effective to inhibit the growth of the cells or induce death of the cells.

16. The method of claim 14, wherein the cells comprise cancer cells.

17. 3The method of claim 14, wherein the composition is delivered into cytoplasm for at least a plurality of the cells.

18. The method of claim 15, wherein the cells comprise cancer cells.

19. The method of claim 15, wherein the composition is delivered into cytoplasm for at least a plurality of the cells.

20. The composition of claim 1, wherein the RNA comprises ICR4 (SEQ ID NO: 15), ICR4A (SEQ ID NO: 16), or ICR5X (SEQ ID NO: 17) completely or partially hybridized to ICR5Y (SEQ ID NO: 18).

* * * * *

SEQUENCE LISTING

```
<160> NUMBER OF SEQ ID NOS: 19

<210> SEQ ID NO 1
<211> LENGTH: 25
<212> TYPE: RNA
<213> ORGANISM: Artificial Sequence
<220> FEATURE:
<223> OTHER INFORMATION: Synthetic: ICR1

<400> SEQUENCE: 1
ggaugcggua ccugacagca uccua                                            25

<210> SEQ ID NO 2
<211> LENGTH: 30
<212> TYPE: RNA
<213> ORGANISM: Artificial Sequence
<220> FEATURE:
<223> OTHER INFORMATION: Synthetic: ICR1A

<400> SEQUENCE: 2
ggaugcggua ccugacagca uccuaaagug                                       30

<210> SEQ ID NO 3
<211> LENGTH: 41
<212> TYPE: RNA
<213> ORGANISM: Artificial Sequence
<220> FEATURE:
<223> OTHER INFORMATION: Synthetic: ICR1B

<400> SEQUENCE: 3
ggaugcggua ccugacagca uccuaaagug guggaaguga g                          41
```

<210> SEQ ID NO 4
<211> LENGTH: 56
<212> TYPE: RNA
<213> ORGANISM: Artificial Sequence
<220> FEATURE:
<223> OTHER INFORMATION: Synthetic: ICR1C

<400> SEQUENCE: 4
ggaugcggua ccugacagca uccuaaagug guggaaguga gugagugaaa uaaaaa        56

<210> SEQ ID NO 5
<211> LENGTH: 17
<212> TYPE: RNA
<213> ORGANISM: Artificial Sequence
<220> FEATURE:
<223> OTHER INFORMATION: Synthetic: ICR2-3

<400> SEQUENCE: 5
ggacguaccu gacgucc                                                   17

<210> SEQ ID NO 6
<211> LENGTH: 19
<212> TYPE: RNA
<213> ORGANISM: Artificial Sequence
<220> FEATURE:
<223> OTHER INFORMATION: Synthetic: ICR2-2

<400> SEQUENCE: 6
ggaucguacc ugacgaucc                                                 19

<210> SEQ ID NO 7
<211> LENGTH: 21
<212> TYPE: RNA
<213> ORGANISM: Artificial Sequence
<220> FEATURE:
<223> OTHER INFORMATION: Synthetic: ICR2-1

<400> SEQUENCE: 7
ggaucgguac cugacagauc c                                              21

<210> SEQ ID NO 8
<211> LENGTH: 23
<212> TYPE: RNA
<213> ORGANISM: Artificial Sequence
<220> FEATURE:
<223> OTHER INFORMATION: Synthetic: ICR2

<400> SEQUENCE: 8
ggaugcggua ccugacagca ucc                                            23

<210> SEQ ID NO 9
<211> LENGTH: 29
<212> TYPE: RNA
<213> ORGANISM: Artificial Sequence
<220> FEATURE:
<223> OTHER INFORMATION: Synthetic: ICR2A

<400> SEQUENCE: 9
ggacgaugcg guaccugaca gcaucgucc                                      29

<210> SEQ ID NO 10
<211> LENGTH: 51
<212> TYPE: RNA
<213> ORGANISM: Artificial Sequence
<220> FEATURE:
<223> OTHER INFORMATION: Synthetic: ICR2B

<400> SEQUENCE: 10
ggaugcggua ccugacagca uccaccuggg augcugucag guaccgcauc c        51

<210> SEQ ID NO 11
<211> LENGTH: 28
<212> TYPE: RNA
<213> ORGANISM: Artificial Sequence
<220> FEATURE:
<223> OTHER INFORMATION: Synthetic: ICR3

<400> SEQUENCE: 11
ggagcggaug cgguaccuga cagcaucc        28

<210> SEQ ID NO 12
<211> LENGTH: 35
<212> TYPE: RNA
<213> ORGANISM: Artificial Sequence
<220> FEATURE:
<223> OTHER INFORMATION: Synthetic: ICR3A

<400> SEQUENCE: 12
ggggaggaca gcggaugcgg uaccugacag caucc        35

<210> SEQ ID NO 13
<211> LENGTH: 42
<212> TYPE: RNA
<213> ORGANISM: Artificial Sequence
<220> FEATURE:
<223> OTHER INFORMATION: Synthetic: ICR3B

<400> SEQUENCE: 13
ggaaugaggg gaggacagcg gaugcgguac cugacagcau cc        42

<210> SEQ ID NO 14
<211> LENGTH: 49
<212> TYPE: RNA
<213> ORGANISM: Artificial Sequence
<220> FEATURE:
<223> OTHER INFORMATION: Synthetic: ICR3C

<400> SEQUENCE: 14
ggguaaguga augaggggag gacagcggau gcgguaccug acagcaucc        49

<210> SEQ ID NO 15
<211> LENGTH: 55
<212> TYPE: RNA
<213> ORGANISM: Artificial Sequence
<220> FEATURE:
<223> OTHER INFORMATION: Synthetic: ICR4

<400> SEQUENCE: 15
ggaugcggua ccugacagca uccuaaacuc augguccaug uuugccaug gacca        55

<210> SEQ ID NO 16
<211> LENGTH: 86
<212> TYPE: RNA
<213> ORGANISM: Artificial Sequence
<220> FEATURE:
<223> OTHER INFORMATION: Synthetic: ICR4A

<400> SEQUENCE: 16
ggaugcggua ccugacagca uccuaaacuc augguccaug uuugccaug gaccaacuac        60 cgacauugua uguuugaua uaaugu        86

```
<210> SEQ ID NO 17
<211> LENGTH: 39
<212> TYPE: RNA
<213> ORGANISM: Artificial Sequence
<220> FEATURE:
<223> OTHER INFORMATION: Synthetic: ICR5X

<400> SEQUENCE: 17
ggaugcggua ccugacagca uccugaguuu aguuguugu                              39

<210> SEQ ID NO 18
<211> LENGTH: 39
<212> TYPE: RNA
<213> ORGANISM: Artificial Sequence
<220> FEATURE:
<223> OTHER INFORMATION: Synthetic: ICR5Y

<400> SEQUENCE: 18
ggaugcggua ccugacagca uccacaacaa cuaaacuca                              39

<210> SEQ ID NO 19
<211> LENGTH: 23
<212> TYPE: RNA
<213> ORGANISM: Artificial Sequence
<220> FEATURE:
<223> OTHER INFORMATION: Synthetic: ICR-L

<400> SEQUENCE: 19
gguuuuuuuu uuuuuuuuuu uuu                                               23
```